US010047142B2

(12) United States Patent
Meems et al.

(10) Patent No.: US 10,047,142 B2
(45) Date of Patent: Aug. 14, 2018

(54) FACTOR VIII VARIANTS HAVING A DECREASED CELLULAR UPTAKE

(71) Applicants: Novo Nordisk A/S, Bagsvaerd (DK); Sanquin Blood Supply Foundation, Amsterdam (NL)

(72) Inventors: Henriet Meems, Amsterdam (NL); Alexander Benjamin Meijer, Amsterdam (NL); Koenraad Mertens, Amsterdam (NL); Ole Hvilsted Olsen, Broenshoej (DK); Kasper Lamberth, Stenloese (DK); Peder Lisby Noerby, Birkeroed (DK); Laust Bruun Johnsen, Skodsborg (DK); Marianne Hjortnes Kjalke, Frederikssund (DK); Henning Ralf Stennicke, Kokkedal (DK); Johannes Jacobus Voorberg, Wormer (NL); Maartje Van Den Biggelaar, Amsterdam (NL)

(73) Assignees: Novo Nordisk A/S, Bagsvaerd (DK); Sanquin Blood Supply Foundation, Amsterdam (NL)

( * ) Notice: Subject to any disclaimer, the term of this patent is extended or adjusted under 35 U.S.C. 154(b) by 0 days.

(21) Appl. No.: 15/355,475

(22) Filed: Nov. 18, 2016

(65) Prior Publication Data
US 2017/0066813 A1 Mar. 9, 2017

Related U.S. Application Data

(63) Continuation of application No. 14/862,934, filed on Sep. 23, 2015, now abandoned, which is a continuation of application No. 13/822,942, filed as application No. PCT/EP2011/065913 on Sep. 14, 2011, now Pat. No. 9,321,827.

(60) Provisional application No. 61/384,731, filed on Sep. 21, 2010, provisional application No. 61/507,666, filed on Jul. 14, 2011.

(30) Foreign Application Priority Data

Sep. 15, 2010 (EP) .................................... 10176731
Jul. 13, 2011 (EP) .................................... 11173768

(51) Int. Cl.
C07K 14/755 (2006.01)
A61K 38/37 (2006.01)
A61P 7/00 (2006.01)
A61K 38/00 (2006.01)

(52) U.S. Cl.
CPC ............ C07K 14/755 (2013.01); *A61K 38/00* (2013.01)

(58) Field of Classification Search
CPC .................... C07K 14/755; A61K 38/00
See application file for complete search history.

(56) References Cited

U.S. PATENT DOCUMENTS

| 5,972,885 A * | 10/1999 | Spira ................ A61K 38/37 514/13.5 |
| 6,759,216 B1 | 7/2004 | Lollar |
| 2003/0143596 A1 | 7/2003 | Bentley et al. |
| 2009/0076237 A1 | 3/2009 | Turecek et al. |

FOREIGN PATENT DOCUMENTS

| WO | WO 91/09122 A1 * | 6/1991 | .......... C07K 14/755 |
| WO | WO 94/15625 A1 * | 7/1994 | .......... C07K 14/755 |
| WO | 00/28021 A1 | 5/2000 | |
| WO | 2003/031464 A2 | 4/2003 | |
| WO | 03/047507 A2 | 6/2003 | |
| WO | 2008/025856 A2 | 3/2008 | |
| WO | 2008151258 A2 | 12/2008 | |

OTHER PUBLICATIONS

Harris et al, Effect of Pegylation on Pharmaceuticals, Nature Reviews, 2003, 2, pp. 214-221.*
Ananyeva et al, Trends in Cardiovascular Medicine, Catabolism of the Coagulation Factor VIII: Can We Prolong Lifetime of F VIII in Circulation, 2001, vol. 11, No. 6, pp. 251-257.
Barrow R T et al, Blood, Amino Acid Residues R2215, R2220, and F2196 Contribute to the Antigenicity of the Human Factor VIII C2 Domain Toward Inhibitory Antibodies, 2001, vol. 98, No. 11, pp. 531A Abstract #2220.
Fisher et al, Molecular Cell, Structure of an LDLR-RAP Complex Reveals a General Mode for Ligand Recognition by Lipoprotein Receptors, 2006, vol. 22, pp. 277-283.
Gilbert G E et al, Blood, Four Hydrophobic Amino Acids of the Factor VIII C2 Domain in Contribute to the Membrane-Binding Motif, 2000, vol. 96, No. 11, pp. 633a.
Hsu et al, 50th ASH Annual Meeting and Exposition, A FVIII C1 Domain Loop Containing PHE2093 Contributes Affinity to the Binding of Recombinant FVIII C1C2 Proteins to Activated Platelets, 2008 Abstract only, 2 pages.
Jensen et al., Journal of Molecular Biology., Binding Site Structure of One LRP-RAP Complex: Implications for a Common Ligand-Receptor Binding Motif, 2006, vol. 362, pp. 700-716.
Lin Jasper et al, Blood, Six Amino Acid Residues in a 1200 Angstrom(2) Interface Mediate Binding of Factor VIII to an IGG4 Infiibitory Antibody, 2008, vol. 112, No. 11, Abstract only, 2 pages.
Lu et al, Blood, A Membrane-Interactive Surface on the Factor VIII C1 Domain Cooperates with the C2 Domain for Cofactor Function, 2011, vol. 117, No. 11, pp. 3181-3189.
Meems H. et al, Journal of Thrombosis and Haemostasis, Lysine Residues 2065 and 2092 of the Factor VIII CI Domain Contribute to Binding LRP and LDL Receptor, But Are Not Involved in Binding Factor IXA, 2007, vol. 5, No. 2, pp. 1-2.
Meems et al, Blood, Factor VIII C1 Domain Residues Lys 2092 and Phe 2093 Contribute to Membrane Binding and Cofactor Activity, 2009, vol. 114, No. 18, pp. 3938-3946.
Mei Baisong et al, Blood, Rational Design of a Fully Active, Long-Acting Pegylated Factor VIII for Hemophilia A Treatment, 2010, vol. 116, No. 2, pp. 270-279.

(Continued)

Primary Examiner — Julie Ha
Assistant Examiner — Li N Komatsu
(74) Attorney, Agent, or Firm — Rosemarie R. Wilk-Orescan

(57) ABSTRACT

The present invention relates to modified coagulation factors. In particular, the present invention relates to modied Factor VIII molecules having decreased cellular uptake.

6 Claims, 5 Drawing Sheets

(56) References Cited

OTHER PUBLICATIONS

Rottensteiner H et al, Blood, Pegylation or Polysialylation Reduces FVIII Binding to LRP Resulting in Prolonged Half-Line in Murine Models, 2007, vol. 118, No. 11, Abstract only, 2 pages.
Saenko E L et al, Haemophilia, Receptor-Mediated Clearance of Factor VIII: Implications for Pharmacokinetic Studies in Individuals With Haemophilia, 2006, vol. 12, No. 4, pp. 15-22.
Skeldal et al, FEBS, Binding Areas of Urokinase-Type Plasminogen Activator—Plasminogen Activator Inhibitor-1 Complex for Endocytosis Receptors of the Low-Density Lipoprotein Receptor Family, Determined by Site-Directed, 2006, vol. 273, pp. 5143-5159.
Gilbert G E et al. Four Hydrophobic Amino Acids of the Factor VIII C2 Domain Are Constituents of Both the Membrane-binding and von Willebrand Factor-binding Motifs, "The journal of Biological Chemistry" Year 2002, vol. 277, No. 8, pp. 6374-6381.
Lenting P J et al. Clearance mechanisms of von Willebrand factor and factor, "Journal of Thrombosis and Haemostasis" Year 2007, vol. 5, pp. 1353-1360.
Ngo et al, Crystal Structure of Human Factor VIII: Implications for the Formation of the Factor IXa-Factor VIIIa Complex,Journal:Structure,Year 2008,vol. 16, pp. 597-606.
Tallarida, Drug synergism and dose-effect data analysis, Year 2000, pp. 1-29.
Liu, Miao-Liang et al. "Hemophilic Factor VIII C1- and C2-domain Missense Mutations and Their Modeling to the 1.5- anstrom Human C2-domain Crystal Structure." Blood. 2000 vol. 96(3) pp. 979-987.
J. D. Dimitrov et al. "A Human FVII inhibitor Modulates FVIII Surface Electrostatics at a VWF-binding Site Distant from its Epitope." Journal of Thrombosis and Haemostasis. 2010 vol. 8 pp. 1524-1531.

\* cited by examiner

# FACTOR VIII VARIANTS HAVING A DECREASED CELLULAR UPTAKE

CROSS-REFERENCE TO RELATED APPLICATIONS

This application is a continuation of U.S. application Ser. No. 14/862,934, filed Sep. 23, 2015 (now abandoned), which is a continuation of U.S. application Ser. No. 13/822,942, filed Nov. 8, 2013 (now U.S. Pat. No. 9,321,827, issued Apr. 26, 2016), which is a 35 U.S.C. § 371 National Stage application of International Application PCT/EP2011/065913 (WO 2012/035050), filed Sep. 14, 2011, which claimed priority of European Patent Applications 10176731.7, filed Sep. 15, 2010 and 11173768.0, filed Jul. 13, 2011; this application claims priority under 35 U.S.C. § 119 of U.S. Provisional Applications 61/384,731, filed Sep. 21, 2010 and 61/507,666; filed Jul. 14, 2011; the contents of which are incorporated herein by reference.

SEQUENCE LISTING

The instant application contains a Sequence Listing which has been submitted in ASCII format via EFS-Web and is hereby incorporated by reference in its entirety. Said ASCII copy, created on Mar. 4, 2013 (modified on Nov. 16, 2016), from U.S. application Ser. No. 13/822,942, is named "8219US05_SeqList" and is 108 kilobytes in size.

FIELD OF THE INVENTION

The present invention relates to modified coagulation factors. The present invention more specifically relates to modified coagulation factors having decreased cellular uptake resulting in a decreased rate of clearance/cellular uptake and/or reduced immunogenicity. The invention furthermore relates to use of such molecules as well as methods for producing such molecules.

BACKGROUND OF THE INVENTION

Haemophilia A is an inherited bleeding disorder caused by deficiency or dysfunction of coagulation factor VIII (FVIII) activity. The clinical manifestation is not on primary haemostasis as formation of the initial blood clot occurs normally. Rather the clot is unstable due to a lack of secondary thrombin formation and fibrin stabilization of the primary clot. The disease is treated by intravenous injection of FVIII which is either isolated from blood or produced recombinantly. Development of neutralizing antibodies (inhibitors) against FVIII occurs in approximately 20-40% of severe harmophilia A patients after FVIII administration, rendering further treatment with FVIII ineffective. Induction of inhibitors thus provides a major complication in haemophilia care. Current treatment recommendations are moving from traditional on-demand treatment towards prophylaxis. The circulatory half life of endogenous FVIII bound to von Willebrand Factor (vWF) is 12-14 hours and prophylactic treatment is thus to be performed several times a week in order to obtain a virtually symptom-free life for the patients. Intravenous administration is for many, especially children and young persons, associated with significant inconvenience and/or pain. Various methods have been employed in the development of a FVIII variant with significantly prolonged circulatory half life. A number of these methods relate to conjugation of FVIII with hydrophilic polymers such as e.g. PEG (poly ethylene glycol). WO03031464 discloses an enzymatic approach where PEG groups can be attached to glycans present on the polypeptide.

It has also been suggested to modulate low density lipoprotein receptor related protein (LRP) mediated clearance of FVIII in order to obtain a FVIII variant with a decreased rate of cellular uptake/clearance and thus an increased in vivo circulatory half life, but this approach has been hampered by the apparent massive redundancy of potential LRP binding sites present on the surface of FVIII and uncertainty on the role of these. Furthermore, some of these sites are in close vicinity to regions critical for FVIII:C activity, and a lowered LRP binding may be accompanied by a substantial loss of activity which makes the FVIII variant less attractive as a therapeutic agent. Interaction of LRP and related receptors with its ligands is thought to involve lysine residues on the surface of the ligand docking in an acidic "necklace" in the receptor (Mol Cell 2006; 22: 277-283). It has furthermore been suggested that hydrophobic residues, in combination with lysine residues, may be involved in interaction with LRP-family members (FEBS J 2006; 273: 5143-5159, J Mol Biol 2006; 362: 700-716) and it could therefore be speculated if modification of these hydrophobic residues, in addition to critical lysine residues or other positively charged residues, could result in decreased interaction with LRP family members and potentially prolonged and/or decreased clearance.

In order to be of therapeutic interest, FVIII variants should retain FVIII procoagulant function. It thus follows that there is a need in the art for specific FVIII variants with maintained FVIII activity and a significantly prolonged in vivo circulatory half life and/or reduced immunogenicity.

SUMMARY OF THE INVENTION

The present invention thus relates to a recombinant FVIII variant having FVIII activity, wherein said variant comprises a substitution of two, three, four, five, six, seven, eight, nine or ten surface accessible positively charged residues in FVIII C1 and/or C2 domains termed "C1 foot" and/or the "C2 foot", wherein said surface accessible positively charged amino acid residues, such as e.g. lysine, arginine, or histidine residues are substituted with, but not limited to, alanine or glutamine, and wherein the substitutions result in decreased cellular uptake. The present invention furthermore relates to a recombinant FVIII variant, wherein said FVIII variant comprises a K2092A substitution and a F2093A substitution, wherein said variant is conjugated with a half life extending moiety, such as e.g. PEG. The present invention also relates to a recombinant FVIII variant having FVIII activity, wherein said variant comprises a mutation that results in an additional glycosylation site, wherein the glycan in said glycosylation site confers a reduced ability to bind to the KM33 antibody.

The FVIII variants according to the present invention have a decreased cellular uptake associated with an increased circulatory half life. The FVIII variants according to the invention may furthermore have the advantage of having decreased LRP binding. The FVIII variants according to the invention may furthermore have the advantage of having reduced immunogenicity compared to FVIII molecules without this type of mutations. The explanation for the reduced immunogenicity may be that positively charged residues are substituted in the C1 and/or C2 feet of FVIII resulting in decreased uptake in cells responsible for presenting FVIII to the immune system.

DESCRIPTION OF THE INVENTION

Definitions

Factor VIII molecules: FVIII/Factor VIII is a large, complex glycoprotein that primarily is produced by hepatocytes. Human FVIII consists of 2351 amino acids, including signal peptide, and contains several distinct domains, as defined by homology. There are three A-domains, a unique B-domain, and two C-domains. The domain order can be listed as $NH_2$-A1-A2-B-A3-C1-C2-COOH. FVIII circulates in plasma as two chains, separated at the B-A3 border. The chains are connected by bivalent metal ion-bindings. The A1-A2-B chain is termed the heavy chain (HC) while the A3-C1-C2 is termed the light chain (LC).

Figure 1:
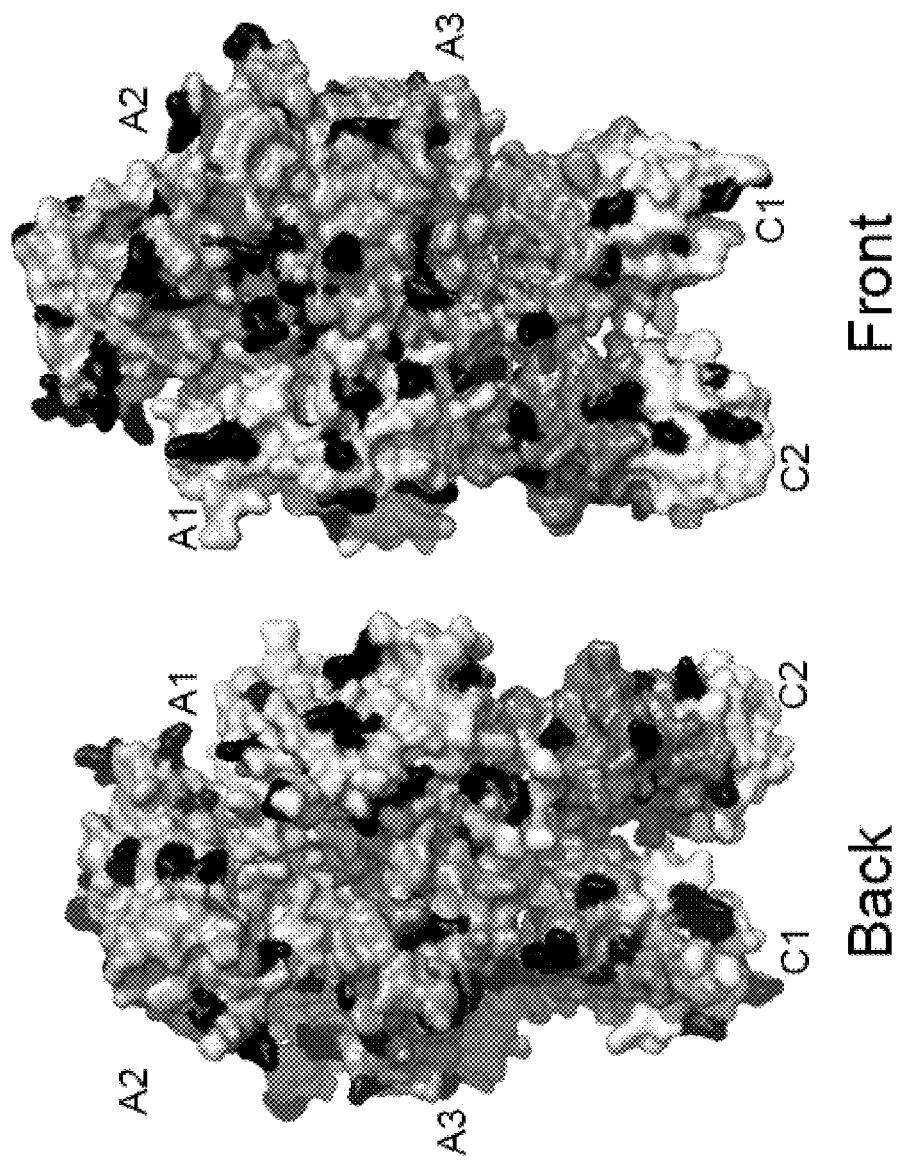
FIG. 1: Surface model of the x-ray crystallographic structure of FVIII (pdb entry code 3cdz) shown in front and back orientations. The positions of A1, A2, A3, C1 and C2 domains are indicated. Lysine and arginine residues are in black.

"C1 foot" and "C2 foot": In the context of the present invention, the "C1 foot" is defined as the region of the C1 domain that has the capacity of non-covalently anchoring the FVIII molecule/FVIII variant to anionic membranes comprising phosphatidyl-L-serine found e.g. on platelets. In FIG. 1 a surface model of the x-ray crystallographic structure of FVIII (pdb entry code 3cdz) is shown in front and back orientations. The positions of A1, A2, A3, C1 and C2 domains are indicated. Lysine and arginine residues are in black showing their wide distribution. The C1 foot is shown in white in the model of FVIII shown in FIG. 2. More specifically, the following C1 amino acids are likely anchored in the phospholipid membrane, in connection with e.g. platelet binding, and are thus a part of the C1 foot: 2029-2035+2043-2069+2090-2100+2130-2136+2156-2163. The inventors of the present invention have surprisingly shown that mutation of each of the 2065, 2090, and 2092 residues will result in biologically active FVIII variants having decreased LRP binding—in particular when these residues are substituted with, but not limited to, either a glutamine or an alanine residue, depending on the surface accessible area of the residue.

In the context of the present invention, the "C2 foot" is defined as the region of the C2 domain that likely has the capacity of anchoring the FVIII molecule/FVIII variant to anionic membranes comprising phosphatidyl-L-serine found e.g. on platelets. The C2 foot is shown in white in the model of FVIII shown in FIG. 2. More specifically, the following C2 amino acids are anchored in the phospholipid layer, in connection with e.g. platelet binding, and are thus a part of the C2 foot: 2195-2227+2248-2258+2287-2291+2313-2320. The inventors of the present invention have shown that mutation of one of the surface exposed lysine or arginine residues in the C2 foot (either R2215 or K2249) will result in biologically active FVIII variants having decreased LRP binding—in particular when these residues are substituted with, but not limited to, either a glutamine residue or an alanine residue, depending on the surface accessibility of the residue. The inventors have furthermore shown that a FVIII variant comprising both a substitution in the C1 foot and one in the C2 foot displays decreased LRP binding as well as maintained FVIII:C activity.

Surface accessible charged residue/positively charged residue/lysine or arginine residues in the FVIII C1 and/or the C2 foot: The accessible surface area (ASA) is the surface area of a biomolecule or parts of a biomolecular surface (e.g. a single amino acid side chain) that is accessible to a solvent. The ASA is usually quoted in square ångstrom (a standard unit of measurement in molecular biology). ASA was first described by Lee & Richards in 1971 and is sometimes called the Lee-Richards molecular surface [B. Lee and F. M. Richards, "The Interpretation of Protein Structures: Estimation of Static Accessibility" J. Mol. Biol. 55, 379-400 (1971)].

The surface accesibilities can be calculated with the computer program Quanta 2005 from Accelrys Inc. using the atomic coordinates originating from e.g. x-ray structures. The relative surface accessibility of an amino acid side chain is the actual surface accessible area divided by the maximum accessible surface area as determined for the single amino acid. The ASA is calculated from the x-ray crystallographic structure of FVIII with pdb entry code 3cdz. If the relative surface accessibility is less than 20%, the residue is mutated to glutamine in order to prevent local collapse of the protein surface. Charged surface accessible amino acid residues, preferably positively charged amino acid residues, preferably lysine and/or arginine residues in the C1 and/or C2 foot can thus be selected for amino acid substitution in order to arrive at a FVIII variant having decreased cellular uptake and optionally also decreased LRP binding/LRP mediated clearance.

"Factor VIII" or "FVIII" as used herein refers to a human plasma glycoprotein that is a member of the intrinsic coagulation pathway and is essential to blood coagulation. "Native FVIII" is the full length human FVIII molecule as shown in SEQ ID NO: 1 (amino acid 1-2332). The B-domain is spanning amino acids 741-1648 in SEQ ID NO: 1.

SEQ ID NO: 1 (wt human FVIII):
ATRRYYLGAVELSWDYMQSDLGELPVDARFPPRVPKSFPFNTSVVYKKTLFVEFTDHLF-

NIAKPRPPWMGLLGPTIQAEVYDTVVITLKNMASHPVSLHAVGVSYW-

KASEGAEYDDQTSQREKEDDKVFPGGSHTYVWQVLKENGPMASDPLCLTYSYLSH-

VDLVKDLNSGLIGALLVCREGSLAKEKTQTLHKFILLFAVFDEGKSWHSETKNSLMQDRDAA-

SARAWPKMHTVNGYVNRSLPGLIGCHRKSVYWHVIGMGTTPEVHSIFLEGHTFLVRNHR-

QASLEISPITFLTAQTLLMDLGQFLLFCHISSHQHDGMEAYVKVDSCPEEPQLRMKN-

NEEAEDYDDDLTDSEMDVVRFDDDNSPSFIQIRSVAKKHPKTWVHYIAAEEED-

WDYAPLVLAPDDRSYKSQYLNNGPQRIGRKYKKVRFMAYTDETFKTREAIQHESGILGPLLY-

GEVGDTLLIIFKNQASRPYNIYPHGITDVRPLYSRRL-

PKGVKHLKDFPILPGEIFKYKWTVTVEDGPTKSDPRCLTRYYSSFVNMERDLASGLIG-

PLLICYKESVDQRGNQIMSDKRNVILFSVFDENRSWYLTENIQRFLPNPAGVQLEDPEFQAS-

NIMHSINGYVFDSLQLSVCLHEVAYWYILSIGAQTDFLSVFFSGYTFKHKMVYEDTLTLF-

PFSGETVFMSMENPGLWILGCHNSDFRNRGMTALLKVSSCDKNTGDYYEDSYED-

ISAYLLSKNNAIEPRSFSQNSRHPSTRQKQFNATTIPENDIEKTDPWFAHRTPMP-

KIQNVSSSDLLMLLRQSPTPHGLSLSDLQEAKYETFSDDPSPGAIDSNNSLSEMTH-

FRPQLHHSGDMVFTPESGLQLRLNEKLGTTAATELKKLDFKVSSTSNN-

LISTIPSDNLAAGTDNTSSLGPPSMPVHYDSQLDTTLFGKKSSPLTESGG-

PLSLSEENNDSKLLESGLMNSQESS-

WGKNVSSTESGRLFKGKRAHGPALLTKDNALFKVSISLLKTNKTSNNSATNRKTHIDGPSLLIEN

SPSVWQNILESDTEFKKVTPLIHDRMLMDKNATALRLNHMSNKTTSSKNMEMVQQKKEG-

PIPPDAQNPDMSFFKMLFLPESARWIQRTHGKNSLNSGQGP-

SPKQLVSLGPEKSVEGQNFLSEKNKVVVGKGEFTKDVGLKEMVFPSSRNLFLTNLD-

NLHENNTHNQEKKIQEEIEKKETLIQENVVLPQIHTVTGTKNFMKNLFLLSTRQNVEGSYDGA-

YAPVLQDFRSLNDSTNRTKKHTAHFSKKGEEENLEGLGNQTKQIVEKYACTTRISP-

NTSQQNFVTQRSKRALKQFRLPLEETELEKRIIVDDTSTQWSKNMKHLTPSTLTQI-

DYNEKEKGAITQSPLSDCLTRSHSIPQANRSPLPIAKVSS-

FPSIRPIYLTRVLFQDNSSHLPAASYRK-

KDSGVQESSHFLQGAKKNNLSLAILTLEMTGDQREVGSLGTSATNSVTYKKVENTVLPKPDLP

KTSGKVELLPKVHIYQKDLFPTETSNGSPGHLDLVEGSLLQGTEGAIK-

WNEANRPGKVPFLRVATESSAKTPSKLLDPLAWDNHYGTQIPKEEWKSQEKSPEKTAF-

KKKDTILSLNACESNHAIAAINEGQNKPEIEVTWAKQGRTERLCSQNPPVLKRHQREITRT-

TLQSDQEEIDYDDTISVEMKKEDFDIYDEDENQSPRSFQKKTRHYFI-

AAVERLWDYGMSSSPHVLRNRAQSGSVPQFKKVVFQEFTDGSFTQPLYRGELNEH-

LGLLGPYIRAEVEDNIMVTFRNQASRPYSFYSSLISYEEDQRQGAEPRKNFVKPNETK-

TYFWKVQHHMAPTKDEFDCKAWAYFSDVDLEKDVHSGLIG-

PLLVCHTNTLNPAHGRQVTVQEFALFFTIFDETKSVVYFTENMERN-

CRAPCNIQMEDPTFKENYRFHAINGYIMDTLPGLVMAQDQRIRWYLLSMGSNE-

NIHSIHFSGHVFTVRKKEEYKMALYNLYPGVFETVEM-

LPSKAGIWRVECLIGEHLHAGMSTLFLVYSNKCQTPLGMASGHIRDFQITASGQYGQWAP-

KLARLHYSGSINAWSTKEPFSWIKVDLLAPMIIHGIKTQGARQKFSSLYISQFIIMYSLD-

```
-continued
GKKWQTYRGNSTGTLMVFFGNVDSSGIKHNIFNPPIIARYIRLHPTHYSIRSTLR-

MELMGCDLNSCSMPLGMESKAISDAQITASSYFTNMFAT-

WSPSKARLHLQGRSNAWRPQVNNPKEWLQVDFQKTMKVTGVTTQGVKSLLTSMYVKE-

FLISSSQDGHQWTLFFQNGKVKVFQGNQDSFTPVVNSLDPPLLTRYLRI-

HPQSWVHQIALRMEVLGCEAQDLY
```

The FVIII molecules/variants according to the present invention may be B domain deleted or B domain truncated FVIII molecules wherein the remaining domains correspond closely to the sequence as set forth in amino acid no 1-740 and 1649-2332 in SEQ ID NO: 1. However, B domain truncated molecules according to the invention may differ slight from the sequence set forth in SEQ ID NO: 1, meaning that the remaining domains (i.e. the three A-domains and the two C-domains) may differ slightly e.g. 1, 2, 3, 4, 5, 6, 7, 8, 9, 10, 11, 12, 13, 14, 15, 16, 17, 18, 19, or 20 amino acids from the amino acid sequence as set forth in SEQ ID NO: 1 (amino acids 1-740 and 1649-2332) due to the fact that mutations can be introduced in order to e.g. reduce vWF binding capacity. Furthermore, one or two amino acid substitutions are introduced in the C1 and/or the C2 foot in order to modify the binding capacity of FVIII for LRP. It is, however, possible that the FVIII variants according to the present invention furthermore comprise lysine substitutions in other places on the surface of the molecule in order to further modify LRP binding. Additional amino acid substitutions, deletions, or additions may also be introduced in order to modulate the properties of the FVIII variant according to the invention. Finally, amino acid substitutions may be introduced in the FVIII variants according to the present invention in order to increase the intramolecular stability of the molecule.

FVIII molecules according to the present invention have FVIII activity also termed FVIII:C or FVIII:C activity, meaning the ability to function in the coagulation cascade in a manner functionally similar or equivalent to FVIII, induce the formation of FXa via interaction with FIXa on an activated platelet, and support the formation of a blood clot. The activity can be assessed in vitro by techniques well known in the art such as e.g. measurement of FX activation in a chromogenic assay, clot analysis using FVIII-deficient plasma, thrombin generation assays, thromboelastography etc. FVIII molecules according to the present invention have FVIII activity being at least about 10%, at least 20%, at least 30%, at least 40%, at least 50%, at least 60%, at least 70%, at least 80%, at least 90%, and 100% or even more than 100% of that of native human FVIII.

Intramolecular stability of FVIII (intrinsic stability): The "intrinsic stability" of FVIII variants according to the invention may sometimes be referred to as the "stability", the "physical stability", the "inherent stability", the "structural stability", the "chemical stability", "intrinsic stability", the "in vitro stability", the "thermodynamic stability", the "thermal stability", the "folding stability" etc. and depends on environmental conditions in a complex way. The common theme for such terms is that they refer to the in vitro stability of the polypeptide and this in vitro stability can be seen as the sum of the forces in the polypeptide that stabilize the relatively small ensemble of folded conformations. There are significant differences between FVIII in vivo stability and in vitro stability because FVIII is subject to a large number of clearance mechanisms in vivo. It has thus far not been possible to obtain a prolonged in vivo circulatory half life with FVIII variants having improved in vitro stability. The in vitro stability of the FVIII variants according to the invention can be improved by e.g. insertion of stabilizing disulfide bridges, insertion of additional hydrophobic amino acids that can form intramolecular hydrophobic interactions, insertion of positive and negative amino acids that will form electrostatic interactions, etc.

Conjugation of FVIII with various side chains is known in the art as a mean for obtaining a prolonged circulatory half life of FVIII. It has previously been demonstrated that circulatory half-life can be increased approximately 2-fold, i.e., to about 24 hours, by e.g. conjugation of the FVIII molecule. The intrinsic stability of wt FVIII, as determined by a half-life in TAP/hirudin anti-coagulated plasma at 37° C. is about 30 hours which coincides with the longest circulatory half life reported for a FVIII variant.

There may however be an unexpected synergy effect in the combination of C1 and/or C2 foot lysine or arginine substitutions with e.g. increasing the in vitro stability of FVIII and/or e.g. conjugating the FVIII variant with a side chain. An additional surprising synergy effect that may be obtained with molecules according to the present invention is that the resulting FVIII variants may furthermore posses a significantly increased specific activity resulting in a more potent molecule.

B domain truncated/deleted FVIII molecule: The B domain in FVIII spans amino acids 741-1648 in SEQ ID NO: 1. The B domain is cleaved at several different sites, generating large heterogeneity in circulating plasma FVIII molecules. The exact function of the heavily glycosylated B domain is unknown. What is known is that the domain is dispensable for FVIII activity in the coagulation cascade. Recombinant FVIII is thus frequently produced in the form of B domain deleted/truncated variants.

Endogenous full length FVIII is synthesized as a single-chain precursor molecule. Prior to secretion, the precursor is cleaved into the heavy chain and the light chain. Recombinant B domain-deleted FVIII can be produced from two different strategies. Either the heavy chain without the B domain and the light chain are synthesized individually as two different polypeptide chains (two-chain strategy) or the B domain deleted FVIII is synthesized as a single precursor polypeptide chain (single-chain strategy) that is cleaved into the heavy and light chains in the same way as the full-length FVIII precursor.

In a B domain-deleted FVIII precursor polypeptide prepared by the single-chain strategy, the heavy and light chain moieties are normally separated by a linker. To minimize the risk of introducing immunogenic epitopes in the B domain-deleted FVIII, the sequence of the linker is preferable derived from the FVIII B domain. As a minimum, the linker must comprise a recognition site for the protease that cleaves the B domain-deleted FVIII precursor polypeptide into the heavy and light chain. In the B domain of full length FVIII, amino acid 1644-1648 constitutes this recognition site. The thrombin site leading to removal of the linker on activation of B domain-deleted FVIII is located in the heavy chain.

Thus, the size and amino acid sequence of the linker is unlikely to influence its removal from the remaining FVIII molecule by thrombin activation. Deletion of the B domain is an advantage for production of FVIII. Nevertheless, parts of the B domain can be included in the linker without reducing the productivity. The negative effect of the B domain on productivity has not been attributed to any specific size or sequence of the B domain. According to a preferred embodiment, the truncated B domain comprises only one potential 0-glycosylation sites and one or more side groups/moieties are covalently conjugated to this 0-glycosylation site, preferably via a linker.

The O-linked oligosaccharides in the B-domain truncated molecules according to the invention may be attached to O-glycosylation sites that were either artificially created by recombinant means and/or by generation of new O-glycosylation sites by truncation of the B domain. An example of a truncated 0-glycosylated FVIII B domain is: SFSQN-SRHPSQNPPVLKRHQR (SEQ ID NO: 2). Such molecules may be made by designing a B domain trunctated FVIII amino acid sequence and subsequently subjecting the amino acid sequence to an in silico analysis predicting the probability of O-glycosylation sites in the truncated B domain. Molecules with a relatively high probability of having such glycosylation sites can be synthesized in a suitable host cell followed by analysis of the glycosylation pattern and subsequent selection of molecules having O-linked glycosylation in the truncated B domain.

The FVIII molecule also contains a number of N-linked oligosaccharides and each of these may potentially serve as an anchor for attachment of a half life extending side group/moiety.

The maximal length of the B domain in the wt FVIII molecule is about 907 amino acids. The length of the truncated B domain in molecules according to the present invention may vary from about 10 to about 800 amino acids, such as e.g. from about 10 amino acids to about 700 acids, such as e.g. about 12-500 amino acids, 12-400 amino acids, 12-300 amino acids, 12-200 amino acids, 15-100 amino acids, 15-75 amino acids, 15-50 amino acids, 15-45 amino acids, 20-45 amino acids, 20-40 amino acids, or 20-30 amino acids. The truncated B domain may comprise fragments of the heavy chain and/or the light chain and/or an artificially introduced sequence that is not found in the wt FVIII molecule. The terms "B-domain truncated" and "B-domain deleted" may be used interchangeably herein.

Modified circulatory half life: Molecules according to the present invention may have a modified in vivo circulatory half life compared to the wild type FVIII molecule, preferably an increased circulatory half life. Circulatory half life is preferably increased at least 10%, preferably at least 15%, preferably at least 20%, preferably at least 25%, preferably at least 30%, preferably at least 35%, preferably at least 40%, preferably at least 45%, preferably at least 50%, preferably at least 55%, preferably at least 60%, preferably at least 65%, preferably at least 70%, preferably at least 75%, preferably at least 80%, preferably at least 85%, preferably at least 90%, preferably at least 95%, preferably at least 100%, more preferably at least 125%, more preferably at least 150%, more preferably at least 175%, more preferably at least 200%, and most preferably at least 250% or 300%. Even more preferably, such molecules have a circulatory half life that is increased at least 400%, 500%, 600%, or even 700%. The following method for measuring in vivo circulatory half life can be used: FVIII is administered intravenously to FVIII deficient mice e.g. FVIII exon 16 knock out (KO) mice with c57bl/6 background bread at Taconic M&B, or vWF-deficient mice e.g. vWF exon 4+5 KO mice with mixed SV129 and c57bl/6 background bred at Charles River, Germany. The vWF-KO mice had 13% of normal FVIII:C, while the FVIII-KO mice had no detectable FVIII:C. The mice receive a single intravenous injection of rFVIII (280 IU/kg) in the tail vein. Blood are taken from the orbital plexus at time points up to 64 hours after dosing using non-coated capillary glass tubes. Three samples are taken from each mouse, and 2 to 4 samples are collected at each time point. Blood are immediately stabilized with sodium citrate and diluted in four volumes buffer (50 mM Tris, 150 mM NaCl, 1% BSA, pH 7.3, with preservative) before 5 min centrifugation at 4000×g. Plasma obtained from diluted blood are frozen on dry ice and kept at −80° C. The FVIII:C are determined in a chromogenic assay essentially as described in example 3. FVIII antigen can be measured by ELISA e.g. Asserachrom® VIIIC:Ag from Diagnostica Stago. Pharmacokinetic analysis can be carried out by e.g. non-compartmental methods (NCA) using winnonlin pro version 4.1 software.

Antibodies: The term "antibody" herein refers to a protein, derived from a germline immunoglobulin sequence, capable of specifically binding to an antigen or a portion thereof. The term includes full length antibodies of any isotype (that is, IgA, IgE, IgG, IgM and/or IgY) and any single chain thereof. The site on the antiben to which an antibody binds is called the epitope. Full-length antibodies usually comprise at least four polypeptide chains: that is, two heavy (H) chains and two light (L) chains that are interconnected by disulfide bonds. The antibody can be dissected into the antigen binding Fab fragments and the Fc domain which binds to various Fc receptors. "Single-chain Fv" or "scFv" antibody fragments comprise the VH and VL domains of an antibody, where these domains are present in a single polypeptide chain.

Immunogenicity of FVIII: Patients with severe hemophilia A have less than 1% FVIII and their immune system may therefore respond to therapeutic FVIII administration as a foreign antigen, in particular in connection with high intensity treatment following major bleedings. Neutralizing antibodies to FVIII (inhibitors) typically map to certain areas within the A2 domain and the light chain, in particular the C2 domain (J Thromb Haemost 2004; 2:1082-1095; Blood 2007; 110: 4234-4242). Uptake by dendritic cells and macrophages is believed to be the initial step in presenting FVIII to the immune system in (J Thromb Haemost 2009; 7: 1816-1823).

Macrophage mannose receptors have been suggested to be involved in FVIII uptake by these antigen presenting cells (Proc Natl Acad Sci USA 2007; 104: 8965-8970) while LRP appears not to be involved (Haematologica 2008; 93: 83-89). The subsequent development of inhibitors is a T-cell dependent immune response. A single CD4+ T-cell epitope has been identified and confirmed within a peptide spanning amino acid 2098-2112 in the C1 domain while no other 15-mer peptides spanning the entire A1-A2-A3-C1-C2 domains were confirmed positive (J Thromb Haemost 2005; 3: 991-1000). Mutations of two amino acids in the peptide, i.e. M2104 and L2107, resulted in decreased T-cell proliferation. In another study, T cell epitopes were analysed within the A2, C1 and C2 domains and amino acid residues R2220, F2196, N2198, M2199, L2200 and R2215 in C2 were found to be of particular importance for eliciting a T-cell response (WO 2011/060372). Also a B-cell epitope in the A2 domain may have a role in generation of an immune response as FVIII-R484A/R489A/P492A induced lower level of inhibitory anti FVIII antibodies in a haemophilia A mice model than wt FVIII (Blood 2004; 104: 704-710). It thus follows that different investigators have identified different epitopes in FVIII to be involved in the immune response to FVIII, and that there is no common agreement on where in FVIII to introduce substitutions in order to generate a less immunogenic FVIII molecule. Immunogenicity of FVIII is typically assessed in hemophilia A mice models carrying the native murine (Thromb Haemost 1999; 81: 240-244) or (part of) the humane MHC class II repetoire (Haemophilia 2010; 16 suppl 5: 47-53), in animal models where tolerance to human FVIII has been induced (Haemophilia 2010; 16 suppl 5: 47-53), or in human T-cell response assays (Thromb Haemost 2000; 84: 643-652; WO 2011/060372), although it is not known if any of these models are predictive for the human clinic.

Cellular uptake/LRP mediated clearance of FVIII: FVIII variants according to the invention preferably have a decreased cellular uptake. A decreased cellular uptake may be associated with a prolonged in vivo circulatory half life. Cellular uptake can be measured using the assay disclosed in example 7. LRP and LRP family members have been implicated in FVIII clearance via endocytosis of FVIII by LRP expressing cells on the surface of e.g. hepatocytes. Infusion of an LRP antagonist RAP (receptor-associated protein) in mice completely inhibited the initial phase of FVIII clearance in BALB/c mice and prolonged the half life of $^{125}$I-FVIII 3.3-fold (J Biol Chem 1999; 274: 37685-37692). In conditional LRP deficient mice was an enhanced plasma level of FVIII observed (Blood 2003; 101: 3933-3939) and in a combined LRP and LDLR (low density lipoprotein receptor)-deficient mice has a 4.8-fold enhanced mean residence time of infused FVIII been demonstrated (Blood 2005; 106: 906-912). While these publications demonstrate a role of LRP and LRP family members in clearance of FVIII in vivo, the exact positions in FVIII responsible for interaction with LRP remain unclear. An LRP binding site comprising amino acid 484-509 has previously been identified in A2 (J Biol Chem 1999; 274: 37685-37692; Biochemistry 2006; 45: 1829-1840; Blood Coagul Fibronolysis 2008; 19: 543-555). However, mAb413 binding to this region only affected LRP binding to isolated A2 and not intact FVIII most likely as the LRP site in A2 is only exposed in activated FVIII (FVIIIa) (J Thromb Heamost 2006; 4: 1487-1493). Furthermore FVIII with single or multiple alanine substitutions within amino acid 376-556 showed LRP binding comparable to FVIII without substitutions in this region, and plasma residence time in mice of the mutated FVIII molecules was not increased relative to the half-life of wild-type FVIII (abstract P-T-035, ISTH 2007). LRP binding sites has been suggested to exist in the light chain of FVIII (J Biol Chem 1999; 274: 23734-23739, WO 00/28021) and a site involving Glu1811-Lys1818 in the A3 domain was identified based on an inhibitory effect of an antibody as well as synthetic peptides covering this region and the lack of LRP binding of FVIII-FV chimeras where this region in FVIII was replaced with the corresponding sequence in FV (J Biol Chem 2003; 278: 9370-9377). This region is in close vicinity or overlapping with a factor IXa interaction site, and consequently mutations within this site may affect the cofactor activity of FVIII. In addition, a site in the C2 domain has been suggested based on the ability of the anti C2 mAb ESH4 to inhibit LRP binding of FVIII (J Biol Chem 1999; 274: 23734-23739). Several epitopes for ESH4 within the C2 domain of FVIII have been suggested. An epitope for ESH4 within amino acid 2248-2285 is noted in J Biol Chem 1997; 272: 18007-18014) while 2173-2222 was later identified as essential for the binding of ESH4 to FVIII (Thromb Haemost 2003; 89: 795-802). In the data sheet of the antibody (American Diagnostica) and in J Mol Recognit 2009; 22: 301-306 an epitope within 2303-2322 of FVIII is noted. Therefore the data available for the localization of the epitope of ESH4 on FVIII are conflicting and not sufficiently detailed to allow prediction of the individual amino acid(s) essential for LRP binding. In addition, even at high concentration of C2 (500 nM) only a modest association with LRP was observed (J Biol Chem 1999; 274: 23734-23739) suggesting that the affinity of the LRP site in C2 is low and rendering it unclear if this site plays any dominant role in intact FVIII. A major phospholipid binding site is present in the C2 domain of FVIIIa. This was originally identified due to the ability of synthetic peptides spanning the C2 domain to inhibit FVIII binding to immobilized phosphatidyl serine (Blood 1990; 75: 1999-2004). By this way residues 2303-2332 were suggested to mediate phospholipid binding. In addition, the monoclonal antibody ESH-8 reduced the affinity of FVIIIa to phospholipid vesicles containing phosphatidyl-L-serine (Blood 1995; 86: 1811-1819; J Biol Chem 1998; 273: 27918-27926). The epitope of ESH8 includes amino acid 2248-2285 (Blood 1995; 86: 1811-1819). However, in a later publication, ESH8 and a peptide consisting of amino acid 2248-2285 failed to inhibit FVIIIa binding to activated platelets, while the ESH4 antibody and a peptide covering amino acid 2303-2332 inhibited FVIIIa binding to the activated platelets (Biochemistry 2005; 44: 13858-13865).

Thus, while it has long been speculated in the art that FVIII variants having a decreased LRP binding could potentially have an increased in vivo circulatory half life, no specific LRP binding sites in the C1 and C2 domains of FVIII resulting in prolonged circulatory half life have been identified so far.

LRP binding motifs are thought to involve paired lysine residues with a distance of about 20 Å each docking into an "acidic necklace" (Mol Cell 2006; 22: 277-286). The distance between LRP binding sites may however be deviating somewhat from the 20 Å (e.g. at least 15 Å) due to the flexibility in the amino acid side chains, flexibility in the FVIII structure, etc. Like-wise, the distance between two LRP binding sites may also be about 40 Å, 60 Å or even 80 Å.

Arginine may substitute lysine as the side chain of arginine is more bulky that of lysine and may not fit into the acidic necklace, thus decrease LRP binding. FVIII comprises a large number of potential LRP binding motifs, i.e. the inventors of the present invention have defined 140 surface exposed lysine or arginine (FIG. 1 and table 1). It thus follows that a person skilled in the art would not be able to identify FVIII variants with one, two, three, or only a limited number of substitutions with substantially reduced LRP binding. Additionally, the person skilled in the art could expect that a large number of lysine and/or arginine residues should be mutated in order to significantly reduce LRP binding and LRP-mediated clearance of FVIII. A large number of lysine and/or arginine substitutions, in order to reduce LRP binding, would most likely result in a molecule that either have little or no biological activity and/or a molecule that cannot be expressed in sufficient amounts. This is exemplified by several of the FVIII mutants shown in table 1. The inventors of the present invention have, however, surprisingly shown that substitution of a surface accessible lysine or arginine residue in either the C1 or the C2 foot, or with a substitution in both the C1 and the C2 foot of FVIII, results in a FVIII variant having significant reduced LRP binding while retaining full activity.

Uptake of FVIII by antigen presenting cells such as dendritic cells and macrophages bypasses the LRP receptor family (Haematologica 2008; 93: 83-98). Instead macrophage mannose receptor binding to high mannose glycans has been implicated in uptake of FVIII by these cells (Proc Natl Acad Sci USA 2007; 104: 8965-8970). The inventors of the present invention have, however, shown that FVIII mutations resulting in decreased binding to LRP also shows decreased uptake in dendritic cells and macrophages. In a murine model of antibody formation to human FVIII, these substitutions in FVIII surprisingly resulted in lower level of total anti FVIII antibodies as well as neutralising antibodies (inhibitors) as measured in the Bethesda assay generally used to monitor development of inhibitors in haemophilia patients. It may therefore be speculated if the FVIII variants with decreased cellular uptake could have a therapeutic benefit in regard to lower risk for developing inhibitors.

FVIII mutations suitable for modulating LRP binding/cellular uptake: It is known in the art that the KM33 antibody has the capacity of inhibiting FVIII binding to LRP (J Biol Chem 2003; 278: 9370-9377 and WO 03/093313). Co-administration of KM33 scFv with FVIII to vWF deficient mice resulted in higher level of FVIII activity 15 and 30 min after administration as compared to control mice receiving only FVIII (WO 03/093313). As KM33 binds the K2092-S2094 region (Blood 2009; 114: 3938-3946 and abstract P-M-040, presented at ISTH, 2007), it has been suggested that K2092 might constitute part of one potential LRP binding site. which may further comprise K2065 (abstract O-M-041 presented at ISTH, 2007). These single substitutions both affected LRP binding but not the interaction with factor IXa (abstract O-M-041, ISTH, 2007). It has, however, not been suggested that substitution of only two or more (up to about ten) of these amino acid residues with alanine would significantly decrease LRP binding and/or cellular uptake.

FVIII variants comprising a K2092A substitution and/or a F2093A substitution are disclosed in Blood 2009; 114: 3938-3946. These mutations were found to have a 3-10 fold reduction in affinity to membranes comprising 4% phosphatidyl-L-serine and a more than 95% reduction of factor Xase activity at low phosphatidyl-L-serine level e.g. 4%.

Considering the large redundancy of potential LRP binding sites and the fact that only a few amino acid substitutions of surface exposed lysine (or arginine) residues can be performed without loosing biological activity and/or significantly reducing the FVIII yield it has thus far not been possible to provide biologically active FVIII variants having one or two or a few amino acid substitutions resulting in a significantly decreased LRP binding. The inventors of the present invention did, however, arrive at selecting amino acid substitutions in the C1 and/or the C2 foot of FVIII that did both retain biological activity as well as showing a significant reduction in LRP binding (table 1 and 2). It was not expected that combination of substitutions within LRP sites in the C1 foot with substitutions within sites in the C2 foot would result in FVIII molecules with a larger effect on LRP binding and the these FVIII molecules at the same time maintain FVIII:C, as the sites are in close vicinity to phospholipid binding sites.

Examples of FVIII variants having modulated LRP binding/cellular uptake according to the present invention include:

```
K2092A                                                          (SEQ ID NO: 3)

atrryylgavelswdymqsdlgelpvdarfpprvpksfpfntsvvykktlfveftdhlfniakprppwmgllgptiqaevydtvvitlknmashpvslhavgvsywkasegaeyddqtsqrekeddkvfpggshtyvwqvlkengpmasdplcltysylshvdlvkdlnsgligallvcregslakektqtlhkfillfavfdegkswhsetknslmqdrdaasarawpkmmhtvngyvnrslpgligchrksvywhvigmgttpevhsifleghtflvrnhrqasleispitfltaqtllmdlgqfllfchisshqhdgmeayvkvdscpeepqlrmknneeaedydddltdsemdvvrfdddnspsfiqirsvakkhpktwvhyiaaeeedwdyaplvlapddrsyksqylnngpqrigrkykkvrfmaytdetfktreaighesgilgpllygevgdtlliifknqasrpyniyphgitdvrplysrrlpkgvkhlkdfpilpgeifkykwtvtvedgptksdprcltryyssfvnmerdlasgligpkgvkhlkdfpilpgeifkykwtvtvedgptksdprcltryyssfvnmerdlasgligpllicykesvdqrgnqimsdkrnvilfsvfdenrswylteniqrflpnpagvqledpefqasnimhsingyvfdslqlsvclhevaywyilsigaqtdflsvffsgytfkhkmvyedtltlfpfsgetvfmsmenpglwilgchnsdfrnrgmtallkvsscdkntgdyyedsyedisayllsknnaieprsfsqnppvlkrhqreitrttlqsdqeeidyddtisvemkkedfdiydedenqsprsfqkktrhyfiaaverlwdygmsssphvlrnraqsgsvpqfkkvvfqeftdgsftqplyrgelnehlgllgpyiraevednimvtfrnqasrpysfysslisyeedqrqgaeprknfvkpnetktyfwkvqhhmaptkdefdckawayfsdvdlekdvhsgligpllychtntlnpahgrqvtvqefalfftifdetkswyftenmerncrapcniqmedptfkenyrfhaingyimdtlpglvmaqdqrirwyllsmgsne-
```

-continued nihsihfsghvftvrkkeeykmalynlypgvfetvemlpskagiwrvecligehlhagmstlflvysnkcqtplgmasghirdfqitasgqygqwapklarlhysgsinawstkepfswikvdllapmiihgiktqgarqafsslyisqfiimysldgkkwqtyrgnstgtlmvffgnvdssgikhnifnppiiaryirlhpthysirstlrmelmgcdlnscsmplgmeskaisdaqitassyftnmfatwspskarlhlqgrsnawrpqvnnpkewlqvdfqktmkvtgvttqgvkslltsmyvkeflisssqdghqwtlffqngkvkvfqgnqdsftpvvnsldpplltrylrihpqswvhqialrmevlgceaqdly

F2093A
(SEQ ID NO: 4)

atrryylgavelswdymqsdlgelpvdarfpprvpksfpfntsvvykktlfveftdhlfniakprppwmgllgptiqaevydtvvitlknmashpvslhavgvsywkasegaeyddqtsqrekeddkvfpggshtyvwqvlkengpmasdplcltysylshvdlvkdlnsgligallvcregslakektqtlhkfillfavfdegkswhsetknslmqdrdaasarawpkmhtvngyvnrslpgligchrksvywhvigmgttpevhsifleghtflvrnhrqasleispitfltaqtllmdlgqfllfchisshqhdgmeayvkvdscpeepqlrmknneeaedydddltdsemdvvrfdddnspsfiqirsvakkhpktwvhyiaaeeedwdyaplvlapddrsyksqylnngpqrigrkykkvrfmaytdetfktreaighesgilgpllygevgdtlliifknqasrpyniyphgitdvrplysrrlpkgvkhlkdfpilpgeifkykwtvtvedgptksdprcltryyssfvnmerdlasgligpkgvkhlkdfpilpgeifkykwtvtvedgptksdprcltryyssfvnmerdlasgligpllicykesvdqrgnqimsdkrnvilfsvfdenrswylteniqrflpnpagvqledpefqasnimhsingyvfdslqlsvclhevaywyilsigaqtdflsvffsgytfkhkmvyedtltlfpfsgetvfmsmenpglwilgchnsdfrnrgmtallkvsscdkntgdyyedsyedisaylsknnaieprsfsqnppvlkrhqreitrttlqsdqeeidyddtisvemkkedfdiydedenqsprsfqkktrhyfiaaverlwdygmsssphvlrnraqsgsvpqfkkvvfqeftdgsftqplyrgelnehlgllgpyiraevednimvtfrnqasrpysfysslisyeedqrqgaeprknfvkpnetktyfwkvqhhmaptkdefdckawayfsdvdlekdvhsgligpllvchtntlnpahgrqvtvqefalfftifdetkswyftenmerncrapcniqmedptfkenyrfhaingyimdtlpglvmaqdqrirwyllsmgsnenihsihfsghvftvrkkeeykmalynlypgvfetvemlpskagiwrvecligehlhagmstlflvysnkcqtplgmasghirdfqitasgqygqwapklarlhysgsinawstkepfswikvdllapmiihgiktqgarqkasslyisqfiimysldgkkwqtyrgnstgtlmvffgnvdssgikhnifnppiiaryirlhpthysirstlrmelmgcdlnscsmplgmeskaisdaqitassyftnmfatwspskarlhlqgrsnawrpqvnnpkewlqvdfqktmkvtgvttqgvkslltsmyvkeflisssqdghqwtlffqngkvkvfqgnqdsftpvvnsldpplltrylrihpqswvhqialrmevlgceaqdly

K2092A-F2093A
(SEQ ID NO: 5)

atrryylgavelswdymqsdlgelpvdarfpprvpksfpfntsvvykktlfveftdhlfniakprppwmgllgptiqaevydtvvitlknmashpvslhavgvsywkasegaeyddqtsqrekeddkvfpggshtyvwqvlkengpmasdplcltysylshvdlvkdlnsgligallvcregslakektqtlhkfillfavfdegkswhsetknslmqdrdaasarawpkmhtvngyvnrslpgligchrksvywhvigmgttpevhsifleghtflvrnhrqasleispitfltaqtllmdlgqfllfchisshqhdgmeayvkvdscpeepqlrmkn- -continued neeaedydddltdsemdvvrfdddnspsfiqirsvakkhpktwvhyiaaeeedwdyaplvlapddrsyksqylnngpqrigrkykkvrfmaytdetfktreaiqhesgilgpllygevgdtlliifknqasrpyniyphgitdvrplysrrlpkgvkhlkdfpilpgeifkykwtvtvedgptksdprcltryyssfvnmerdlasgligpkgvkhlkdfpilpgeifkykwtvtvedgptksdprcltryyssfvnmerdlasgligpllicykesvdqrgnqimsdkrnvilfsvfdenrswylteniqrflpnpagvqledpefqasnimhsingyvfdslqlsvclhevaywyilsigaqtdflsvffsgytfkhkmvyedtltlfpfsgetvfmsmenpglwilgchnsdfrnrgmtallkvsscdkntgdyyedsyedisayllsknnaieprsfsqnppvlkrhqreitrtttlqsdqeeidyddtisvemkkedfdiydedenqsprsfqkktrhyfiaaverlwdygmsssphvlrnraqsgsvpqfkkvvfqeftdgsftqplyrgelnehlgllgpyiraevednimvtfrnqasrpysfysslisyeedqrqgaeprknfvkpnetktyfwkvqhhmaptkdefdckawayfsdvdlekdvhsgligpllvchtntlnpahgrqvtvqefalfftifdetkswyftenmerncrapcniqmedptfkenyrfhaingyimdtlpglvmaqdqrirwyllsmgsnenihsihfsghvftvrkkeeykmalynlypgvfetvemlpskagiwrvecligehlhagmstlflvysnkcqtplgmasghirdfqitasgqygqwapklarlhysgsinawstkepfswikvdllapmiihgiktqgarqaasslyisqfiimysldgkkwqtyrgnstgtlmvffgnvdssgikhnifnppiiaryirlhpthysirstlrmelmgcdlnscsmplgmeskaisdaqitassyftnmfatwspskarlhlqgrsnawrpqvnnpkewlqvdfqktmkvtgvttqgvkslltsmyvkeflissssqdghqwtlffqngkvkvfqgnqdsftpvvnsldpplltrylrihpqswvhqialrmevlgceaqdly

R2215A (SEQ ID NO: 6)

atrryylgavelswdymqsdlgelpvdarfpprvpksfpfntsvvykktlfveftdhlfniakprppwmgllgptiqaevydtvvitlknmashpvslhavgvsywkasegaeyddqtsqrekeddkvfpggshtyvwqvlkengpmasdplcltysylshvdlvkdlnsgligallvcregslakektqtlhkfilllfavfdegkswhsetknslmqdrdaasarawpkmhtvngyvnrslpgligchrksvywhvigmgttpevhsifleghtflvrnhrqasleispitfltaqtllmdlgqfllfchisshqhdgmeayvkvdscpeepqlrmknneeaedydddltdsemdvvrfdddnspsfiqirsvakkhpktwvhyiaaeeedwdyaplvlapddrsyksqylnngpqrigrkykkvrfmaytdetfktreaiqhesgilgpllygevgdtlliifknqasrpyniyphgitdvrplysrrlpkgvkhlkdfpilpgeifkykwtvtvedgptksdprcltryyssfvnmerdlasgligpkgvkhlkdfpilpgeifkykwtvtvedgptksdprcltryyssfvnmerdlasgligpllicykesvdqrgnqimsdkrnvilfsvfdenrswylteniqrflpnpagvqledpefqasnimhsingyvfdslqlsvclhevaywyilsigaqtdflsvffsgytfkhkmvyedtltlfpfsgetvfmsmenpglwilgchnsdfrnrgmtallkvsscdkntgdyyedsyedisayllsknnaieprsfsqnsrhpseqkliseedlsqnppvlkrhqreitrtttlqsdqeeidyddtisvemkkedfdiydedenqsprsfqkktrhyfiaaverlwdygmsssphvlrnraqsgsvpqfkkvvfqeftdgsftqplyrgelnehraqsgsvpqfkkvvfqeftdgsftqplyrgelnehlgllgpyiraevednimvtfrnqasrpysfysslisyeedqrqgaeprknfvkpnetktyfwkvqhhmaptkdefdckawayfsdvdlekdvhsgligpllvchtntlnpahgrqvtvqefalfftifdetkswyftenmerncrapcniqmedptfkenyrfhaingyimdtlpglvmaqdqrirwyllsmgsnenihsihfsghvftvrkkeeykmalynlypgvfetvem- -continued lpskagiwrvecligehlhagmstlflvysnkcqtplgmasghirdfqitasgqygqwapklarlhysgsinawstkepfswikvdllapmiihgiktqgarqkfsslyisqfiimysldgkkwqtyrgnstgtlmvffgnvdssgikhnifnppiiaryirlhpthysirstlrmelmgcdlnscsmplgmeskaisdaqitassyftnmfatwspskarlhlqgasnawrpqvnnpkewlqvdfqktmkvtgvttqgvkslltsmyvkeflisssqdghqwtlffqngkvkvfqgnqdsftpvvnsldpplltrylrihpqswvhqialrmevlgceaqdly

K2065A-R2215A (SEQ ID NO: 7)

atrryylgavelswdymqsdlgelpvdarfpprvpksfpfntsvvykktlfveftdhlfniakprppwmgllgptiqaevydtvvitlknmashpvslhavgvsywkasegaeyddqtsqrekeddkvfpggshtyvwqvlkengpmasdplcltysylshvdlvkdlnsgligallvcregslakektqtlhkfillfavfdegkswhsetknslmqdrdaasarawpkmhtvngyvnrslpgligchrksvywhvigmgttpevhsifleghtflvrnhrqasleispitfltaqtllmdlgqfllfchisshqhdgmeayvkvdscpeepqlrmknneeaedydddltdsemdvvrfdddnspsfiqirsvakkhpktwvhyiaaeeedwdyaplvlapddrsyksqylnngpqrigrkykkvrfmaytdetfktreaiqhesgilplllygevgdtlliifknqasrpyniyphgitdvrplysrrlpkgvkhlkdfpilpgeifkykwtvtvedgptksdprcltryyssfvnmerdlasgligpkgvkhlkdfpilpgeifkykwtvtvedgptksdprcltryyssfvnmerdlasgligpllicykesvdqrgnqimsdkrnvilfsvfdenrswylteniqrflpnpagvqledpefqasnimhsingyvfdslqlsvclhevaywyilsigaqtdflsvffsgytfkhkmvyedtltlfpfsgetvfmsmenpglwilgchnsdfrnrgmtallkvsscdkntgdyyedsyedisayllsknnaieprsfsqnsrhpseqkliseedlsqnppvlkrhqreitrttlqsdqeeidyddtisvemkkedfdiydedenqsprsfqkktrhyfiaaverlwdygmsssphvlrnraqsgsvpqfkkvvfqeftdgsftqplyrgelnehraqsgsvpqfkkvvfqeftdgsftqplyrgelnehlgllgpyiraevednimvtfrnqasrpysfyssllisyeedqrqgaeprknfvkpnetktyfwkvqhhmaptkdefdckawayfsdvdlekdvhsgligpllvchtntlnpahgrqvtvqefalfftifdetkswyftenmerncrapcniqmedptfkenyrfhaingyimdtlpglvmaqdqrirwyllsmgsnenihsihfsghvftvrkkeeykmalynlypgvfetvemlpskagiwrvecligehlhagmstlflvysnkcqtplgmasghirdfqitasgqygqwapklarlhysgsinawstaepfswikvdllapmiihgiktqgarqkfsslyisqfiimysldgkkwqtyrgnstgtlmvffgnvdssgikhnifnppiiaryirlhpthysirstlrmelmgcdlnscsmplgmeskaisdaqitassyftnmfatwspskarlhlqgasnawrpqvnnpkewlqvdfqktmkvtgvttqgvkslltsmyvkeflisssqdghqwtlffqngkvkvfqgnqdsftpvvnsldpplltrylrihpqswvhqialrmevlgceaqdly

R2090A-R2215A (SEQ ID NO: 8)

atrryylgavelswdymqsdlgelpvdarfpprvpksfpfntsvvykktlfveftdhlfniakprppwmgllgptiqaevydtvvitlknmashpvslhavgvsywkasegaeyddqtsqrekeddkvfpggshtyvwqvlkengpmasdplcltysylshvdlvkdlnsgligallvcregslakektqtlhkfillfavfdegkswhsetknslmqdrdaasarawpkmhtvngyvnrslpgligchrksvywhvigmgttpevhsifleghtflvrnhrqasleispitfltaqtllmdlgqfllfchisshqhdgmeayvkvdscpeepqlrmknneeaedydddltdsemdvvrfdddnspsfiqirsvakkhpktwvhyiaaeeed- -continued

```
wdyaplvlapddrsyksqylnngpqrigrkykkvrfmaytdetfktreaighesgilgplly-
gevgdtlliifknqasrpyniyphgitdvrplysrrlpkgvkhlkdfpilpgeifkykwtvtvedgptksdprcltryyssfvnmerdlasglig-
pkgvkhlkdfpilpgeifkykwtvtvedgptksdprcltryyssfvnmerdlasglig-
pllicykesvdqrgnqimsdkrnvilfsvfdenrswylteniqrflpnpagvqledpefqas-
nimhsingyvfdslqlsvclhevaywyilsigaqtdflsvffsgytfkhkmvyedtltlf-
pfsgetvfmsmenpglwilgchnsdfrnrgmtallkvsscdkntgdyyedsyedisayllskn-
naieprsfsqnsrhpseqkliseedlsqnppvlkrhqreitrtt1qsdqeeidyddtis-
vemkkedfdiydedenqsprsfqkktrhyfiaaverlwdygmsssphvlrnraqsgsvpqfkkvvfqeftdgsftqplyrgelneh-
raqsgsvpqfkkvvfqeftdgsftqplyrgelneh-
lgllgpyiraevednimvtfrnqasrpysfysslisyeedqrqgaeprknfvkpnetk-
tyfwkvqhhmaptkdefdckawayfsdvdlekdvhsgligpllvchtntlnpahgrqvtvqe-
falfftifdetkswyftenmerncrapcniqmedptfkenyrfhaingyim-
dtlpglvmaqdqrirwyllsmgsnenihsihfsghvftvrkkeeykmalynlypgvfetvem-
lpskagiwrvecligehlhagmstlflvysnkcqtplgmasghirdfqitasgqygqwap-
klarlhysgsinawstkepfswikvdllapmiihgiktqgaaqkfsslyisqfiimysld-
gkkwqtyrgnstgtlmvffgnvdssgikhnifnppiiaryirlhpthysirstlr-
melmgcdlnscsmplgmeskaisdaqitassyftnmfatwspskarlhlqgasnawrpqvnnp-
kewlqvdfqktmkvtgvttqgvkslltsmyvkeflisss-
qdghqwtlffqngkvkvfqgnqdsftpvvnsldpplltrylrihpqswvhqialrmevlgceaqdly
K2092A-R2215A                                                                    (SEQ ID NO: 9)
atrryylgavelswdymqsdlgelpvdarfpprvpksfpfntsvvykktlfveftdhlf-
niakprppwmgllgptiqaevydtvvitlknmashpvslhavgvsyw-
kasegaeyddqtsqrekeddkvfpggshtyvwqvlkengpmasdplcltysylsh-
vdlvkdlnsgligallvcregslakektqtlhkfilllfavfdegkswhsetknslmqdrdaa-
sarawpkmhtvngyvnrslpgligchrksvywhvigmgttpevhsifleghtflvrnhr-
qasleispitfltaqtllmdlgqfllfchisshqhdgmeayvkvdscpeepqlrmkn-
neeaedydddltdsemdvvrfdddnspsfiqirsvakkhpktwvhyiaaeeed-
wdyaplvlapddrsyksqylnngpqrigrkykkvrfmaytdetfktreaighesgilgplly-
gevgdtlliifknqasrpyniyphgitdvrplysrrlpkgvkhlkdfpilpgeifkykwtvtvedgptksdprcltryyssfvnmerdlasglig-
pkgvkhlkdfpilpgeifkykwtvtvedgptksdprcltryyssfvnmerdlasglig-
pllicykesvdqrgnqimsdkrnvilfsvfdenrswylteniqrflpnpagvqledpefqas-
nimhsingyvfdslqlsvclhevaywyilsigaqtdflsvffsgytfkhkmvyedtltlf-
pfsgetvfmsmenpglwilgchnsdfrnrgmtallkvsscdkntgdyyedsyedisayllskn-
naieprsfsqnsrhpseqkliseedlsqnppvlkrhqreitrtt1qsdqeeidyddtis-
vemkkedfdiydedenqsprsfqkktrhyfiaaverlwdygmsssphvlrnraqsgsvpqfkkvvfqeftdgsftqplyrgelneh-
raqsgsvpqfkkvvfqeftdgsftqplyrgelneh-
lgllgpyiraevednimvtfrnqasrpysfysslisyeedqrqgaeprknfvkpnetk-
tyfwkvqhhmaptkdefdckawayfsdvdlekdvhsgligpllvchtntlnpahgrqvtvqe-
falfftifdetkswyftenmerncrapcniqmedptfkenyrfhaingyim-
dtlpglvmaqdqrirwyllsmgsnenihsihfsghvftvrkkeeykmalynlypgvfetvem-
lpskagiwrvecligehlhagmstlflvysnkcqtplgmasghirdfqitasgqygqwap-
```

-continued
klarlhysgsinawstkepfswikvdllapmiihgiktqgarqafsslyisqfiimysldgkkwqtyrgnstgtlmvffgnvdssgikhnifnppiiaryirlhpthysirstlrmelmgcdlnscsmplgmeskaisdaqitassyftnmfatwspskarlhlqgasnawrpqvnnpkewlqvdfqktmkvtgvttqgvkslltsmyvkeflisssqdghqwtlffqngkvkvfqgnqdsftpvvnsldpplltrylrihpqswvhqialrmevlgceaqdly Side chain/side group/moiety: FVIII variants according to the present invention may be covalently conjugated with a (half life extending) side group/moiety either via post-translational modification or in the form of a fusion protein. One or more of the following side group modifications of FVIII may thus be carried out: alkylation, acylation, ester formation, di-sulfide or amide formation or the like. This includes PEGylated FVIII, cysteine-PEGylated FVIII and variants thereof. The FVIII variants according to the invention may also be conjugated to biocompatible fatty acids and derivatives thereof, hydrophilic polymers (Hydroxy Ethyl Starch, Poly Ethylene Glycol, hyaluronic acid, heparosan polymers, Phosphorylcholine-based polymers, fleximers, dextran, poly-sialic acids), polypeptides (antibodies, antigen binding fragments of antibodies, Fc domains, transferrin, albumin, Elastin like peptides (MacEwan S R, Chilkoti A. Biopolymers. 2010; 94:60), XTEN polymers (Schellenberger V et al. Nat Biotechnol. 2009; 27:1186), PASylation or HAPylation (Schlapschy M et al. Protein Eng Des Sel. 2007; 20:273), Albumin binding peptides (Dennis M S et al. J Biol Chem. 2002, 277:35035)), etc.

FVIII according to the present invention may be acylated by one or more half life extending hydrophobic side groups/moieties—optionally via a linker. Compounds having a $—(CH_2)_{12}—$ moiety are possible albumin binders in the context of the present invention. Hydrophobic side groups may sometimes be referred to as "albumin binders" due to the fact that such side groups may be capable of forming non-covalent complexes with albumin, thereby promoting the circulation of the acylated FVIII variant in the blood stream, due to the fact that the complexes of the acylated FVIII variant and albumin is only slowly disintegrated to release the FVIII variant. FVIII can be acylated using chemical methods as well as enzymatic "glyco-acylation" methods essentially following the processes as disclosed in WO03031464. Enzymatic methods have the advantages of avoiding use of any organic solvents as well as being very site specific in general.

The term "PEGylated FVIII" means FVIII, conjugated with a PEG molecule. It is to be understood, that the PEG molecule may be attached to any part of FVIII including any amino acid residue or carbohydrate moiety. The term "cysteine-PEGylated FVIII" means FVIII having a PEG molecule conjugated to a sulfhydryl group of a cysteine introduced in FVIII. PEG is a suitable polymer molecule, since it has only few reactive groups capable of cross-linking compared to polysaccharides such as dextran. In particular, monofunctional PEG, e.g. methoxypolyethylene glycol (mPEG), is of interest since its coupling chemistry is relatively simple (only one reactive group is available for conjugating with attachment groups on the polypeptide). Consequently, the risk of cross-linking is eliminated, the resulting polypeptide conjugates are more homogeneous and the reaction of the polymer molecules with the polypeptide is easier to control.

To effect covalent attachment of the polymer molecule(s) to the polypeptide, the hydroxyl end groups of the polymer molecule are provided in activated form, i.e. with reactive functional groups. The PEGylation may be directed towards conjugation to all available attachment groups on the polypeptide (i.e. such attachment groups that are exposed at the surface of the polypeptide) or may be directed towards one or more specific attachment groups, e.g. the N-terminal amino group (U.S. Pat. No. 5,985,265), N- and/or O-linked glycans, etc. Furthermore, the conjugation may be achieved in one step or in a stepwise manner (e.g. as described in WO 99/55377). An enzymatic approach for coupling side groups/moieties to 0- and/or N-linked glycans is disclosed in WO03031464.

Fusion protein: Fusion proteins/chimeric proteins, are proteins created through the joining of two or more genes which originally coded for separate proteins. Translation of this fusion gene results in a single polypeptide with functional properties derived from each of the original proteins. The side chain of the FVIII variants according to the present invention may thus be in the form of a polypeptide fused to FVIII. FVIII according to the present invention may thus be fused to peptides that can confer a prolonged half life to the FVIII such as e.g. antibodies and "Fc fusion derivatives" or "Fc fusion proteins".

Fc fusion protein is herein meant to encompass FVIII fused to an Fc domain that can be derived from any antibody isotype, although an IgG Fc domain will often be preferred due to the relatively long circulatory half life of IgG antibodies. The Fc domain may furthermore be modified in order to modulate certain effector functions such as e.g. complement binding and/or binding to certain Fc receptors. Fusion of FVIII with an Fc domain, having the capacity to bind to FcRn receptors, will generally result in a prolonged circulatory half life of the fusion protein compared to the half life of the wt FVIII protein. Mutations in positions 234, 235 and 237 in an IgG Fc domain will generally result in reduced binding to the FcγRI receptor and possibly also the FcγRIIa and the FcγRIII receptors. These mutations do not alter binding to the FcRn receptor, which promotes a long circulatory half life by an endocytic recycling pathway. Preferably, a modified IgG Fc domain of a fusion protein according to the invention comprises one or more of the following mutations that will result in decreased affinity to certain Fc receptors (L234A, L235E, and G237A) and in reduced C1q-mediated complement fixation (A330S and P331S), respectively.

Von Willebrand Factor (vWF): vWF is a large mono-/multimeric glycoprotein present in blood plasma and produced constitutively in endothelium (in the Weibel-Palade bodies), megakaryocytes (a-granules of platelets), and subendothelial connective tissue. Its primary function is binding to other proteins, particularly FVIII and it is important in platelet adhesion to wound sites.

FVIII is bound to vWF while inactive in circulation; FVIII degrades rapidly or is cleared when not bound to vWF. It thus follows that reduction or abolishment of vWF binding capacity in FVIII would be considered as a highly undesirable approach in obtaining FVIII variants with prolonged circulatory half life. It may however be possible to reduce or abolish vWF by site directed mutagenesis if the molecule is conjugated to a protective half life extending side group/moiety. The region in FVIII responsible for binding to vWF is the region spanning residues 1670-1684 as disclosed in EP0319315. It is envisaged that FVIII point and/or deletion mutants involving this area will modify the ability to bind to vWF. Examples of particularly preferred point mutations according to the present invention include variants comprising one or more of the following point mutations: Y1680F, Y1680R, Y1680N-E1682T, and Y1680C.

Glycoprotein: The term "glycoprotein" is intended to encompass peptides, oligopeptides and polypeptides containing one or more oligosaccharides (glycans) attached to one or more amino acid residues of the "back bone" amino acid sequence. The glycans may be N-linked or O-linked.

The term "terminal sialic acid" or, interchangeable, "terminal neuraminic acid" is thus intended to encompass sialic acid residues linked as the terminal sugar residue in a glycan, or oligosaccharide chain, i.e., the terminal sugar of each antenna is N-acetylneuraminic acid linked to galactose via an α2->3 or α2->6 linkage.

The term "galactose or derivative thereof" means a galactose residue, such as natural D-galactose or a derivative thereof, such as an N-acetylgalactosamine residue.

The term "terminal galactose or derivative thereof" means the galactose or derivative thereof linked as the terminal sugar residue in a glycan, or oligosaccharide chain, e.g., the terminal sugar of each antenna is galactose or N-acetylgalactosamine.

The term "asialo glycoprotein" is intended to include glycoproteins wherein one or more terminal sialic acid residues have been removed, e.g., by treatment with a sialidase or by chemical treatment, exposing at least one galactose or N-acetylgalactosamine residue from the underlying "layer" of galactose or N-acetylgalactosamine ("exposed galactose residue"). In general, N-linked glycans, which are not part of wild type FVIII, can be introduced into the FVIII molecules of the invention, by introducing amino acid mutations so as to obtain N-X-S/T motifs. The FVIII molecules of the present invention contain 1, 2, 3, 4, 5, 6, 7, 8, 9, or 10, or more, N-linked glycans. The structure of N-linked glycans are of the high-mannose or complex form. High mannose glycans contain terminal mannose residues at the non-reducing end of the glycan. Complex N-glycans contain terminal sialic acid, galactose or N-acetylglucosamine at the non-reducing end. N-linked glycosylation sites can thus be inserted into the FVIII variants according to the present invention using recombinant techniques.

Sialyltransferase: Sialyltransferases are enzymes that transfer a sialic acid to nascent oligosaccharide. Each sialyltransferase is specific for a particular sugar nucleotide donor substrate. Sialyltransferases add sialic acid to the terminal galactose in glycolipids (gangliosides), or N- or O-linked glycans of glycoproteins. Sialyltransferase is suitable for use in enzymatic conjugation of side groups/moieties to glycans present on the FVIII molecule.

Pharmaceutical composition: A pharmaceutical composition is herein preferably meant to encompass compositions comprising FVIII molecules according to the present invention suitable for parenteral administration, such as e.g. ready-to-use sterile aqueous compositions or dry sterile compositions that can be reconstituted in e.g. water or an aqueous buffer. The compositions according to the invention may comprise various pharmaceutically acceptable excipients, stabilizers, etc.

Additional ingredients in such compositions may include wetting agents, emulsifiers, antioxidants, bulking agents, tonicity modifiers, chelating agents, metal ions, oleaginous vehicles, proteins (e.g., human serum albumin, gelatine or proteins) and a zwitterion (e.g., an amino acid such as betaine, taurine, arginine, glycine, lysine and histidine). Such additional ingredients, of course, should not adversely affect the overall stability of the pharmaceutical formulation of the present invention. Parenteral administration may be performed by subcutaneous, intramuscular, intraperitoneal or intravenous injection by means of a syringe, optionally a pen-like syringe. Alternatively, parenteral administration can be performed by means of an infusion pump.

Suitable host cells for producing recombinant FVIII protein according to the invention are preferably of mammalian origin in order to ensure that the molecule is properly processed during folding and post-translational modification, e.g. glycosylation, sulfatation, etc. In practicing the present invention, the cells are mammalian cells, more preferably an established mammalian cell line, including, without limitation, CHO, COS-1, baby hamster kidney (BHK), and HEK293 cell lines. A preferred BHK cell line is the tk-ts13 BHK cell line, hereinafter referred to as BHK 570 cells. A preferred CHO cell line is the CHO K1 cell line as well as cell lines CHO-DXB11 and CHO-DG44. Other suitable cell lines include, without limitation, Rat Hep I, Rat Hep II, TCMK, NCTC 1469; DUKX cells (CHO cell line), and DG44 (CHO cell line). Also useful are 3T3 cells, Namalwa cells, myelomas and fusions of myelomas with other cells. Currently preferred cells are HEK293, COS, Chinese Hamster Ovary (CHO) cells, Baby Hamster Kidney (BHK) and myeloma cells, in particular Chinese Hamster Ovary (CHO) cells.

The term "treatment", as used herein, refers to the medical therapy of any human or other animal subject in need thereof. Said subject is expected to have undergone physical ex-amination by a medical practitioner, who has given a tentative or definitive diagnosis which would indicate that the use of said specific treatment is beneficial to the health of said human or other animal subject. The timing and purpose of said treatment may vary from one individual to another, according to the status quo of the subject's health. Thus, said treatment may be prophylactic, palliative, symptomatic and/or curative.

In a first aspect, the present invention thus relates to a recombinant FVIII variant having FVIII activity, wherein said variant comprises 2-10, alternatively 2-8, alternatively 2-7, alternatively 2-6, alternatively 2-5, alternatively 2-4, such as two, three, four, five, six, seven, eight, nine, or ten substitutions of surface accessible positively charged amino acids, e.g. lysine and/or arginine residues, in the FVIII C1 foot and/or the C2 foot, wherein said surface accessible positively charged residue/lysine or arginine residues are substituted with, but not limited to, alanine or glutamine, and wherein the substitutions results in decreased LRP binding and preferably also in reduced cellular uptake. In one embodiment, the surface accessible charged amino acid is selected from the group consisting of: lysine, arginine, and histidine. Preferably, said variant furthermore has decreased LRP binding. Preferably, said variant furthermore has decreased immunogenicity and/or reduced clearance. Most preferably, said variant has reduced cellular uptake, decreased LRP binding and decreased immunogenicity and reduced clearance. According to one specific embodiment, one or more arginine residues may substitute one or more lysine residues. The "bulky" side chain of arginine may not be able to dock properly into the acidic necklage of LRP thus resulting in decreased LRP binding. In one embodiment, said FVIII variant furthermore comprises e.g. the R2159N mutation and/or other mutations that result in formation of an additional glycosylation site, wherein the glycan in said glycosylation site confers a reduced ability to bind to the KM33 antibody.

In a second aspect, the present invention relates to a recombinant FVIII variant, wherein said variant comprises a K2092A substitution and a F2093A substitution, wherein said variant is conjugated with a half life extending moiety. The half life extending moiety can be e.g. one or more PEG moieties, one or more PSA moieties, one or more HES moieties, one or more fatty acids/fatty acid derivatives, an Fc domain, or a combination of any of these (e.g. one or more PEG moieties combined with one or more PSA moieties). In one embodiment, said FVIII variant furthermore comprises the R2159N mutation and/or other mutations that result in formation of an additional glycosylation site, wherein the glycan in said glycosylation site confers a reduced ability to bind to the KM33 antibody.

In a third aspect, the present invention relates to a recombinant FVIII variant having FVIII activity, wherein said variant comprises a mutation that results in an additional glycosylation site, wherein the glycan in said glycosylation site confers a reduced ability to bind to the KM33 antibody. Preferably, the reduced ability to bind the KM33 antibody results in decreased cellular uptake and/or decreased LRP binding. One example of this type of FVIII variants comprising an additional glycosylation site that confers reduced ability of the variant to bind to the KM33 antibody is a FVIII variant comprising the R2159N mutation.

In one embodiment, the FVIII variant according to the invention comprises 2-10, alternatively 2-9, alternatively 2-8, alternatively 2-7, alternatively 2-6, alternatively 2-5, alternatively 2-4, such as e.g. two, three, four, five, six, seven, eight, nine or ten substitutions of surface accessible positively charged amino acid residues in the FVIII C1 foot and/or the C2 foot, wherein said surface accessible charged amino acid residues are substituted with alanine or glutamine and wherein the substitutions result in decreased cellular uptake of said FVIII variant.

In one embodiment, the FVIII variant according to the invention furthermore comprises the F2093A mutation.

According to one embodiment, the FVIII variant according to the invention comprises at least two substitutions of surface accessible positively charged amino acid residues in the C1 foot. In another embodiment, the FVIII variant according to the invention comprises at least two substitutions of surface accessible positively charged amino acid residues in the C2 foot. In another embodiment, the FVIII variant according to the invention comprises at least one substitution of a surface accessible positively charged amino residue in the C1 foot and at least one substitution of a surface accessible charged amino acid residue in the C2 foot.

According to another embodiment, the FVIII variant according to the invention comprises a pair of substitutions of surface accessible positively charged amino acid residues, wherein the distance between the pair of substitutions is at least 15 Å.

In another embodiment, the FVIII variant according to the invention comprises a substitution of K2092. Preferably, the 2092 lysine residue is substituted with an alanine residue. Alternatively, the 2092 lysine residue is substituted with a glutamine residue.

In another embodiment the FVIII variant according to the invention comprises said K2092 substitution and a substitution of R2215. Preferably, the 2092 lysine residue is substituted with an alanine residue. Alternatively, the 2092 lysine residue is substituted with a glutamine residue. Preferably, the 2215 arginine residue is substituted with an alanine residue. Alternatively, the 2215 arginine residue is substituted with a glutamine residue.

In another embodiment, the FVIII variant according to the invention, said K2092 substitution is combined with a substitution of K2249. Preferably, the 2092 lysine residue is substituted with an alanine residue. Alternatively, the 2092 lysine residue is substituted with a glutamine residue. Preferably, the 2249 lysine residue is substituted with an alanine residue. Alternatively, the 2249 lysine residue is substituted with a glutamine residue.

In another embodiment, the FVIII variant according to the invention comprises a substitution of R2090. Preferably, the 2090 arginine residue is substituted with an alanine residue. Alternatively, the 2090 arginine residue is substituted with a glutamine residue.

In another embodiment, the FVIII variant according to the invention comprises a substitution of K2065. Preferably, the 2065 lysine residue is substituted with an alanine residue. Alternatively, the 2065 lysine residue is substituted with a glutamine residue.

In another embodiment, the FVIII variant according to the invention comprises said K2065 substitution and a substitution of R2215. Preferably, the 2065 lysine residue is substituted with an alanine residue. Alternatively, the 2065 lysine residue is substituted with a glutamine residue. Preferably, the 2215 arginine residue is substituted with an alanine residue. Alternatively, the 2215 arginine residue is substituted with a glutamine residue.

In another embodiment, the FVIII variant according to the invention comprises said K2065 substitution and a substitution of K2249. Preferably, the 2065 lysine residue is substituted with an alanine residue. Alternatively, the 2065 lysine residue is substituted with a glutamine residue. Preferably, the 2249 lysine residue is substituted with an alanine residue. Alternatively, the 2249 lysine residue is substituted with a glutamine residue.

According to a first embodiment, the FVIII variant according to the invention comprises a lysine or arginine substitution in the C2 foot, wherein said substitution is selected from one or more amino acids from the group consisting of: R2215, R2220, K2249, and K2320.

According to a second embodiment, the FVIII variant according to the invention comprises a lysine or arginine substitution in the C1 foot, wherein said substitution is selected from one or more amino acids from the group consisting of: K2065, R2090 and K2092.

In a second aspect, the present invention relates to a recombinant FVIII variant having FVIII activity, wherein said variant comprises a F2093A substitution in the C1 foot, and wherein the substitution results in decreased cell binding and/or cellular uptake and/or reduced LRP binding.

In one embodiment, the FVIII variant according to the invention is a FVIII variant conjugated to a half life extending side group/moiety. In another embodiment, the side groups can be conjugated to FVIII via a glycan, e.g. an N-linked glycan or an O-linked glycan. In a preferred embodiment, the side group is conjugated to FVIII glycans using an enzymatic approach as disclosed in e.g. WO03031464. In another preferred embodiment, N- and/or O-linked glycans may be introduced/added to the FVIII variant according to the invention using recombinant methods. In another embodiment, the FVIII variant according to the invention is a fusion protein, such as e.g. a FVIII:Fc fusion protein.

In another embodiment, the FVIII variant according to the invention furthermore comprises amino acid alterations that have been introduced in said FVIII variant in order to increase the in vitro stability of the variant. In a preferred embodiment, a disulfide bridge has been introduced in order to increase the in vitro stability of the FVIII variant according to the invention. According to another embodiment, said FVIII variant according the invention comprises one or more stabilizing disulfide bridge. Said stabilizing sulphur bridges are preferably covalently linking two domains of the FVIII variant according to the invention.

In another embodiment, the FVIII variant according to the invention is a B domain truncated variant. In another embodiment, the FVIII variant according to the invention comprises a half life extending side group/moiety and this side group is preferably is linked to an O-glycan situated in the truncated B-domain, and wherein said half life extending moiety is removed upon activation of said FVIII variant. According to a preferred embodiment the variant comprises an amino acid sequence selected from the group consisting of: SEQ ID NO: 3, SEQ ID NO: 4, SEQ ID NO: 5, SEQ ID NO: 6, SEQ ID NO: 7, SEQ ID NO: 8, and SEQ ID NO: 9.

In another embodiment the FVIII variant according to the invention comprises a half life extending side group/moiety selected from the group consisting of a PEG group, a Fc domain, a polypeptide, and a hydrophobic side group/moiety. In a preferred embodiment, the side group is in the form of a fusion partner fused to said FVIII variant. In a preferred embodiment, the Fc domain is an IgG Fc domain having reduced effector functions, preferably comprising the following amino acid substitutions: L234A, L235E, G237A, A330S, and P331S. In one embodiment, the side groups can be conjugated to the FVIII variant according to the invention using the "glycoPEGylation" enzymatic methods disclosed in e.g. WO03031464. In another embodiment, side groups can be added to the FVIII variant according to the invention via free introduced cysteine amino acid residues.

In another embodiment, the recombinant FVIII variant according to the invention comprises the following substitutions: K2092A and F2093A. This variant is preferably conjugated to one or more half life extending moieties such as e.g. PEG, HES, poly sialic acid (PSA), and a fatty acid/fatty acid derivative, HAS.

In another embodiment, the recombinant FVIII variant according to the invention comprises the following substitutions: R2090A, K2092A, and F2093A.

In another embodiment, the recombinant FVIII variant according to the invention comprises the following substitutions: K2065A, K2092A, F2093A, and R2215A.

In another embodiment, the recombinant FVIII variant according to the invention comprises the K2092A and F2093A substitutions combined with at least one of the substitutions selected from the list consisting of: R2215A, K2065A, and R2090A In another embodiment, the variant according to the invention comprises a substitution of at least one of the surface exposed amino acids bound by a FVIII antibody having the ability to reduce cellular uptake upon binding to FVIII.

In another embodiment, the variant according to the invention is a B domain truncated variant, wherein the sequence of the B domain is as set forth in SEQ ID NO: 2.

In another embodiment, the recombinant FVIII variant according to the invention comprises a substitution of at least one of the surface exposed amino acids bound by at least one FVIII antibody having the ability to reduce cellular uptake upon binding to FVIII. Examples of antibodies of this type include the KM33 (J Biol Chem 2003; 278: 9370-9377 and WO 03/093313), ESH4 (J Biol Chem 1997), CLB-CAg117 Blood 1998; 91: 2347-2352), 4F30 and 4F161 antibodies.

A second aspect relates to DNA molecules encoding the FVIII variants according to the invention as well as expression vectors and host cells comprising such DNA molecules.

A third aspect relates to methods of making FVIII variants according to the invention. Said methods comprise incubating an appropriate host cell under appropriate conditions and subsequently isolating said FVIII variant. The recombinantly produced variant may furthermore be conjugated with e.g. a side chain, preferably using an enzymatic approach.

A fourth aspect relates to a pharmaceutical composition comprising a FVIII variant according to the invention. A fifth aspect relates to a kit comprising a pharmaceutical composition comprising a FVIII variant according to the invention. The kit preferably comprises a container comprising a dry fraction comprising the FVIII variant according to the invention as well as a container comprising the buffer used for reconstituting the FVIII variant.

A sixth aspect relates to use of FVIII variant according to the invention or a pharmaceutical composition according to the invention for treatment of haemophilia, preferably haemophilia A. The present invention furthermore relates to use of a FVIII variant according to the invention for manufacturing a medicament for treating haemophilia, preferably haemophilia A.

A final aspect relates to a method of treatment of haemophilia comprising administering to a person in need thereof a therapeutically efficient amount of a FVIII variant or a pharmaceutical formulation according to the invention.

EXAMPLES

Example 1: Generation of FVIII Variants

A fragment encoding the cMyc tag was inserted in the C-terminus of the heavy chain in the expression construct encoding FVIII with a 21 amino acid B domain linker (Haemophilia 2010; 16: 349-48). The expression level and activity of this FVIII-cMyc2 were similar to un-tagged FVIII. FVIII-cMyc2 was used as template for the variants and as control in the assays described in example 3-5. Additional restriction sites were added to the FVIII-cMyc2 expression construct to ease swapping of domains among variants. The A1 domain is flanked by SalI and PshAI/MfeI, A2 is flanked by PshAI/MfeI and AvrII/NruI, A3 is flanked by AgeI/MiuI and BstZ17I/BstAPI, C1 by BstZ17I/BstAPI and SwaI/SphI and C2 by SwaI/SphI and SfiI. The site-directed mutagenesis of exposed basic amino acids (lysine or arginine) was conducted by Geneart AG (Regensburg, Germany).

Figure 2:
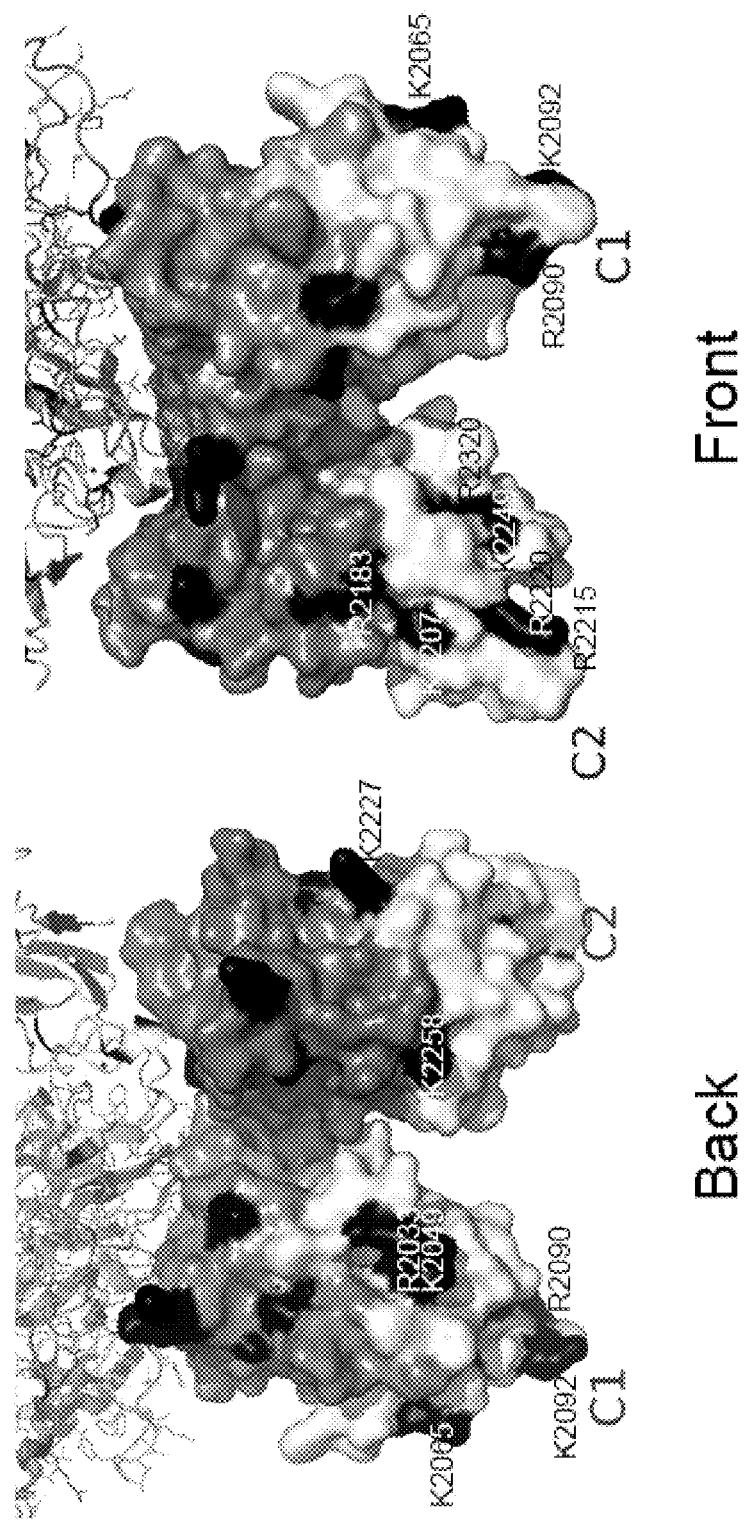
FIG. 2: Surface model of the x-ray crystallographic structure of FVIII (pdb entry code 3cdz) highlighting FVIII's C1 and C2 domains. The lower part of the C1 and C2 domains are in white depicting their putative membrane binding regions denoted the C1 foot and C2 foot, respectively. Lysine and arginine residues are in black.

Mutants with reduced affinity to LRP1 were localized to especially the feets of the C1 and C2 domains (see FIG. 2 and table 1 and 2). Combinations of C1 and C2 mutants were cloned by transferring 520 by SphI/SfiI fragments of R2215A, R2220Q, K2249A and R2320Q to the C1 mutants K2065A, R2090A and K2092A (table 2).

Example 2: Expression of the FVIII Mutants

Serum free transfection was performed using HKB11 cells (Cho M-S et al. J Biomed Sci 2002; 9: 631-63) and 293fectin (Invitrogen) following the manufacturer's recommendations. HKB11 suspension cells were grown in commercial FREESTYLE™ 293 Expression Medium (Invitrogen #. 12338-018) supplemented with 50 U mL$^{-1}$ penicillin and 50 ug mL$^{-1}$ streptomycin. Cells were grown as suspension cells in shakers and incubated at 37° C. under 5% $CO_2$ and 95% relative humidity. Cells were seeded at a density of $3 \times 10^5$ cells mL$^{-1}$ and passaged every 3 to 4 days. Viable and total cell concentrations were evaluated by Cedex (Innovatis) analysis using image analysis software for automated cell counting. Viable cells were highlighted by their ability to exclude the dye trypan blue. Cells were harvested 96 hours after transfection and the cell pellet isolated by gentle centrifugation. Afterwards, the cell pellet was re-suspended in the FREESTYLE™ 293 Expression medium containing 0.5 M NaCl. Following gentle centrifugation, the FVIII containing supernatants were harvested and stored at −80° C. until further analysis.

Example 3: FVIII:C Measured in Chromogenic Assay

The FVIII activity (FVIII:C) of the rFVIII compound was evaluated in a chromogenic FVIII assay using Coatest SP reagents (Chromogenix) as follows: FVIII samples and a FVIII standard (human calibration plasma, Chromogenix) were diluted in Coatest assay buffer (50 mM TRIS, 150 mM NaCl, 1% BSA, pH 7.3, with preservative). Fifty μL of samples (culture supernatant or purified FVIII variants) pre-diluted 100-, 400-, 1600- and 6400-fold, standards and buffer negative control were added to 96-well Spectramax® microtiter plates in duplicates. The factor IXa/factor X reagent, the phospholipid reagent and $CaCl_2$ from the Coatest SP kit were mixed 5:1:3 (vol:vol:vol) and 75 μL of this added to the wells. After 15 min incubation at room temperature 50 μL of the factor Xa substrate S-2765/thrombin inhibitor I-2581 mix was added and the reactions incubated 5 min at room temperature before 25 μL 1 M citric acid, pH 3, was added. The absorbance at 405 nm was measured on an Envision plate reader (PerkinElmer) with absorbance at 620 nm used as reference wavelength. The value for the negative control was subtracted from all samples and a calibration curve prepared by linear regression of the absorbance values of the standards plotted vs. FVIII concentration. The specific activity was calculated by dividing the activity of the samples with the protein concentration determined by ELISA (example 4). The activity relative to the FVIII-cMyc2 template was calculated by dividing the specific activity for the FVIII variant with the specific activity for the FVIII template. The data in table 1 demonstrate a large variation in FVIII:C activity between the different FVIII variants.

The data in table 2 demonstrate that the FVIII:C activity was maintained in the selected FVIII variants.

Example 4: Total FVIII Antigen Measured in ELISA

The amount of the FVIII variants were evaluated in an ELISA from Affinity Biologicals (# F8C-EIA) as follows: Microtiter plates (NUNC™) were coated with 100 μL/well Coating antibody in PBS (0.10 M sodium phosphate; 0.145 M NaCl, pH 7.2). Plates were sealed and incubated overnight at 4° C. Plates were washed 5× in wash buffer (0.01 M sodium phosphate, 0.145 M NaCl, 0.05% TWEEN® 20, pH 7.2) and blocked in wash buffer for 30 minutes at ambient temperature. Samples were diluted in assay buffer (0.1 M HEPES; 0.1 M NaCl; 10 g/L BSA; 0.1% TWEEN 20, pH 7.2) and 10 μL diluted samples (or calibrator/diluted control) were transferred to each well. Detection antibody (100 μL) were added to the plate and incubated 1½ hour on shaker at ambient temperature. Plates were washed and 100 μL substrate (TMB monocomponent substrate, Kem-en-Tec) were added and incubate on shaker until sufficient color was developed. The reaction was stopped by adding 100 μL Stop buffer (4M $H_3PO_4$). The absorbance at 450 nm was measured on an Envision plate reader (PerkinElmer) with absorbance at 620 nm used as reference wavelength.

Example 5: LRP Binding in ELISA

The FVIII variants were further evaluated for the ability to bind to LRP as follows: All samples were diluted 40-fold and 80-fold in buffer without NaCl (0.1 M HEPES; 10 g/L BSA; 0.1% TWEEN 20, pH 7.2). The standard (FVIII-cMyc2) was diluted to 3000; 1000; 333; 111; 37; 12.3; 4.12 and 0 ng/mL. Microtiterplates were coated with LRP (1 ug/mL, BioMac, Leipzig, Germany) in PBS (100 μL/well) and sealed and incubated for at least 72 h at 4° C. Plates were washed 5× in buffer without NaCl, and blocked in the buffer for at least 15 min. Standard/diluted sample (50 μL/well) and buffer (150 μL/well) were added to the plates and incubated over night at room temperature in a wet chamber. Plates were washed and 100 μL/well of 1 μg/mL biotinylated anti FVIII A2 antibody (BDD-FVIII-1F5*biotin, prepared in house using standard techniques) were added and incubated 1 hour at room temperature on a shaker. Plates were washed 5× and 100 μL/well Streptavidin*HRP (KPL, Kirkegaard & Perry Laboratories, Inc.) diluted 1:20000 in buffer was added and the plates incubated 1 hour at room temperature on a shaker. Plates were washed 5× and 100 μL/well TMB monosubstrate (Kem-en-Tec) was added and plates incubated on a shaker until sufficient color was obtained. The reaction was stopped with 100 μL/well 4M $H_3PO_4$ before the absorbance at 450 nm was measured on an Envision plate reader (PerkinElmer) with absorbance at 620 nm used as reference wavelength. The specific LRP binding was calculated by dividing the LRP binding of the variants with the protein concentration determined by ELISA (example 4). The LRP binding relative to FVIII-cMyc2 template was calculated by dividing the specific LRP binding for the variants with the specific LRP binding for the FVIII-cMyc2 template. Table 1 shows expression level, FVIII:C activity and LRP binding of FVIII variants where surface exposed lysine or arginine residues were mutated. For some of the FVIII variants the activity and LRP binding could not be detected due to low expression level. These are marked "low conc" in the table. Most of the FVIII variants where the expression level was sufficiently high to allow analysis of LRP binding showed LRP binding close to that of the FVIII control "FVIII template" without substitutions. Some FVIII variants, e.g. K523A and K1972Q showed a decreased LRP binding concomitant with a reduction of activity. However, some of the FVIII variants with substitutions in the C1 and C2 domain, i.e. K2065A, R2090A, K2092A, R2215A, R2220Q and K2249A had reduced LRP binding (<0.53 relative to FVIII control) while the activity was maintained (>0.78 relative to FVIII control). These mutations are all located in the C1 foot and the C2 foot described above. When a mutation within this region of the C1 domain was combined with a mutation of the C2 domain (table 2) a further reduction of LRP binding was observed for the double mutations where R2215A was included. Also the R2090A-K2249A double mutant showed a larger reduction of LRP binding than seen for the single mutations. For some of the mutations where the expression level was lower than ≈350 ng/ml was it not possible to analyze LRP binding using the described assay. LRP binding of selected purified FVIII variants including lysine and arginine substitutions combined with F2093A were further analyzed by applying a range of concentrations (up to 18 nM) in the assay, and $K_d$ values calculated by non-linear regression of the binding curves using the equation for one site total binding in Prism version 5.01 Software. Table 3 shows the fold increase in $K_d$ relative to FVIII without mutations inserted. The higher the fold-increase in $K_d$, the more is LRP binding reduced. The data shows that if two or more, i.e. up to four, of the amino acid residues in the C1 (K2065, R2090, K2092, F2093) and C2 foot (R2215, R2220 and K2249) were substituted, a substantial reduction of LRP binding was observed.

TABLE 1

LRP binding and activity of FVIII single mutants

| FVIII variant | Concentration (ng/ml) | Specific LRP (Binding U/ng) | Specific Activity (mU/ng) | Relative to template LRP | Relative to template Activity |
|---|---|---|---|---|---|
| FVIII template | 3433 | 0.28 | 14.5 | 1.00 | 1.00 |
| R3A | <STD | low conc. | low conc. | low conc. | low conc. |
| R4A | 332 | 0.34 | 5.39 | 1.22 | 0.37 |
| R29A | 757 | 0.29 | 8.24 | 1.04 | 0.57 |
| R33A | 940 | 0.27 | 8.17 | 0.97 | 0.56 |
| K36A | 802 | 0.29 | 8.20 | 1.02 | 0.57 |
| K47A | 279 | 0.33 | 5.96 | 1.19 | 0.41 |
| K48Q | 30 | low conc. | low conc. | low conc. | low conc. |
| K63A | 548 | 0.34 | 9.04 | 1.22 | 0.62 |
| R65A | 293 | 0.36 | 7.33 | 1.31 | 0.51 |
| K89Q | 476 | 0.31 | 7.67 | 1.11 | 0.53 |
| K107Q | 525 | 0.10 | <STD | 0.37 | <STD |
| R121A | 317 | 0.33 | 6.02 | 1.17 | 0.42 |
| K123Q | 901 | 0.14 | 2.40 | 0.49 | 0.17 |
| K127A | 925 | 0.28 | 8.01 | 0.99 | 0.55 |
| K142A | 781 | 0.26 | 6.49 | 0.95 | 0.45 |
| K166A | 332 | 0.32 | 7.07 | 1.15 | 0.49 |
| R180A | 422 | 0.33 | 5.03 | 1.19 | 0.35 |
| K186A | 786 | 0.29 | 8.05 | 1.04 | 0.56 |
| K188A | 651 | 0.29 | 7.28 | 1.05 | 0.50 |
| K194A | 770 | 0.32 | 8.50 | 1.15 | 0.59 |
| K206A | 669 | 0.27 | 6.44 | 0.97 | 0.44 |
| K213A | 699 | 0.27 | 7.90 | 0.96 | 0.55 |
| R220A | 629 | 0.34 | 7.30 | 1.21 | 0.50 |
| R226A | 447 | 0.32 | 7.71 | 1.13 | 0.53 |
| K230A | 1069 | 0.24 | 5.90 | 0.88 | 0.41 |
| R240A | 864 | 0.27 | 6.61 | 0.96 | 0.46 |
| R250A | 1252 | 0.20 | 5.17 | 0.71 | 0.36 |
| K251A | 2539 | 0.16 | 4.75 | 0.57 | 0.33 |
| R279A | 2237 | 0.19 | 3.14 | 0.67 | 0.22 |
| R282Q | 481 | 0.11 | 0.18 | 0.41 | 0.01 |
| K325A | 895 | 0.26 | 7.09 | 0.94 | 0.49 |
| R336A | 2123 | 0.21 | 8.42 | 0.76 | 0.58 |
| K338A | 1934 | 0.22 | 5.37 | 0.78 | 0.37 |
| R359A | 2410 | 0.18 | 6.24 | 0.63 | 0.43 |
| R372A | 3426 | 0.14 | 0.04 | 0.51 | 0.00 |
| K376A | 1811 | 0.19 | 0.14 | 0.67 | 0.01 |
| K377A | 3369 | 0.13 | 2.82 | 0.46 | 0.19 |
| K380A | 2116 | 0.18 | 4.94 | 0.64 | 0.34 |
| R405A | 3193 | 0.15 | 6.19 | 0.54 | 0.43 |
| K408A | 2165 | 0.18 | 9.45 | 0.64 | 0.65 |
| R418A | 1334 | 0.23 | 10.12 | 0.83 | 0.70 |
| R421A | 1504 | 0.23 | 8.53 | 0.83 | 0.59 |
| K422A | 1735 | 0.16 | 6.07 | 0.57 | 0.42 |
| K424A | 1075 | 0.14 | 7.78 | 0.50 | 0.54 |
| K425Q | <STD | low conc. | low conc. | low conc. | low conc. |
| R427Q | 1252 | 0.21 | 5.81 | 0.77 | 0.40 |
| K437A | 1495 | 0.12 | 8.20 | 0.44 | 0.57 |
| R439A | 881 | 0.30 | 8.30 | 1.09 | 0.57 |
| K466Q | 1082 | 0.20 | 10.16 | 0.70 | 0.70 |

TABLE 1-continued

LRP binding and activity of FVIII single mutants

| FVIII variant | Concentration (ng/ml) | Specific LRP (Binding U/ng) | Specific Activity (mU/ng) | Relative to template LRP | Relative to template Activity |
|---|---|---|---|---|---|
| R471A | 284 | low conc. | 3.39 | low conc. | 0.23 |
| R484A | 6037 | 0.15 | 5.05 | 0.54 | 0.35 |
| R489A | 5928 | 0.18 | 4.79 | 0.64 | 0.33 |
| R490A | 3441 | 0.13 | 3.90 | 0.48 | 0.27 |
| K493A | 5584 | 0.06 | 4.70 | 0.20 | 0.32 |
| K496A | 2718 | n.d.* | 0.08 | n.d.* | 0.01 |
| K499A | 2245 | 0.25 | 6.89 | 0.89 | 0.48 |
| K510A | 3441 | 0.25 | 3.11 | 0.89 | 0.22 |
| K512A | 4527 | 0.16 | 4.58 | 0.58 | 0.32 |
| K523A | 10028 | 0.08 | 2.33 | 0.27 | 0.16 |
| R527A | 4806 | 0.12 | 5.95 | 0.42 | 0.41 |
| R531Q | 1946 | 0.15 | 0.64 | 0.53 | 0.04 |
| R541A | 1233 | 0.16 | 10.46 | 0.58 | 0.72 |
| K556A | 2612 | 0.21 | 5.35 | 0.75 | 0.37 |
| R562A | 2361 | 0.25 | 11.20 | 0.91 | 0.77 |
| K570A | 2208 | 0.34 | 12.86 | 1.23 | 0.89 |
| R571A | 2974 | 0.18 | 9.00 | 0.66 | 0.62 |
| R583A | 1959 | 0.21 | 8.65 | 0.75 | 0.60 |
| R593A | 1845 | 0.12 | 10.00 | 0.45 | 0.69 |
| K659Q | 2306 | 0.26 | 8.08 | 0.92 | 0.56 |
| K661A | 1522 | 0.35 | 6.71 | 1.25 | 0.46 |
| R698A | 1602 | 0.23 | 6.04 | 0.82 | 0.42 |
| R700Q | 759 | 0.38 | 12.16 | 1.36 | 0.84 |
| K707A | 2708 | 0.17 | 9.46 | 0.63 | 0.65 |
| K713A | 1934 | 0.21 | 9.25 | 0.75 | 0.64 |
| R1689A | 835 | low conc. | 1.68 | low conc. | 0.12 |
| K1693A | 4298 | 0.13 | 6.79 | 0.45 | 0.47 |
| K1694A | 2929 | 0.16 | 7.02 | 0.56 | 0.48 |
| R1696Q | 1233 | 0.11 | 5.64 | 0.41 | 0.39 |
| R1705A | 231 | low conc. | 4.87 | low conc. | 0.34 |
| R1719A | 2321 | 0.13 | 8.61 | 0.45 | 0.59 |
| R1721A | 2051 | 0.20 | 7.93 | 0.70 | 0.55 |
| K1731A | 60 | low conc. | low conc. | low conc. | low conc. |
| K1732Q | <STD | low conc. | low conc. | low conc. | low conc. |
| R1749Q | 1879 | 0.11 | 4.87 | 0.39 | 0.34 |
| R1764Q | 582 | 0.26 | 8.09 | 0.92 | 0.56 |
| R1776A | 1415 | 0.16 | 9.16 | 0.59 | 0.63 |
| R1781Q | 644 | 0.10 | 16.11 | 0.36 | 1.11 |
| R1797A | 1748 | 0.23 | 13.06 | 0.81 | 0.90 |
| R1803A | 1867 | 0.18 | 5.98 | 0.65 | 0.41 |
| K1804Q | 2974 | 0.15 | 6.74 | 0.55 | 0.47 |
| K1808A | 2269 | 0.17 | 13.74 | 0.63 | 0.95 |
| K1813A | 2341 | 0.16 | 13.20 | 0.56 | 0.91 |
| K1818A | 1557 | 0.28 | 14.10 | 1.00 | 0.97 |
| K1827A | 2949 | 0.14 | 8.93 | 0.49 | 0.62 |
| K1833Q | 390 | low conc. | 0.09 | low conc. | 0.01 |
| K1845A | 1063 | 0.22 | 11.11 | 0.79 | 0.77 |
| R1869A | 741 | 0.14 | 7.18 | 0.49 | 0.50 |
| K1887A | 665 | 0.19 | 13.64 | 0.68 | 0.94 |
| R1897A | 1809 | 0.15 | 10.89 | 0.54 | 0.75 |
| R1900A | 1675 | 0.17 | 11.24 | 0.62 | 0.78 |
| K1913A | 1493 | 0.21 | 8.28 | 0.75 | 0.57 |
| R1917A | 866 | 0.16 | 5.34 | 0.59 | 0.37 |
| R1939A | 980 | 0.17 | 10.46 | 0.61 | 0.72 |
| R1941Q | 348 | low conc. | 1.23 | low conc. | 0.08 |
| R1966Q | 692 | 0.15 | 3.21 | 0.52 | 0.22 |
| K1967A | 1462 | 0.16 | 7.00 | 0.59 | 0.48 |
| K1968A | 585 | 0.17 | 15.72 | 0.62 | 1.09 |
| K1972Q | 1804 | 0.07 | 1.51 | 0.27 | 0.10 |
| K1992A | 1394 | 0.13 | 4.50 | 0.46 | 0.31 |
| R1997Q | 75 | low conc. | low conc. | low conc. | low conc. |
| K2020A | 171 | low conc. | 9.48 | low conc. | 0.65 |
| R2033A | 1399 | 0.25 | 12.62 | 0.91 | 0.87 |
| K2049A | 1063 | 0.17 | 13.80 | 0.62 | 0.95 |
| R2052A | 171 | 0.49 | 7.94 | 1.75 | 0.55 |
| K2065A | 1581 | 0.14 | 11.68 | 0.49 | 0.81 |
| K2072A | 1354 | 0.16 | 9.08 | 0.58 | 0.63 |
| K2085A | 1765 | 0.14 | 11.20 | 0.50 | 0.77 |
| R2090A | 1832 | 0.10 | 16.24 | 0.35 | 1.12 |
| K2092A | 1056 | 0.14 | 12.54 | 0.51 | 0.87 |
| K2110A | 1424 | 0.26 | 13.93 | 0.92 | 0.96 |
| K2111A | 1378 | 0.16 | 8.65 | 0.58 | 0.60 |

TABLE 1-continued

LRP binding and activity of FVIII single mutants

| FVIII variant | Concentration (ng/ml) | Specific LRP (Binding U/ng) | Specific Activity (mU/ng) | Relative to template LRP | Relative to template Activity |
|---|---|---|---|---|---|
| R2116Q | 1776 | 0.20 | 11.52 | 0.71 | 0.80 |
| K2136A | 1436 | 0.17 | 10.81 | 0.63 | 0.75 |
| R2147A | 245 | low conc. | 6.67 | low conc. | 0.46 |
| R2150Q | 896 | 0.23 | 7.36 | 0.84 | 0.51 |
| R2159A | 1095 | 0.15 | 6.40 | 0.54 | 0.44 |
| R2163Q | 483 | low conc. | 8.61 | low conc. | 0.59 |
| K2183A | 1175 | 0.13 | 11.81 | 0.48 | 0.82 |
| K2207A | 87 | low conc. | low conc. | low conc. | low conc. |
| R2209Q | 78 | low conc. | low conc. | low conc. | low conc. |
| R2215A | 1480 | 0.15 | 13.72 | 0.53 | 0.95 |
| R2220Q | 589 | 0.09 | 13.46 | 0.33 | 0.93 |
| K2227A | 1781 | 0.23 | 10.21 | 0.82 | 0.71 |
| K2236A | 789 | 0.22 | 11.90 | 0.79 | 0.82 |
| K2239Q | 1172 | 0.14 | 8.56 | 0.51 | 0.59 |
| K2249A | 1832 | 0.13 | 11.28 | 0.45 | 0.78 |
| K2258A | 1069 | 0.32 | 14.63 | 1.14 | 1.01 |
| K2279A | 371 | low conc. | 16.34 | low conc. | 1.13 |
| K2281A | 1069 | 0.16 | 15.86 | 0.58 | 1.10 |
| R2304A | 173 | low conc. | 6.79 | low conc. | 0.47 |
| R2307Q | 135 | low conc. | 3.63 | low conc. | 0.25 |
| R2320Q | 576 | 0.09 | 12.89 | 0.34 | 0.89 |

*n.d. represents non detectable data as K496 is included in the epitope of the biotinylated detection anti FVIII A2 antibody BDD-FVIII-1F5*biotin (example 5). Therefore LRP binding can not be detected for K496A in the assay used.

TABLE 2

Selected FVIII single and double mutants with decreased LRP binding

| FVIII variant | Concentration (ng/ml) | Specific LRP (Binding U/ng) | Specific Activity (mU/ng) | Relative to template LRP | Relative to template Activity |
|---|---|---|---|---|---|
| FVIII template | 2017 | 0.51 | 6.56 | 1.00 | 1.00 |
| K2065A | 2024 | 0.29 | 7.44 | 0.57 | 1.13 |
| R2090A | 1333 | 0.30 | 9.37 | 0.58 | 1.43 |
| K2092A | 1720 | 0.32 | 7.87 | 0.62 | 1.20 |
| R2215A | 1872 | 0.16 | 8.67 | 0.32 | 1.32 |
| R2220Q | 326 | low conc. | 10.72 | low conc. | 1.63 |
| K2249A | 1984 | 0.33 | 6.20 | 0.64 | 0.95 |
| R2320Q | 386 | 0.39 | 9.55 | 0.77 | 1.46 |
| K2065A-R2215A | 1842 | 0.11 | 6.75 | 0.22 | 1.03 |
| R2090A-R2215A | 917 | <detec. limit (0.13) | 11.94 | <detec. limit (0.26) | 1.82 |
| K2092A-R2215A | 1997 | <detec. limit (0.06) | 8.32 | <detec. limit (0.12) | 1.27 |
| K2065A-R2220Q | 292 | low conc. | 10.89 | low conc. | 1.66 |
| R2090A-R2220Q | 97 | low conc. | 13.42 | low conc. | 2.05 |
| K2092A-R2220Q | 275 | low conc. | 9.80 | low conc. | 1.49 |
| K2065A-K2249A | 1531 | 0.31 | 7.17 | 0.60 | 1.09 |
| R2090A-K2249A | 838 | 0.15 | 11.09 | 0.29 | 1.69 |
| K2092A-K2249A | 833 | 0.24 | 7.39 | 0.47 | 1.13 |
| K2065A-R2320Q | <STD | low conc. | low conc. | low conc. | low conc. |
| R2090A-R2320Q | 113 | low conc. | 15.24 | low conc. | 2.32 |
| K2092A-R2320Q | 270 | low conc. | 10.13 | low conc. | 1.54 |

TABLE 3

LRP binding relative to wt FVIII determined by titrations in ELISA

| FVIII variant | LRP binding ($K_d$ relative to that of wt FVIII) |
|---|---|
| K2065A-R2215A | 2.45 |
| K2092A-R2215A | 3.34 |
| K2092A-F2093A | 2.89 |
| K2065A-K2092A-F2093A-R2215A | >20 |

Example 6: LRP Binding Studies by Surface Plasmon Resonance (SPR) Analysis

SPR analysis was performed employing a BIAcore™3000 biosensor system (Biacore AB, Uppsala, Sweden). Full length LRP (BioMac, Leipzig, Germany) was covalently coupled (10 fmol/mm$^2$) to the dextran surface of an activated CM5-sensor chip via primary amino groups, using the amine-coupling kit as prescribed by the supplier. The FVIII derivatives FVIII-YFP, FVIII-YFP-K2092A, FVIII-YFP-F2093A and FVIII-YFP-K2092A-F2093A were constructed and expressed as described (Blood 2009; 114: 3938-3945), except that the anti-FVIII antibody CLB-CAg 117 was replaced by the single chain antibody fragment VK34 (Blood 2000; 96: 540-545) which has been constructed into the full length IgG monoclonal antibody VK34 as described (Br J Haematol 2008; 142: 644-652). FVIII was loaded on the VK34 Sepharose® column in 50 mM imidazole (pH 6.7), 50 mM $CaCl_2$, 0.8 M NaCl. After loading, the column was subsequently washed with 50 mM imidazole (pH 6.7), 50 mM $CaCl_2$, 0.8 M NaCl and 50 mM imidazole (pH 6.4), 40 mM $CaCl_2$, 5% (v/v) ethylene glycol buffer. Next, FVIII was eluted from the VK34 Sepharose column in 50 mM imidazole (pH 6.4), 40 mM $CaCl_2$, 55% (v/v) ethylene glycol. FVIII containing fractions were diluted in 50 mM Tris (pH 8.0), 100 mM NaCl, 5 mM $CaCl_0$ 10% (v/v) glycerol and absorbed to Q Sepharose FF (Amersham Biosciences, Belgium). Subsequently, the Q Sepharose column was washed with 50 mM Tris (pH 8.0), 100 mM NaCl, 5 mM $CaCl_0$ 10% (v/v) glycerol. FVII was eluted from the Q Sepharose column in 50 mM Tris (pH 7.4), 5 mM $CaCl_2$, 0.8 M NaCl, 50% (v/v) glycerol and stored at −20° C. The purified FVIII variants maintained full activity as assessed by the ratio of 0.92-1.03 between activity (FVIII Coatest method, Chromogenix, Milan, Italy) and antigen (FVIII ELISA, see Blood 2009; 114: 3938-3945). FVIII derivatives (60 nM) were passed over immobilized LRP, and the binding response in resonance units (RU), corrected for non-specific binding, was recorded during 360 seconds of association.

Table 4 shows that LRP binding of FVIII-K2092A was decreased approximately 100 RU as compared to FVIII-YFP without substitutions, while the binding of FVIII-F2093A was decreased only slightly (17 RU). However, when combining the two substitutions in the C1 foot a substantial decrease in LRP binding (approximately 200 RU) was observed.

TABLE 4

LRP binding of FVIII-YFP and variants measured by SPR

| FVIII variant | Binding response at 360 seconds (RU) |
| --- | --- |
| FVIII-YFP | 320 |
| FVIII-YFP-K2092A | 219 |
| FVIII-YFP-F2093A | 303 |
| FVIII-YFP-K2092A-F2093A | 116 |

Example 7: LRP Binding of FVIII Light Chain Variant

The K2065R, K2065A, K2092R and K2092A point mutations and K2065R-K2092R and K2065A-K2092A double mutations were introduced in the FVIII light chain by Quick Change Mutagenesis™ (Stratagene, La Jolla, Calif., USA) using appropriate primers as indicated by the manufactures. Serum free transfection of the FVIII light chain variants was performed using FREESTYLE™ 293-F cells (Invitrogen, Carlsbad, Calif., USA, # R790-07) and 293fectin (Invitrogen) following the manufacturer's recommendations. FREESTYLE™ 293-F cells suspension cells were grown in commercial FREESTYLE™ 293 Expression Medium (Invitrogen #. 12338-018). Cells were grown as suspension cells in shakers and incubated at 37° C. under 8% CO2 and 95% relative humidity. Cells were seeded at a density of $3 \times 10^5$ cells mL-1 and passaged every 3 to 4 days. Cells were harvested 120 hours after transfection and the cell pellet isolated by gentle centrifugation. Afterwards, the cell pellet was re-suspended in the FREESTYLE™ 293 Expression medium containing 0.55 M NaCl. Following gentle centrifugation, the FVIII light chain containing supernatants were harvested and stored at −20° C. until further analysis. LRP cluster II was expressed in Baby Hamster Kidney (BHK) cells and purified as described (J Biol Chem. 2003; 278: 9370-7). Association and dissociation of LRP cluster II to the FVIII light chain variants K2065A, K2092A, K2065A-K2092A, K2065R, K2092R and K2065R-K2092R was assessed by SPR analysis employing a BIAcore 3000 biosensor (Biacore AB, Uppsala, Sweden).

The anti-C2 antibody CLB-EL14 IgG4 (Br J Haematol 2008; 142:644-652) was immobilized onto a CM5 sensor chip to a density of 27 fmol/mm$^2$ using the amine coupling method according to the manufacturer's instructions. Subsequently, FVIII light chain variants K2065A, K2092A, K2065A-K2092A, K2065R, K2092R and K2065R-K2092R were bound to the anti-C2 antibody at a density of 17 fmol/mm$^2$. Varying concentrations (0.2-200 nM) of LRP cluster II were passed over the FVIII light chain variants K2065A, K2092A, K2065A-K2092A, K2065R, K2092R and K2065R-K2092R in a buffer containing 150 mM NaCl, 5 mM CaCl2, 0.005% (v/v) TWEEN 20 and 20 Mm HEPES (pH 7.4) at 25° C. with a flow rate of 20 μL/min. The sensor chip surface was regenerated three times after each concentration of LRP cluster II using the same buffer containing 1 M NaCl. Binding to FVIII light chain variants K2065A, K2092A, K2065A-K2092A, K2065R, K2092R and K2065R-K2092R was recorded during 240 seconds of association and corrected for non-specific binding. Binding data during the association phase were fitted in a one-phase exponential association model. Responses at equilibrium were plotted as a function of the LRP cluster II concentration. The responses at equilibrium were fitted by non-linear regression using a standard hyperbola to obtain $K_D$ values (GraphPad Prism 4 software, San Diego, Calif., USA).

Table 5 shows that LRP cluster II binding to the FVIII light chain variant carrying two lysine replacements in the C1 domain at positions K2065 and K2092 is more impaired than a FVIII light chain variant carrying one lysine replacement in the C1 domain at position K2065 or K2092.

TABLE 5

Affinity of FVIII light chain C1 variants for LRP cluster II as measured by SPR.

| FVIII light chain variant | $K_D$ for LRP cluster II binding (nM) |
| --- | --- |
| wt FVIII | 33 ± 2 |
| K2065R | 78 ± 6 |
| K2092R | 45 ± 4 |
| K2065R-K2092R | 95 ± 8 |
| K2065A | 84 ± 7 |
| K2092A | 46 ± 4 |
| K2065A-K2092A | 248 ± 16 |

Example 8: Cellular Uptake of FVIII

A variety of cells are expressing LRP and related endocytic receptors. These include the human glioblastoma cell line U87 MG cells which are known in the art to express high levels of LRP (Cancer Res 2000; 60: 2300-2303) These cells are particularly useful for studying LRP-mediated cellular uptake of LRP binding ligands such as FVIII. U87 MG cells were obtained from ATCC (HTB-14). The cells were grown in 24 wells plates for 48 hours on EMEM supplemented with 10% heat inactivated FCS at 37° C. in 5% $CO_2$. Cells were washed with a buffer containing 10 mM HEPES (pH 7.4), 135 mM NaCl, 10 mM KCl, 5 mM $CaCl_2$, 2 mM $MgSO_4$ and incubated for 15 minutes at 37° C. with 40 nM FVIII-YFP, FVIII-YFP-K2092A, FVIII-YFP-F2093A and FVIII-YFP-K2092A-F2093A (variants prepared as described in example 6). Cells were subsequently washed respectively with the same HEPES buffer and TBS (20 mM Tris-HCl, 150 mM NaCl). Cells were collected employing trypsin, neutralized with EMEM supplemented with 10% heat inactivated FCS, washed with TBS and resuspended in TBS+0.5% (w/v) BSA. Uptake of FVIII was determined by flow cytometry analysis. For cell binding studies, cells were incubated for 15 minutes at 4° C. with 10 mM HEPES (pH 7.4), 135 mM NaCl, 10 mM KCl, 5 mM $CaCl_2$, 2 mM $MgSO_4$. Next, cells were incubated for 45 minutes at 4° C. with 40 nM FVIII-YFP, FVIII-YFP-K2092A, FVIII-YFP-F2093A and FVIII-YFP-K2092A-F2093A. Cells were subsequently washed with icecold TBS and then with icecold TBS containing 0.5% (w/v) BSA. Cells were scraped and resuspended in TBS+0.5% (w/v) BSA. FVIII binding and uptake was measured using a fluorescence-activated cell sorter (Becton Dickinson LSR II flow cytometer). Noise was reduced during analysis by eliminating events with forward and side scatter values different from those characteristic for U87MG cells. Flow cytometry data were collected using FacsDiva version 5.0.3 (Becton Dickinson) and downloaded into the program FlowJo for analysis. Table 6 shows the mean fluorescence intensity of U87 MG cells in the presence of FVIII-YFP-K2092A, FVIII-YFP-F2093A and FVIII-YFP-K2092A-F2093A at 4° C. (cell binding) and at 37° C. (cellular uptake).

The data show that cell binding and uptake of FVIII-YFP-K2092A, FVIII-YFP-F2093A and FVIII-YFP-K2092A-F2093A by LRP expressing cells was reduced compared to FVIII-YFP without mutations.

TABLE 6

Binding and uptake of FVIII-YFP and variants thereof by LRP expressing cells

| | FVIII-YFP (mean fluorescence intensity) | |
|---|---|---|
| FVIII variant | Binding (4° C.) | Uptake (37° C.) |
| FVIII-YFP | 11750 | 5900 |
| FVIII-YFP-K2092A | 6500 | 1230 |
| FVIII-YFP-F2093A | 4960 | 1350 |
| FVIII-YFP-K2092A-F2093A | 4750 | 1310 |

Example 9: Maintained Specific Activity of FVIII C1 Double and Triple Mutants

FVIII variants FVIII-R2090A, FVIII-K2092A-F2093A and FVIII-R2090A-K2092A-F2093A were prepared as described in example 6. The FVIII activity was measured in a chromogenic FVIII assay as described in example 6. Protein concentrations were measured using the Brad-ford method (Anal Biochem 1976; 72: 248-254). The properties of the purified proteins are listed in Table 7. The specific activity was calculated by dividing the activity with the protein concentration or the antigen. FVIII with the K2092A-F2093A and the R2090A-K2092A-F2093A mutations maintained activity.

TABLE 7

Activity of FVIII-K2092A-F2093A and FVIII-R2090A-K2092A-F2093A.

| FVIII variant | Protein (µg/ml) | FVIII activity (IU/ml) | Specific activity (IU/µg) |
|---|---|---|---|
| wt FVIII | 3070 | 19338 | 6.3 |
| FVIII-K2092A-F2093A | 4546 | 43917 | 9.7 |
| FVIII-R2090A-K2092A-F2093A | 4853 | 40194 | 8.3 |

Example 10: Cellular Uptake of FVIII C1 Double and Triple Mutant

Endocytosis of the FVIII-K2092A-F2093A and FVIII-R2090A-K2092A-F2093A mutants without the YFP (yellow fluorescence protein) fusion partner was analyzed in U87MG cells (see example 8). Cells were incubated for 15 minutes at 37° C. with 10 mM HEPES (pH 7.4), 135 mM NaCl, 10 mM KCl, 5 mM CaCl$_2$, 2 mM MgSO$_4$. Next, cells were incubated for 45 min with different amounts of wild type FVIII, FVIII-K2092A-F2093A or FVIII-R2090A-K2092A-F2093A. Cells were subsequently washed with ice-cold TBS (50 mM Tris-HCl pH 7.6, 150 mM NaCl), scraped off, resuspended in ice-cold TBS and washed once with ice-cold TBS. Subsequently, cells were fixed with 1% freshly dissolved ultrapure methanol-free paraformaldehyde (Polysciences, Eppelheim, Germany) and incubated with FITC-conjugated monoclonal anti-FVIII antibody CLB-CAg117 in the presence of 0.05% saponin in TBS containing 0.5% HSA. Mean fluorescence intensities were determined by flow cytometry using LSRII (BD Biosciences, Uppsala, Sweden).

The results are summarized in Table 8. FVIII is endocytosed in a dose-dependent manner by U87MG cells. Uptake of FVIII-K2092A-F2093A was severely impaired. Assessment of the uptake of FVIII-R2090A-K2092A-F2093A revealed that the uptake of this variant was even more reduced when compared to that of FVIII-K2092A-F2093A. These results show that replacement of R2090, K2092 and F2093 resulted in a FVIII molecule with reduced uptake in LRP expressing cells.

TABLE 8

Uptake of FVIII-K2092A-F2093A and FVIII-R2090A-K2092A-F2093A in U87MG cells

| | FVIII uptake at the noted concentration added (fluorescence intensity)[1] | | | | |
|---|---|---|---|---|---|
| FVIII variant | 5 nM | 10 nM | 20 nM | 40 nM | 80 nM |
| wt FVIII | 2042 | 4230 | 6187 | 10390 | 13724 |
| FVIII-K2092A/F2093A | 1944 | 2715 | 4070 | 4745 | 9048 |
| FVIII-R2090A-K2092A-F2093A | 1558 | 1629 | 1953 | 3804 | 3859 |

[1]The mean fluorescence intensity obtained in the absence of FVIII was 737

Example 11: Cellular Uptake of FVIII C1 and C2 Double Mutants

Collagen-coated 24 wells plates (Blood 2002; 99:457-462) were seeded with U87MG cells in DMEM-F12 supplemented with 10% heat inactivated FCS at 37° C. in 5% CO$_2$. Cells were grown to confluence, washed with a buffer containing 10 mM HEPES (pH 7.4), 135 mM NaCl, 10 mM KCl, 5 mM CaCl$_2$, 2 mM MgSO$_4$, and were incubated for 30 minutes at 37° C. with 40 nM FVIII-K2065A, FVIII-K2249A, FVIII-K2065A-K2249A, FVIII-K2092A, FVIII-R2215A, or FVIII-K2092A-R2215A (see examples 1 and 2). Cells were collected by scraping in TBS (20 mM Tris-HCl, 150 mM NaCl) supplemented with 0.5% BSA. Cells were re-suspended and fixed for 15 minutes at room temperature in 0.4% ultrapure methanol-free paraformaldehyde (Polysciences, Eppelheim, Germany). Fixed cells were incubated for 60 minutes at room temperature with mouse anti-cMyc antibody 9E10 (Sigma, M4439) that was diluted 500-fold in TBS, 1% BSA, 0.3% saponin. Cells were washed with TBS, 0.5% BSA, and subsequently incubated for 45 minutes at room temperature with the secondary antibody Alexa Flour 488 goat anti-mouse antibody (Invitrogen, A-11001) that was diluted 200-fold in TBS, 1% BSA, 0.3% saponin. Cell were washed and re-suspended in TBS, 0.5% BSA and analyzed employing a fluorescence-activated cell sorter (Becton Dickinson LSR II flow cytometer) as described in example 8. Table 9 displays the mean fluorescence intensity of the cells. The single substitutions show a reduced uptake as compared to WT FVIII. The strongest defect in cellular uptake is however observed for the variants carrying a substitution in both the C1 and the C2 domain.

TABLE 9

Cellular uptake of FVIII variants (40 nM) with substitutions in the C1 domain and/or the C2 domain.

| FVIII variant | Uptake of FVIII variant relative to wt FVIII (%) |
|---|---|
| wt FVIII | 100 |
| FVIII-K2092A | 65 |
| FVIII-K2065A | 75 |
| FVIII-R2215A | 77 |
| FVIII-K2249A | 57 |
| FVIII-K2065A-K2249A | 29 |
| FVIII-K2092A-R2215A | 41 |
| FVIII-K2065A-R2215A | 48 |

Example 12: Cellular Uptake of FVIII by Dendritic Cells

Dendritic cells mediate uptake of FVIII before presentation to the immune system and potentially elicit an immune response (Blood 2007; 109: 610-612, J Thromb Haemost 2009; 7: 1816-1823). Dendritic cells express LRP as well as other endocytotic receptors. The cellular uptake of FVIII variants was further investigated using human monocyte-derived dendritic cells, human monocyte derived macrophages and murine bone marrow derived dendritic cells. Monocytes were isolated from peripheral blood mononuclear cells from apheresis samples using CD14 microbeads, a magnetic cell separator and a Elutra™ cell separation system as described previously (Vaccine 2007; 25: 7145-52). Monocytes were differentiated into dendritic cells in CellGro DC medium supplemented with 100 U/ml penicillin, 100 µg/ml streptomycin, 1000 U/ml human recombinant GM-CSF and 800 U/ml human recombinant IL-4. After 4-6 days of cell culturing, immature phenotype of the cells was evaluated by determining cell surface markers CD14, CD80, CD83 and CD86. To monitor uptake of FVIII variants by flow cytometry approximately $2 \times 10^5$ of immature DCs were first washed once with serum-free medium and incubated with FVIII in 120 µl of serum-free CellGro DC medium for 30 minutes at 37° C. After FVIII uptake, cells were washed with ice-cold TBS, fixed with 1% freshly prepared paraformaldehyde and incubated with FITC-conjugated monoclonal anti-FVIII antibody CLB-CAg117 in presence or absence of 0.05% saponin in TBS containing 0.5% human serum albumin. Mean fluorescence intensities and percentage of positive cells were determined by flow cytometry using LSRII (BD Biosciences, Uppsala, Sweden). The results of uptake experiments employing purified wild type FVIII, FVIII-K2092A-F2093A, and FVIII-R2090A-K2092A-F2093A are depicted in Table 10.

The results show a dose-dependent uptake of wild type FVIII by human dendritic cells. The variant FVIII-K2092A-F2093A shows a strongly reduced uptake by dendritic cells, whereas FVIII-R2090A-K2092A-F2093A reveals an even more pronounced decrease in its uptake by dendritic cells. These results show that replacement of R2090, K2092 and F2093 strongly reduces the uptake of FVIII by dendritic cells.

TABLE 10

Uptake of wt FVIII, FVIII-K2092A-F2093A, and FVIII-R2090A-K2092A-F2093A in human monocyte-derived dendritic cells.

| | FVIII uptake at the noted concentration added (fluorescence intensity)[1] | | |
|---|---|---|---|
| FVIII variant | 10 nM | 20 nM | 40 nM |
| wt FVIII | 10950 | 15550 | 24550 |
| FVIII-K2092A-F2093A | 5912 | 7448 | 10800 |
| FVIII-R2090A-K2092A-F2093A | 3308 | 4074 | 5905 |

[1]The mean fluorescence intensity obtained in the absence of FVIII was 1635.

Example 13: Cellular Uptake of FVIII in Macrophages

Macrophages are also able to take up FVIII in liver and spleen and to present FVIII to the immune system (Blood 2008; 112: 1704-1712, J Thromb Haemost 2009; 7: 1816-1823) and the uptake of the FVIII variants was therefore further evaluated using human monocyte derived macrophages. Monocytes were isolated as described in example 10 and differentiated into macrophages by incubating for 5 days in RPMI 1640 medium supplemented with 10% FCS, 100 U/ml penicillin, 100 μg/ml streptomycin and 50 ng/ml recombinant human M-CSF. To monitor uptake of FVIII variants by flow cytometry approximately $2\times10^5$ of macrophages were first washed once with serum-free medium and incubated with 15 nM FVIII in 120 μl of serum-free CellGro DC medium for 30 minutes at 37° C. After FVIII uptake, cells were washed with ice-cold TBS, fixed with 1% freshly prepared paraformaldehyde and incubated with FITC-conjugated monoclonal anti-FVIII antibody CLB-CAg117 in presence or absence of 0.05% saponin in TBS containing 0.5% human serum albumin. Mean fluorescence intensities and percentage of positive cells were determined by flow cytometry using LSRII (BD Biosciences, Uppsala, Sweden).

The results of uptake experiments employing wildtype FVIII, FVIII-R2090A, FVIII-K2092A-F2093A, and FVIII-R2090A-K2092A-F2093A are depicted in Table 11. The results re-veal that uptake of FVIII-R2090A is slightly reduced, whereas a strong decline in uptake is observed for FVIII-K2092A-F2093A. An even more pronounced reduction in uptake is observed for FVIII-R2090A-K2092A-F2093A. These results show that replacement of R2090, K2092 and F2093 reduces the uptake of FVIII also by macrophages.

TABLE 11

Uptake of wt FVIII, FVIII-K2092A-F2093A, and FVIII-R2090A-K2092A-F2093A (15 nM) in human monocyte-derived macrophages.

| FVIII variant | FVIII uptake at the noted concentration added (fluorescence intensity)[1] |
|---|---|
| Control (no FVIII added) | 3900 ± 114 |
| wt FVIII | 13965 ± 555 |
| FVIII-R2090A | 9642 ± 1440 |
| FVIII-K2092A-F2093A | 7937 ± 118 |
| FVIII-R2090A-K2092A-F2093A | 5773 ± 103 |

[1]Values are mean and SD of at least 3 experiments.

Example 14: Cellular Uptake of FVIII by Murine Bone Marrow Derived Dendritic Cells Subsequently the uptake FVIII variants was addressed using murine bone marrow derived dendritic cells. Bone marrow cells were isolated by flushing femurs from hemophilic E17 KO mice with PBS supplemented with 2% FCS. The bone marrow suspension was incubated in Tris-NH$_4$Cl at room temperature for 2 minutes to lyse erythrocytes. Finally, the cells were resuspended at 1×10$^6$ cells/ml containing 20 ng/ml mouse recombinant GM-CSF and cultured for 7-9 days in RPMI 1640 medium supplemented with 2.5 mM HEPES, 55 mM 2-mercaptoethanol, 100 U/ml penicillin, 100 µg/ml streptomycin, 5 mM glutamine and 10% FCS. Expression of CD11c, CD11 b, CD80, CD86 and Gr-1 was measured on day 7-9. Uptake of FVIII was studied as described above for human monocyte derived dendritic cells and macrophages. The results of FVIII uptake experiments are presented in Table 12. The results show that FVIII-R2090A is endocytosed at a slightly reduced level as compare to wildtype FVIII whereas endocytosis of FVIII-K2092A-F2093A is more severely impaired. Endocytosis of FVIII-R2090A-K2092A-F2093A is more severely impaired when compared to FVIII-K2092A-F2093A. These results show that replacement of R2090, K2092 and F2093 reduces the uptake of FVIII also by murine bone marrow derived dendritic cells.

TABLE 12

Uptake of wt FVIII, FVIII-R2090A, FVIII-K2092A-F2093A, and FVIII-R2090A-K2092A-F2093A (15 nM) in murine bone-marrow derived dendritic cells.

| FVIII variant | FVIII uptake (fluorescence intensity)[1] |
|---|---|
| Control (no FVIII added) | 1968 ± 235 |
| wt FVIII | 8661 ± 206 |
| FVIII-R2090A | 7907 ± 305 |
| FVIII-K2092A-F2093A | 5099 ± 275 |
| FVIII-R2090A-K2092A-F2093A | 3389 ± 93 |

[1]Values are mean and SD of at least 3 experiments.

Overall, findings reported in example 8 and 10-14 teach how to define residues contributing to interactive surfaces in FVIII that mediate its endocytosis by a variety of LRP expressing cells, including human dendritic cells and macrophages as well as murine dendritic cells.

Example 15: Anti FVIII C1 and C2 Antibodies Blocking FVIII Cellular Uptake

As an alternative approach to define residues contributing to FVIII cellular uptake a panel of antibodies with epitopes within all domains of FVIII was applied in FVIII cell binding studies employing U87MG cells (see example 8), primary rat hepatocytes and human monocyte derived macrophages. The antibodies ESH-2, ESH-4, ESH-5, and ESH-8 (Thromb Haemost 1986; 55: 40-46) are commercially available from American Diagnostica. KM33 is described in J Biol Chem 2003; 278: 9370-9377 and WO 03/093313. CLB-CAg117 is described in Blood 1998; 91: 2347-2352. The remaining antibodies were prepared in house after immunization of mice with FVIII using standard techniques for preparation of monoclonal antibodies. Freshly isolated primary rat hepatocytes prepared in house or purchased from Biopredic International (Rennes, France) were used. Briefly, anesthetized Sprague Dawley rats were opened and the portal vein cannulated while the vena cava was tied and then clipped following commencement of perfusion with HEPES buffer (25 mM HEPES, 0.38 mM Na$_2$HPO$_4$, 0.35 mM KH$_2$PO$_4$, 5.36 mM KCl, 0.11 M NaCl, 22 mM glucose, pH7.4). The tissue was digested with 120 mg collagenase (Sigma C-5138) in HEPES buffer and subsequently flushed with 5 mM CaCl$_2$ in HEPES buffer. The capsule tissue around the liver was peeled off to free the cells into wash buffer (D-MEM/F12 with L-Glutamine and 15 Mm HEPES (Gibco) supplemented with 1% BSA and 0.1 mM hydrocortisone hemisuccinate (Sigma) and 1 nM insulin (Sigma)). Cells were centrifuged at 50×g and supernatant discarded. The cell pellet was resuspended in William's E medium (Biopredic International, Rennes, France) supplemented with 2 mM L-glutamine, 100 UI/mL insulin, 100 µg/mL streptomycin and 5 µM hydrocortisone hemisuccinate. Hepatocytes were seeded in 24 well tissue culture plates at a density of 2.5×105 cells/well for a total of 48 h. Monocytes were isolated by magnetic separation using magnetic anti-CD14-beads (Miltenyi) and a MACS® column (Miltenyi) according to the manufactures instructions. The monocytes (0.5×10$^6$ cells/ml) were seeded in T-75 tissue culture flasks and added 3.3 ng/ml M-CSF (R&D Systems). Additional 3.3 ng/ml M-CSF was added after three days cell culturing. After six days were the macrophages washed with PBS and incubated 10-20 min at 4° C. with 2.5 mM EDTA in PBS with 5% FCS.

Cells were seeded in 48-well tissue culture plates at a density of 3.5×10$^5$ cells/well and incubated overnight. U87 cells and macrophages were carefully washed with buffer A (100 mM HEPES, 150 mM NaCl, 4 KCl, 11 mM Glucose, pH 7.4) and incubated for 15 min with buffer B (buffer A supplemented with 5 mM CaCl$_2$ and 1 mg/ml BSA). Anti FVIII antibodies (final concentration 10 µg/ml) was added to $^{125}$I-FVIII (final concentration 1 nM) and incubated 10 min before adding to the cells and incubating overnight at 4° C. Cells were subsequently washed two times with ice-cold buffer B and lysed with 200 mM NaOH, 1% SDS, 10 mM EDTA. A similar protocol was used for the primary rat hepatocytes except that media was used instead of buffer. $^{125}$I in the lysate was counted in a γ-counter (Cobra). Bound $^{125}$I in the absence of anti FVIII antibodies was set to 100%. Table 13 shows the effect of the anti FVIII antibodies on binding of $^{125}$I-FVIII to U87MG cells, macrophages and hepatocytes. The data shows that it is only the anti C1 antibodies KM33 and 4F30 and some of the anti C2 antibodies, i.e. ESH-4, 4F161 and CLB-CAg117, that inhibit FVIII binding to the cells. Notably, the panel of antibodies have similar effect on all three cell types analyzed indicating that it is the same epitopes on FVIII that is involved in cellular uptake irrespectively of cell type.

TABLE 13

Inhibition of FVIII cell binding by anti C1 and anti C2 antibodies

| Antibody | Epitopes[1] | $^{125}$I-FVIII binding (% of pos control)[2] | | |
|---|---|---|---|---|
| | | U87MG | Macrophages | Hepatocytes |
| ESH5 | A1 | 159 ± 12 | 178 ± 42 | 81 |
| 1F4 | A2 | 79 ± 16 | 99 ± 15 | 107 ± 29 |
| 1F5 | A2 | 87 ± 10 | 119 ± 13 | n/a |
| 1F10 | A2 | 66 ± 5 | 104 ± 26 | 97 ± 22 |
| 1F2 | A2 (720-740) | 80 ± 9 | 110 ± 10 | 107 ± 14 |
| 4F36 | A3 (1649-1871) | 140 ± 14 | 219 ± 58 | 153 |
| 4F30 | C1 | 24 ± 2 | 27 ± 10 | 3 ± 3 |

TABLE 13-continued

Inhibition of FVIII cell binding by anti C1 and anti C2 antibodies

| Antibody | Epitopes[1] | $^{125}$I-FVIII binding (% of pos control)[2] | | |
|---|---|---|---|---|
| | | U87MG | Macrophages | Hepatocytes |
| KM33 | C1 (K2092-S2094) | 23 ± 2 | 47 ± 17 | 5 ± 0 |
| 4F45 | light chain | 110 ± 12 | 138 ± 34 | n/a |
| ESH2 | light chain | 107 ± 28 | 155 ± 23 | n/a |
| ESH8 | C2 (2248-2285) | 92 ± 9 | 115 ± 20 | 92 ± 14 |
| ESH4 | C2 (2173-2222, 2248-2285 and/or 2303-2322) | 32 ± 3 | 50 ± 21 | 18 ± 4 |
| 4F161 | C2 | 35 ± 7 | n/a | n/a |
| CLB-CAg117 | C2 | 40 ± 7 | n/a | n/a |

[1]The domain location of epitopes for the in house antibodies was determined by Western blotting. For KM33 the epitope has partly been described (Blood 2009; 114: 3938-3946, J Thromb Haemost 2007; 5 suppl 2: abstract P-M-040). Data on potential epitopes for the ESH antibodies are described in the datasheet from American Diagnostica and J Biol Chem 1997; 272: 18007-18014, Thromb Haemost 2003; 89: 795-802, J Mol Recognit 2009; 22: 301-306, Blood 1995; 86: 1811-1819, Biochemistry 2005; 44: 13858-13865 (see Description of the Invention).
[2]The data for U87 MG cells and macrophages are mean and standard deviation for n = 3 or more, while n = 1-3 for hepatocytes.
n/a = not analyzed Example 163: Anti FVIII C1 and C2 Antibodies Prolong Half-Life of FVIII In Vivo FVIII prepared as described (Haemophilia 2010, 16; 349-359) was mixed with scFv or fab fragments of anti C1 and/or anti C2 antibodies in an amount ensuring A8% initial saturation of FVIII in vivo using $K_d$ values from surface plasmon resonance experiments and assuming a 20-fold dilution of test substance in vivo. This 20-fold dilution was based on a distribution volume of 70 ml/kg obtained for FVIII when administered alone, an estimated weight of the mice of 28.6 g and a volume of the test substance of 0.1 ml. FVIII alone (280 IU/kg) or mixed with antibodies were administered intravenously to VWF-deficent mice (n=6 per group). Blood were taken from the orbital plexus t=0.08; 1, 2, 3, 4 and 5 h. Three samples were taken from each mouse, and 3 samples were collected at each time point. Blood were immediately stabilized with sodium citrate and diluted in four volumes buffer (50 mM Tris, 150 mM NaCl, 1% BSA, pH 7.3, with preservative) before 5 min centrifugation at 4000×g. Plasma was frozen on dry ice and kept at −80° C. before analysis of FVIII antigen. The mean values were used for estimations of pharmacokinetic parameters, using a non-compartmental approach (Phoenix™ WinNonlin® Pro 6.1). The resulting PK values are shown in Table 14. While FVIII alone has a relatively fast clearance in the VWF-deficient mice, blocking either C1 or C2 resulted in decreased clearance and prolonged half-life (T½) and mean residence time. Blocking both an epitope in C1 and an epitope in C2 simultaneously resulted in a further decreased clearance and a prolonged T½ and mean residence time as compared to adding only one of the antibodies. This shows that the antibodies KM33 and 4F161 shield epitopes of FVIII involved in cellular uptake and thereby prolonging the half-life of FVIII.

TABLE 14

| Pharmacokinetics of FVIII co-administrated with anti C1 and/or anti C2 antibody fragments in VWF-deficient mice | | | |
|---|---|---|---|
| | Pharmacokinetic parameters | | |
| Test compound | T½ (h) | Clearance (mL/h/kg) | Mean Residence Time (h) |
| FVIII | 0.47 | 167 | 0.3 |
| FVIII + KM33 scFv | 1.2 | 55 | 1.7 |
| FVIII + 4F161 fab | 1.3 | 76 | 1.7 |
| FVIII + KM33 scFv + 4F161 fab | 2.0 | 25 | 3.0 |

Example 17: Epitopes of FVIII C1 and C2 Antibodies Blocking Cellular Uptake and Prolonging In Vivo Clearance The epitopes of the antibodies blocking cellular uptake described in Example 13 was mapped by hydrogen exchange mass spectrometry (HX-MS). The HX-MS technology exploits that hydrogen exchange (HX) of a protein can readily be followed by mass spectrometry (MS).

By replacing the aqueous solvent containing hydrogen with aqueous solvent containing deuterium, incorporation of a deuterium atom at a given site in a protein will give rise to an increase in mass of 1 Da. This mass increase can be monitored as a function of time by mass spectrometry in quenched samples of the exchange reaction. The deuterium labelling information can be sub-localized to regions in the protein by pepsin digestion under quench conditions and following the mass increase of the resulting peptides. One use of HX-MS is to probe for sites involved in molecular interactions by identifying regions of reduced hydrogen exchange upon protein-protein complex formation. Usually, binding interfaces will be revealed by marked reductions in hydrogen exchange due to steric exclusion of solvent. Protein-protein complex formation may be detected by HX-MS simply by measuring the total amount of deuterium incorporated in either protein members in the presence and absence of the respective binding partner as a function of time. The HX-MS technique uses the native components, i.e. protein and antibody or Fab fragment, and is performed in solution. Thus HX-MS provides the possibility for mimicking the in vivo conditions (Mass Spectrom. Rev. 25, 158 (2006). FVIII (Haemophilia 2010, 16; 349-359) and the antibodies KM33 and 4F30, (see example 14) were buffer ex-changed into 20 mM Imidazole, 10 mM $CaCl_2$, 150 mM NaCl, pH 7.3, before analysis. The HX experiments were automated by a Leap robot (H/D-x PAL; Leap Technologies Inc.) operated by the LEAPShell software (Leap Technologies Inc.), which performed initiation of the deuterium exchange reaction, reaction time control, quench reaction, injection onto the UPLC system and digestion time control. The Leap robot was equipped with two temperature controlled stacks maintained at 20° C. for buffer storage and HX reactions and maintained at 2° C. for storage of protein and quench solution, respectively. The Leap robot furthermore contained a cooled Trio VS unit (Leap Technologies Inc.) holding the pepsin-, pre- and analytical columns, and the LC tubing and switching valves at 1° C. The switching valves have been upgraded from HPLC to Microbore UHPLC switch valves (Cheminert, VICI AG). For the inline pepsin digestion, 100 μL quenched sample containing 0.15 pmol FVIII was loaded and passed over a Poroszyme® Immobilized Pepsin Cartridge (2.1×30 mm, Applied Biosystems)

using a isocratic flow rate of 200 μL/min (0.1% formic acid:CH$_3$OH 95:5). The resulting peptides were trapped and desalted on a VanGuard pre-column BEH C18 1.7 μm (2.1×5 mm, Waters Inc.). Subsequently, the valves were switched to place the pre-column inline with the analytical column, UPLC®-BEH C18 1.7 μm (2.1×100 mm, Waters Inc.), and the peptides separated using a 9 min gradient of 15-40% B delivered at 150 μL/min from an AQUITY UPLC® system (Waters Inc.). The mobile phases consisted of A: 0.1% formic acid and B: 0.1% formic acid in CH$_3$CN. The ESI MS data, and the elevated energy (MS$^E$) experiments were acquired in positive ion mode using a Q-Tof Premier MS (Waters Inc.). Leucine-enkephalin was used as the lock mass ([M+H]$^+$ ion at m/z 556.2771) and data was collected in continuum mode. Peptic peptides were identified in separate experiments using MS$^E$ methods (Waters Inc.). MS$^E$ data were processed using BiopharmaLynx 1.2 (version 017). HX-MS raw data files were subjected to continuous lock-mass-correction. Data analysis, i.e., centroid determination of deuterated peptides and plotting of in-exchange curves, was performed using HX-Express (Version Beta; J. Am. Soc. Mass Spectrom. 2006; 17: 1700).

Amide hydrogen/deuterium exchange (HX) was initiated by preparation of FVIII solutions in a concentration of 30 μM in the absence or presence of either 4F30, or KM33 into the corresponding deuterated buffer, i.e., 20 mM imidazole, 10 mM CaCl$_2$, 150 mM NaCl, prepared in D$_2$O, 98% D$_2$O final, pH 7.3 (uncorrected value)). All HX reactions were carried out at 20° C. and contained 3 μM FVIII in the absence or presence of excess FVIII mAbs (4.5 uM) to ensure saturation of FVIII with antibody. At appropriate time intervals ranging from 10 sec to 2 hours 46 min 40 s (10.000 s), aliquots of the HX reaction were quenched by an equal volume of ice-cold quenching buffer 1.35M TCEP (Tris(2-Carboxyethyl)-Phosphine Hydrochloride (Calbiochem®, EMD Chemicals inc.)) resulting in a final pH of 2.6 (uncorrected value).

The peptide map of the pepsin digestion of FVIII contained 653 peptides (>20 ionscore), which covered 82% of the N8 sequence.

Figure 3:
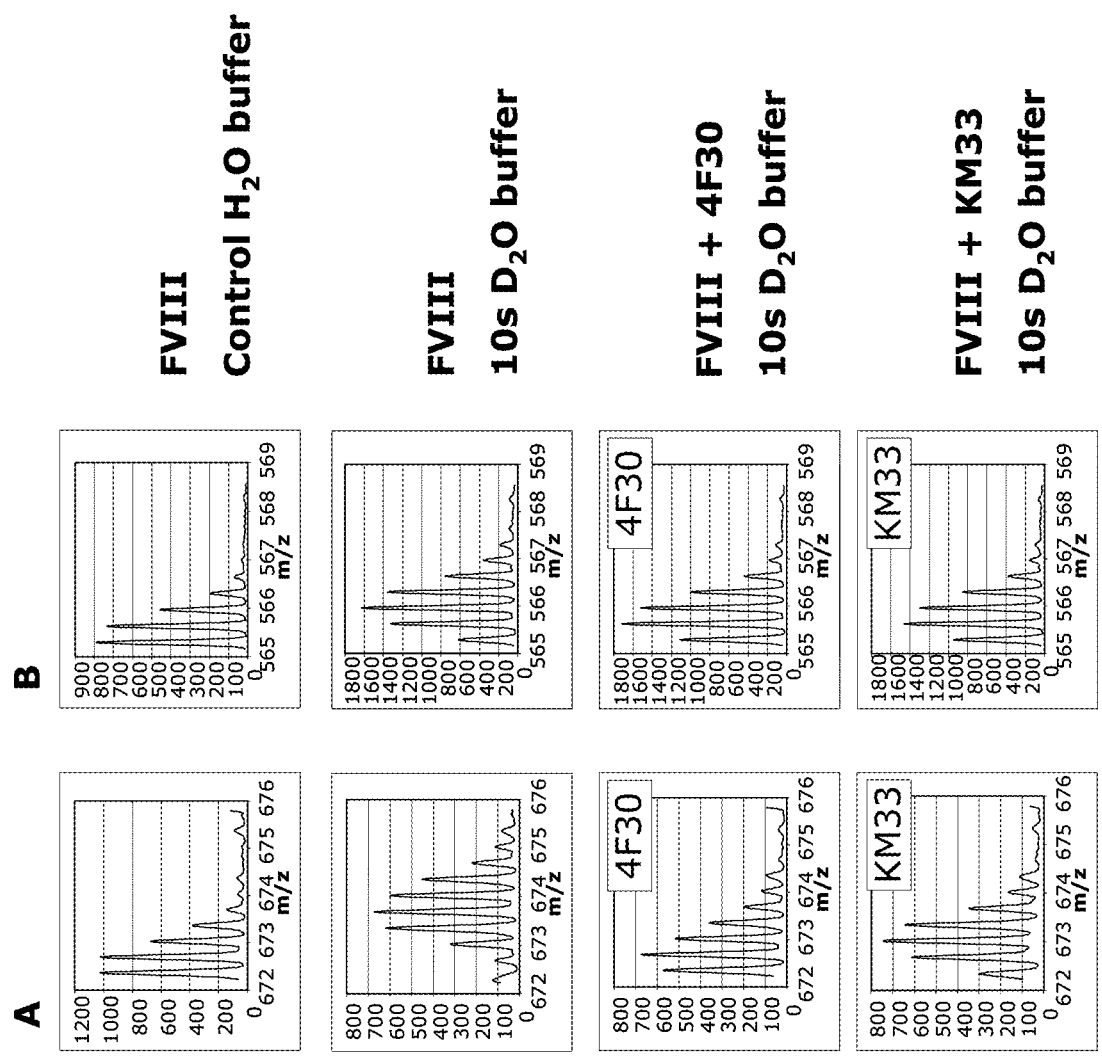
FIG. 3: Hydrogen exchange (HX) monitored by mass spectrometry identifies regions of FVIII involved in the 4F30 and KM33 binding (A) Mass/charge spectra corresponding to the peptide fragment 2078-2095, ($[M+H]^+$=672.3818, z=3), identified to be part of the epitope of both 4F30 and KM33 binding to FVIII. (B) Mass/charge spectra corresponding to the peptide fragment 2148-2161, (m/z=565.6554, z=3), identified to be part of the epitope of both 4F30 and KM33 binding to FVIII. For all spectra the upper panels show the non-deuterated controls, second, panel shows the peptide after 10 sec in-exchange with $D_2O$ in the absence ligand, third and fourth panels show the peptide after 10 sec in-exchange with $D_2O$ in the presence of 4F30 and KM33, respectively.
Figure 4:
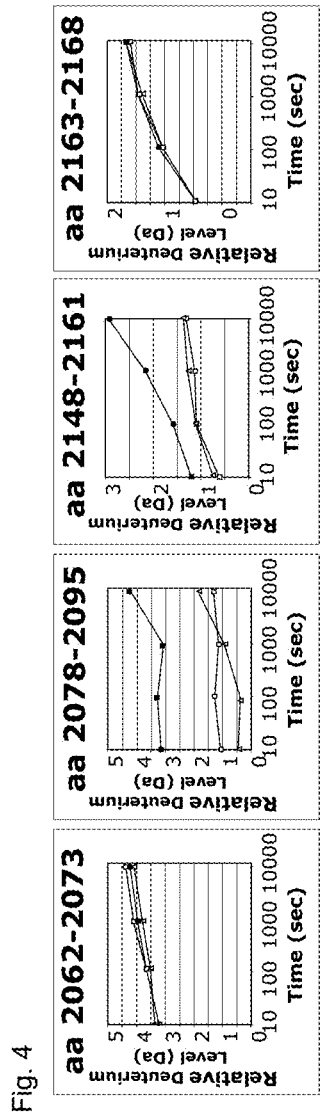
FIG. 4: Hydrogen exchange time-plots of representative peptides of FVIII in the presence of both 4F30 and KM33. Deuterium incorporation (Da) of FVIII peptides is plotted against time on a logarithmic scale in the absence (solid square) or presence of either 4F30 (open triangle) or KM33 (open square). Peptides covering residues aa 2062-2073 and 2163-2168 represent regions of FVIII that are unaffected by complex formation with both 4F30 and KM33. Peptides covering residues aa 2078-2095, and 2148-2161 represent regions of FVIII that are part of the binding epitope of both 4F30 and KM33.
Figure 5:
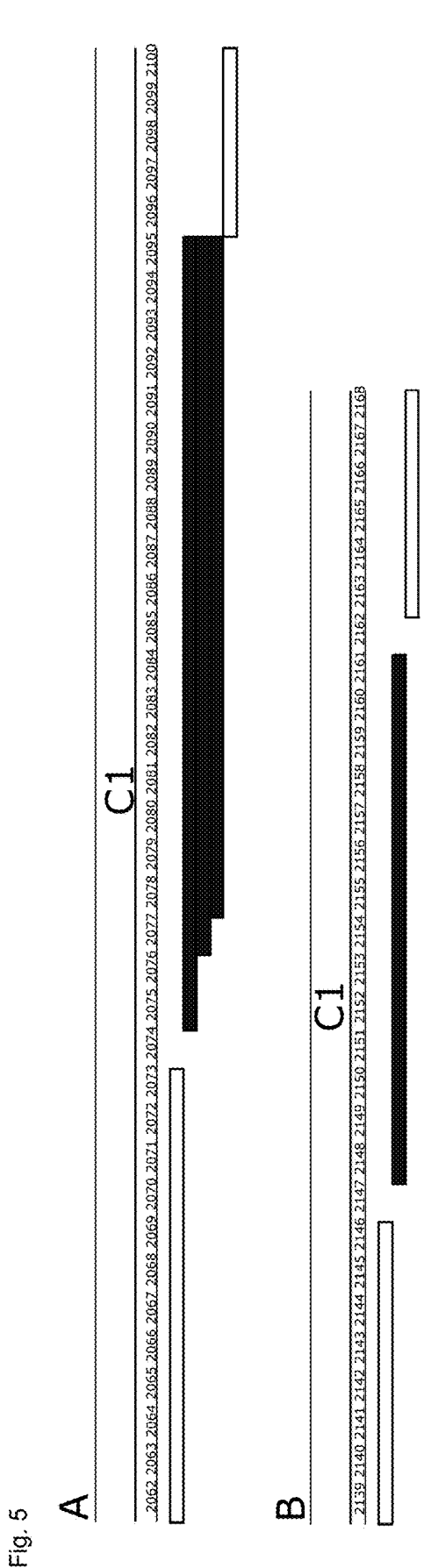
FIG. 5: Sequence coverage of HX analyzed peptides of FVIII in the presence of KM33 and 4F30. The primary sequence (using mature numbering; horizontal panel A: aa 2062-2100 and horizontal panel B: aa 2139-2168) is displayed above the HX analyzed peptides (shown as horizontal bars). Peptides showing similar exchange patterns both in the presence and absence of both 4F30 and KM33 are displayed with no fills (open bars) whereas peptides showing reduced deuterium incorporation upon of both 4F30 and KM33 binding are filled in black (closed bars).

The deuterium incorporation rate (HX time-course) of 653 peptides, covering 82% of the primary sequence of FVIII, were monitored in the presence and absence of KM33 at 4 time points, i.e., 10 s, 100 s, 1,000 s, and 10,000 s (FIGS. 3A, 4, 5).

The observed exchange pattern in the presence or absence of KM33 may be divided into two groups: One group of peptides display an exchange pattern that is unaffected by the binding of both 4F30 and KM33 (FIG. 4 [aa 2062-2073 and 2163-2168]), which comprises 99.2% of the peptides. In contrast, another group of FVIII peptic peptides show protection from exchange upon with both 4F30 and KM33 (FIG. 4), which includes 0.8% of the peptic peptides. For example at 100 s exchange with D$_2$O, approximately 1 amide is protected from exchange in the region aa 2148-2161 upon both 4F30 and KM33 binding (FIG. 4). The region displaying protection upon KM33 binding includes 4 peptic peptides covering residues aa 2075-2095, 2077-2095, 2078-2095 and 2148-2161. Thus the epitope of both 4F30 and KM33 are to be found within the linear sequences aa 2075-2095 and 2148-2161 (using mature numbering). The epitope map-ping of 4F30 and KM33 to FVIII revealed the two ligands to have identical epitopes. While it has previously been described that K2092-S2094 are involved in the epitope of KM33 (see references in table 13), the remaining part of the epitope has not been identified.

Example 18: Introduction of a Glycan in FVIII-R2159N Block Binding to an Anti-C1 Domain Antibody (KM33) which Prolongs FVIII Cellular Uptake and In Vivo Half-Life Replacement of R2159 by asparagine in the C1 domain region 2157-SIRST-2161 introduces a consensus sequence for N-linked glycosylation (i.e. N-X-S/T, see page 22) at position 2159 which is involved in the epitope of KM33 (see example 17). FVIII-R2159N was constructed employing QuickChange mutagenesis using the DNA of wt FVIII as a template (Blood 2009; 133:3102-3109). FVIII-R2159N and wt FVIII were expressed as described (Plos One 2011; 6(8):e24163. doi:10.1371/journal.pone.0024163). The introduction of the additional N-linked glycan in the FVIII light chain was confirmed by SDS-PAGE, where a reduced mobility of the FVIII light chain was observed. FVIII activity was measured in a chromogenic FVIII assay as described in example 3. FVIII antigen was measured in an ELISA using CLB-EL14 IgG4 (Br J Haematol 2008; 142: 644-652) as capture antibody, peroxidase-labelled CLB-CAg69 (Biochem J 1989; 263: 187-94) as a detection antibody, and human pooled plasma from 40 donors as a standard. Association of antibody KM33 (see example 15) to wt FVIII and FVIII-R2159N was assessed by SPR analysis employing a BIAcore 3000 biosensor (Biacore AB, Uppsala, Sweden). Anti-C2 antibody CLB-EL14 IgG4 was immobilized onto a CM5 sensor chip to a density of 33 fmol/mm$^2$ employing the amine coupling method according to the manufacturer's instructions.

Subsequently, FVIII-R2159N or wt FVIII was bound to EL14 IgG4 to a density of 3 fmol/mm$^2$. KM33 (100 nM) was passed over FVIII-R2159N or wt FVIII in a buffer containing 150 mM NaCl, 5 mM CaCl2, 0.005% (v/v) TWEEN 20 and 20 mM HEPES (pH 7.4) at 25° C. with a flow rate of 20 μL/min. The binding response was recorded during 240 seconds of association and corrected for non-specific binding. Table 15 shows the binding response after 235 seconds of association as well as the activity and antigen concentration of wt FVIII and FVIII-R2159N. The results show that introduction of the glycan completely abolishes the binding of FVIII to KM33 while the activity of FVIII is not impaired by the introduction of the glycan. As KM33 binding to FVIII reduces cellular uptake and prolong in vivo half-life, it is likely that FVIII-R2159N showing abolished KM33 binding also will display reduced cellular uptake and prolonged in vivo half-life.

TABLE 15

Activity and KM33 binding wt FVIII and FVIII-R2159N

| FVIII variant | Activity (U/ml) | Antigen (U/ml) | Activity/ antigen ratio | Binding Response (RU) of KM33 after 235 seconds of association to the FVIII variant. |
|---|---|---|---|---|
| wt FVIII | 1.05 | 1.71 | 0.62 | 154 |
| FVIII-R2159N | 0.41 | 0.52 | 0.79 | 0 |

Example 19: Prolongation of Liver Clearance of FVIII K2062A-F2093A

Liver clearance of FVIII-K2092A-F2093F was evaluated in a perfused liver model (Thromb Haemost 2010; 104, 243-251). Briefly, the livers of anesthetized Sprague Dawley rats were cannulated via the portal vein and vena cava and perfused with Krebs-Henseleit bicarbonate buffer (115 mM NaCl, 25 mM NaHCO$_3$, 5.9 mM KCl, 1.2 mM MgSO$_4$, 1.2 mM, KH$_2$PO$_4$, 2.5 mM CaCl$_2$) at 25 ml/min. Before entering the liver, the perfusate flows through a fiberdialyser (Gambro® Scandidact Hemophan® Fiber Dialyzer 100HG, Secon, Dransfeld, Germany) which is saturated with an oxygen:carbon dioxide mixture (95:5). FVIII (Haemophilia 2010, 16; 349-359) or FVIII-K2092A-F2093A was added to the buffer and mixed before samples taken from the recirculating perfusate at time points from 0 to 80 min. FVIII:C in the perfusate was analyzed by a chromogenic assay as described in example 3. The T % of FVIII-K2092A-F2093A was prolonged as compared to that of wild-type FVIII (Table 16) demonstrating a decreased liver clearance of FVIII-K2092A-F2093A as compared to FVIII without C1 substitutions.

TABLE 16

Clearance of FVIII and FVIII-K2092A-F2093A in perfused rat livers.

| FVIII variant | T½ (min)[1] |
|---|---|
| Wild-type FVIII | 31 ± 3 |
| FVIII-K2092A-F2093A | 113 ± 48 |

[1]Data are mean and standard deviation of n = 3 experiments.

Example 20: Prolongation of In Vivo Half-Life of FVIII-K2092A-F2093A

In vivo pharmacokinetics of the K2093A-F2093A mutant was further evaluated in VWF-deficient mice. Wildtype FVIII (Haemophilia 2010, 16; 349-359) and FVIII-K2092A-F2093A was 40K-PEGylated specific on an O-linked glycan in the B-domain as described in WO09108806. wt FVIII, K2092-F2093A and PEGylated FVIII (40K-PEG-FVIII) and mutant (40K-PEG-K2092A-F2093A) were administered to VWF-deficient mice at a dose of 280 IU/kg (n=3-6 per group) as described in example 16. Blood samples were taken at three time points from each mice, i.e. at t=0.5, 1.25 and 2 h post dosing for FVIII and K2092-F2093A and 4, 7 and 24 h post dosing for the PEGylated proteins, and analyzed for FVIII:C as described in example 3. The C1 mutations K2092A-F20963A resulted in approximately a doubling of T % both for the PEGylated as well as for the non-PEGylated FVIII proteins (Table 17) thus confirming that substitution of K2092-F2093 in FVIII resulted in prolonged in vivo half-life.

TABLE 17

Influence of the K2092-F2093A mutation on in vivo half-life.

| | T½ (h) | |
|---|---|---|
| Test compound | mean | 95% conficence intervals |
| wt FVIII | 0.3 | 0.3-0.4 |
| K2092A-F2093A | 0.6 | 0.5-0.8 |
| 40K-PEG-FVIII | 6.5 | 4.9-9.5 |
| 40K-PEG-FVIII-K2092A-F2093A | 10.5 | 9.6-11.7 |

Example 18: Reduced T-Cell Response of FVIII-R2090A-K2092A-F2093A

It is well-established that the interaction of FVIII with antigen presenting cells provides a crucial step in the formation of FVIII specific CD4+ T cells which subsequently stimulate the production of antibodies directed towards FVIII. The CD4+ T cell responses of splenocytes from mice injected with wild type FVIII (wt FVIII) and FVIII-R2090A-K2092A-F2093A were analyzed as follows: Spleens collected after weekly injections of FVIII were pooled within the groups.

Erythrocytes were removed and CD8+ cells were depleted by magnetic bead separation using beads coated with the anti-mouse CD8 antibody Lyt 1.2 (eBioscience). Remaining $CD8^-$ cells were cultured in round-bottomed 96-well plates for 72 or 96 hours in X-VIVO 15 medium supplemented with 100 U/ml penicillin, 100 mg/ml streptomycin (all from BioWhittaker; Walkersville, Md.) and 55 μM β-mercaptoethanol (Sigma-Aldrich, Irvine, UK) in presence of increasing FVIII concentration (0, 0.1, 0.5 or 1 μg/ml) to generate antigen-specific T cell proliferation or concanavalin A (1 μg/ml) to generate nonspecific proliferation. Proliferation was assayed by the addition of 1 ρCi/well of $[^3H]$ thymidine (ICN Pharmaceuticals, Irvine, Calif.) for the last 18-20 hours. The results shown in Table 18 are expressed in counts per minute (CPM) values (mean±SD) or as the stimulation index (SI: CPM of cells incubated with antigen divided by CPM of cells with medium alone). Injection of mice with FVIII-R2090-K2092A-F2093A led to significantly reduced proliferation of splenic $CD4^+$ T cells upon in vitro restimulation with FVIII when compared to wt FVIII showing that the reduced uptake of FVIII-R2090A-K2092A-F2093A in antigen presenting cells translates into a reduction of CD4+ T cell responses in mice.

TABLE 18

CD4+ T cell responses of splenocytes derived from mice treated with 5 intravenous injections of FVIII WT and FVIII-R2090A-K2092A-F2093A.

| | FVIII concentration (ug/ml) | | | | |
|---|---|---|---|---|---|
| | 0 | 0.1 | 0.5 | 1.0 | ConA |
| Proliferation after 72 h (CPM): | | | | | |
| wt FVIII | 1169 ± 193 | 4052 ± 1309 | 6731 ± 838 | 8437 ± 865 | 77892 ± 6623 |
| FVIII-R2090A-K2092A-F2093A | 1352 ± 383 | 2464 ± 433 | 2908 ± 376 | 3226 ± 656 | 66944 ± 13127 |

TABLE 18-continued CD4+ T cell responses of splenocytes derived from mice treated
with 5 intravenous injections of FVIII WT and FVIII-R2090A-K2092A-F2093A.

| | FVIII concentration (ug/ml) | | | | |
|---|---|---|---|---|---|
| | 0 | 0.1 | 0.5 | 1.0 | ConA |
| Proliferation after 72 h (SI): | | | | | |
| wt FVIII | 1.0 | 4.12 ± 0.01 | 5.76 ± 0.71 | 7.22 ± 0.74 | 48.29 ± 0.74 |
| FVIII-R2090A-K2092A-F2093A | 1.0 | 1.82 ± 0.32 | 2.15 ± 0.28 | 2.39 ± 0.49 | 48.64 ± 9.34 |
| Proliferation after 96 h (CPM): | | | | | |
| wt FVIII | 1496 ± 380 | 7755 ± 1346 | 13722 ± 1598 | 15766 ± 2664 | 37699 ± 2660 |
| FVIII-R2090A-K2092A-F2093A | 1435 ± 229 | 4069 ± 723 | 5841 ± 680 | 6110 ± 300 | 46531 ± 4917 |
| Proliferation after 96 h (SI): | | | | | |
| wt FVIII | 1.0 | 4.12 ± 0.01 | 5.76 ± 0.71 | 7.22 ± 0.74 | 48.29 ± 0.74 |
| FVIII-R2090A-K2092A-F2093A | 1.0 | 1.82 ± 0.32 | 2.15 ± 0.28 | 2.39 ± 0.49 | 48.64 ± 9.34 |

Example 22: Reduced Level of Antibodies in Mice Receiving FVIII-R2090A-K2092A-F2093A The consequence of the reduced uptake of FVIII variants by antigen presenting cells on immunogenicity of these variants was furthermore assessed in a murine model for inhibitor formation in hemophilia A. Wildtype FVIII and FVIII-R2090A-K2092A-F2093A were diluted to 10 µg/ml in sterile PBS and a dose of 100 µl (1 µg) was administered intravenously (i.v.) in male FVIII exon 17 KO mice (n=8) five times weekly. One week after the last injection animals were sacrificed and blood samples were collected. The presence of anti-FVIII antibodies in plasma samples from treated FVIII-KO mice was determined by enzyme-linked immunosorbant assay (ELISA) and Bethesda assay measuring the ability of the mice plasma to inhibit FVIII activity. For the ELISA, plasma derived FVIII (5 µg/ml) in buffer containing 50 mM $NaHCO_3$ pH 9.8 was immobilized in microtiter wells. Plates were blocked with 2% gelatin in PBS. Mouse plasma dilutions were prepared in 50 mM Tris, 150 mM NaCl, 2% BSA, pH 7.4. Mouse monoclonal anti-FVIII antibody CLB-CAg9 was used as a standard. Anti-FVIII antibodies were detected with goat anti-mouse IgG-HRP. The concentration of anti-FVIII antibodies in murine plasma are displayed in arbitrary units (AU), where 1 AU corresponds to signal obtained by 1 µg of CLB-CAg9. The Bethesda assay was performed essentially as described (Thromb Diath Haemorrh 1975; 34: 612). Data was analyzed using non-parametric Mann-Whitney U-test. The antibody titers observed in mouse plasma following 5 weekly injections of FVIII and FVIII-R2090A-K2092A-F2093A are displayed in Table 19. The results show that infusion of FVIII results in the formation of antibodies directed towards FVIII. A significant reduction in antibody titers is observed in mice treated with FVIII-R2090A-K2092A-F2093A ($p<0.05$). Also the Bethesda titer reflecting the presence of neutralizing anti FVIII antibodies were significantly reduced ($p<0.05$). These findings show that the reduced uptake of FVIII-R2090A-K2092A-F2093A in antigen presenting cells and the reduced T-cell response translates into a reduction of inhibitor titres in a murine model for inhibitor development in hemophilia A. Together, these results show that specific modification of FVIII leading to reduction in its endocytosis by antigen presenting cells, is an effective way to reduce FVIII immunogenicity in vivo. Our results therefore suggest that FVIII variants that display a reduced cellular uptake carry a reduced risk of inhibitor development in patients with hemophilia A.

TABLE 19

Antibody titers in plasma of mice treated with 5 intravenous injections of FVIII and FVIII-R2090A-K2092A-F2093A.

| FVIII variant | ELISA (AU)[1] | Bethesda titer (BU/ml)[1] |
|---|---|---|
| FVIII WT | 252200 ± 81840 | 364 ± 98 |
| FVIII-R2090A-K2092A-F2093A | 81910 ± 11690 | 118 ± 48 |

[1]Results are mean ± SEM of data from 8 animals.

The invention claimed is:

1. A recombinant Factor VIII (FVIII) variant having FVIII activity, wherein the recombinant FVIII variant consists of an amino acid sequence selected from the group consisting of SEQ ID NOs: 4, 5, 7 and 8.

2. A pharmaceutical composition comprising a recombinant FVIII variant according to claim 1.

3. A method for treating hemophilia comprising administering the recombinant FVIII variant according to claim 1 to a subject in need thereof.

4. A conjugate comprising the recombinant FVIII variant of claim 1 and a half-life extending agent selected from the group consisting of polyethylene glycol (PEG), poly sialic acid (PSA), and heparosan (HEP).

5. A pharmaceutical composition comprising the conjugate according to claim 4.

6. A method for treating hemophilia comprising administering the conjugate according to claim 4 to a subject in need thereof.

* * * * *

SEQUENCE LISTING

```
<160> NUMBER OF SEQ ID NOS: 9

<210> SEQ ID NO 1
<211> LENGTH: 2332
<212> TYPE: PRT
<213> ORGANISM: homo sapiens

<400> SEQUENCE: 1

Ala Thr Arg Arg Tyr Tyr Leu Gly Ala Val Glu Leu Ser Trp Asp Tyr
1               5                   10                  15

Met Gln Ser Asp Leu Gly Glu Leu Pro Val Asp Ala Arg Phe Pro Pro
            20                  25                  30
```

-continued

```
Arg Val Pro Lys Ser Phe Pro Phe Asn Thr Ser Val Tyr Lys Lys
         35                  40                  45
Thr Leu Phe Val Glu Phe Thr Asp His Leu Phe Asn Ile Ala Lys Pro
 50                  55                  60
Arg Pro Pro Trp Met Gly Leu Leu Gly Pro Thr Ile Gln Ala Glu Val
 65                  70                  75                  80
Tyr Asp Thr Val Val Ile Thr Leu Lys Asn Met Ala Ser His Pro Val
                     85                  90                  95
Ser Leu His Ala Val Gly Val Ser Tyr Trp Lys Ala Ser Glu Gly Ala
                100                 105                 110
Glu Tyr Asp Asp Gln Thr Ser Gln Arg Glu Lys Glu Asp Asp Lys Val
                115                 120                 125
Phe Pro Gly Gly Ser His Thr Tyr Val Trp Gln Val Leu Lys Glu Asn
130                 135                 140
Gly Pro Met Ala Ser Asp Pro Leu Cys Leu Thr Tyr Ser Tyr Leu Ser
145                 150                 155                 160
His Val Asp Leu Val Lys Asp Leu Asn Ser Gly Leu Ile Gly Ala Leu
                165                 170                 175
Leu Val Cys Arg Glu Gly Ser Leu Ala Lys Glu Lys Thr Gln Thr Leu
                180                 185                 190
His Lys Phe Ile Leu Leu Phe Ala Val Phe Asp Glu Gly Lys Ser Trp
            195                 200                 205
His Ser Glu Thr Lys Asn Ser Leu Met Gln Asp Arg Asp Ala Ala Ser
            210                 215                 220
Ala Arg Ala Trp Pro Lys Met His Thr Val Asn Gly Tyr Val Asn Arg
225                 230                 235                 240
Ser Leu Pro Gly Leu Ile Gly Cys His Arg Lys Ser Val Tyr Trp His
                245                 250                 255
Val Ile Gly Met Gly Thr Thr Pro Glu Val His Ser Ile Phe Leu Glu
                260                 265                 270
Gly His Thr Phe Leu Val Arg Asn His Arg Gln Ala Ser Leu Glu Ile
            275                 280                 285
Ser Pro Ile Thr Phe Leu Thr Ala Gln Thr Leu Leu Met Asp Leu Gly
            290                 295                 300
Gln Phe Leu Leu Phe Cys His Ile Ser Ser His Gln His Asp Gly Met
305                 310                 315                 320
Glu Ala Tyr Val Lys Val Asp Ser Cys Pro Glu Glu Pro Gln Leu Arg
                325                 330                 335
Met Lys Asn Asn Glu Glu Ala Glu Asp Tyr Asp Asp Asp Leu Thr Asp
                340                 345                 350
Ser Glu Met Asp Val Val Arg Phe Asp Asp Asp Asn Ser Pro Ser Phe
            355                 360                 365
Ile Gln Ile Arg Ser Val Ala Lys Lys His Pro Lys Thr Trp Val His
            370                 375                 380
Tyr Ile Ala Ala Glu Glu Asp Trp Asp Tyr Ala Pro Leu Val Leu
385                 390                 395                 400
Ala Pro Asp Asp Arg Ser Tyr Lys Ser Gln Tyr Leu Asn Asn Gly Pro
                405                 410                 415
Gln Arg Ile Gly Arg Lys Tyr Lys Lys Val Arg Phe Met Ala Tyr Thr
            420                 425                 430
Asp Glu Thr Phe Lys Thr Arg Glu Ala Ile Gln His Glu Ser Gly Ile
            435                 440                 445
```

```
Leu Gly Pro Leu Leu Tyr Gly Glu Val Gly Asp Thr Leu Ile Ile
    450                 455                 460

Phe Lys Asn Gln Ala Ser Arg Pro Tyr Asn Ile Tyr Pro His Gly Ile
465                 470                 475                 480

Thr Asp Val Arg Pro Leu Tyr Ser Arg Arg Leu Pro Lys Gly Val Lys
                485                 490                 495

His Leu Lys Asp Phe Pro Ile Leu Pro Gly Glu Ile Phe Lys Tyr Lys
            500                 505                 510

Trp Thr Val Thr Val Glu Asp Gly Pro Thr Lys Ser Asp Pro Arg Cys
            515                 520                 525

Leu Thr Arg Tyr Tyr Ser Ser Phe Val Asn Met Glu Arg Asp Leu Ala
    530                 535                 540

Ser Gly Leu Ile Gly Pro Leu Leu Ile Cys Tyr Lys Glu Ser Val Asp
545                 550                 555                 560

Gln Arg Gly Asn Gln Ile Met Ser Asp Lys Arg Asn Val Ile Leu Phe
                565                 570                 575

Ser Val Phe Asp Glu Asn Arg Ser Trp Tyr Leu Thr Glu Asn Ile Gln
            580                 585                 590

Arg Phe Leu Pro Asn Pro Ala Gly Val Gln Leu Glu Asp Pro Glu Phe
    595                 600                 605

Gln Ala Ser Asn Ile Met His Ser Ile Asn Gly Tyr Val Phe Asp Ser
    610                 615                 620

Leu Gln Leu Ser Val Cys Leu His Glu Val Ala Tyr Trp Tyr Ile Leu
625                 630                 635                 640

Ser Ile Gly Ala Gln Thr Asp Phe Leu Ser Val Phe Phe Ser Gly Tyr
                645                 650                 655

Thr Phe Lys His Lys Met Val Tyr Glu Asp Thr Leu Thr Leu Phe Pro
            660                 665                 670

Phe Ser Gly Glu Thr Val Phe Met Ser Met Glu Asn Pro Gly Leu Trp
    675                 680                 685

Ile Leu Gly Cys His Asn Ser Asp Phe Arg Asn Arg Gly Met Thr Ala
    690                 695                 700

Leu Leu Lys Val Ser Ser Cys Asp Lys Asn Thr Gly Asp Tyr Tyr Glu
705                 710                 715                 720

Asp Ser Tyr Glu Asp Ile Ser Ala Tyr Leu Leu Ser Lys Asn Asn Ala
                725                 730                 735

Ile Glu Pro Arg Ser Phe Ser Gln Asn Ser Arg His Pro Ser Thr Arg
            740                 745                 750

Gln Lys Gln Phe Asn Ala Thr Thr Ile Pro Glu Asn Asp Ile Glu Lys
    755                 760                 765

Thr Asp Pro Trp Phe Ala His Arg Thr Pro Met Pro Lys Ile Gln Asn
    770                 775                 780

Val Ser Ser Ser Asp Leu Leu Met Leu Leu Arg Gln Ser Pro Thr Pro
785                 790                 795                 800

His Gly Leu Ser Leu Ser Asp Leu Gln Glu Ala Lys Tyr Glu Thr Phe
                805                 810                 815

Ser Asp Asp Pro Ser Pro Gly Ala Ile Asp Ser Asn Asn Ser Leu Ser
            820                 825                 830

Glu Met Thr His Phe Arg Pro Gln Leu His His Ser Gly Asp Met Val
    835                 840                 845

Phe Thr Pro Glu Ser Gly Leu Gln Leu Arg Leu Asn Glu Lys Leu Gly
    850                 855                 860
```

-continued

```
Thr Thr Ala Ala Thr Glu Leu Lys Lys Leu Asp Phe Lys Val Ser Ser
865                 870                 875                 880

Thr Ser Asn Asn Leu Ile Ser Thr Ile Pro Ser Asp Asn Leu Ala Ala
            885                 890                 895

Gly Thr Asp Asn Thr Ser Ser Leu Gly Pro Pro Ser Met Pro Val His
        900                 905                 910

Tyr Asp Ser Gln Leu Asp Thr Thr Leu Phe Gly Lys Lys Ser Ser Pro
            915                 920                 925

Leu Thr Glu Ser Gly Gly Pro Leu Ser Leu Ser Glu Asn Asn Asp
        930                 935                 940

Ser Lys Leu Leu Glu Ser Gly Leu Met Asn Ser Gln Glu Ser Ser Trp
945                 950                 955                 960

Gly Lys Asn Val Ser Ser Thr Glu Ser Gly Arg Leu Phe Lys Gly Lys
            965                 970                 975

Arg Ala His Gly Pro Ala Leu Leu Thr Lys Asp Asn Ala Leu Phe Lys
            980                 985                 990

Val Ser Ile Ser Leu Leu Lys Thr  Asn Lys Thr Ser Asn  Asn Ser Ala
            995                 1000                1005

Thr Asn  Arg Lys Thr His Ile  Asp Gly Pro Ser Leu  Leu Ile Glu
    1010                1015                1020

Asn Ser  Pro Ser Val Trp Gln  Asn Ile Leu Glu Ser  Asp Thr Glu
    1025                1030                1035

Phe Lys  Lys Val Thr Pro Leu  Ile His Asp Arg Met  Leu Met Asp
    1040                1045                1050

Lys Asn  Ala Thr Ala Leu Arg  Leu Asn His Met Ser  Asn Lys Thr
    1055                1060                1065

Thr Ser  Ser Lys Asn Met Glu  Met Val Gln Gln Lys  Lys Glu Gly
    1070                1075                1080

Pro Ile  Pro Pro Asp Ala Gln  Asn Pro Asp Met Ser  Phe Phe Lys
    1085                1090                1095

Met Leu  Phe Leu Pro Glu Ser  Ala Arg Trp Ile Gln  Arg Thr His
    1100                1105                1110

Gly Lys  Asn Ser Leu Asn Ser  Gly Gln Gly Pro Ser  Pro Lys Gln
    1115                1120                1125

Leu Val  Ser Leu Gly Pro Glu  Lys Ser Val Glu Gly  Gln Asn Phe
    1130                1135                1140

Leu Ser  Glu Lys Asn Lys Val  Val Val Gly Lys Gly  Glu Phe Thr
    1145                1150                1155

Lys Asp  Val Gly Leu Lys Glu  Met Val Phe Pro Ser  Ser Arg Asn
    1160                1165                1170

Leu Phe  Leu Thr Asn Leu Asp  Asn Leu His Glu Asn  Asn Thr His
    1175                1180                1185

Asn Gln  Glu Lys Lys Ile Gln  Glu Glu Ile Glu Lys  Lys Glu Thr
    1190                1195                1200

Leu Ile  Gln Glu Asn Val Val  Leu Pro Gln Ile His  Thr Val Thr
    1205                1210                1215

Gly Thr  Lys Asn Phe Met Lys  Asn Leu Phe Leu Leu  Ser Thr Arg
    1220                1225                1230

Gln Asn  Val Glu Gly Ser Tyr  Asp Gly Ala Tyr Ala  Pro Val Leu
    1235                1240                1245

Gln Asp  Phe Arg Ser Leu Asn  Asp Ser Thr Asn Arg  Thr Lys Lys
    1250                1255                1260
```

```
His Thr Ala His Phe Ser Lys Lys Gly Glu Glu Glu Asn Leu Glu
1265                1270                1275

Gly Leu Gly Asn Gln Thr Lys Gln Ile Val Glu Lys Tyr Ala Cys
    1280                1285                1290

Thr Thr Arg Ile Ser Pro Asn Thr Ser Gln Gln Asn Phe Val Thr
1295                1300                1305

Gln Arg Ser Lys Arg Ala Leu Lys Gln Phe Arg Leu Pro Leu Glu
1310                1315                1320

Glu Thr Glu Leu Glu Lys Arg Ile Ile Val Asp Asp Thr Ser Thr
    1325                1330                1335

Gln Trp Ser Lys Asn Met Lys His Leu Thr Pro Ser Thr Leu Thr
1340                1345                1350

Gln Ile Asp Tyr Asn Glu Lys Glu Lys Gly Ala Ile Thr Gln Ser
1355                1360                1365

Pro Leu Ser Asp Cys Leu Thr Arg Ser His Ser Ile Pro Gln Ala
1370                1375                1380

Asn Arg Ser Pro Leu Pro Ile Ala Lys Val Ser Ser Phe Pro Ser
    1385                1390                1395

Ile Arg Pro Ile Tyr Leu Thr Arg Val Leu Phe Gln Asp Asn Ser
1400                1405                1410

Ser His Leu Pro Ala Ala Ser Tyr Arg Lys Lys Asp Ser Gly Val
1415                1420                1425

Gln Glu Ser Ser His Phe Leu Gln Gly Ala Lys Lys Asn Asn Leu
    1430                1435                1440

Ser Leu Ala Ile Leu Thr Leu Glu Met Thr Gly Asp Gln Arg Glu
1445                1450                1455

Val Gly Ser Leu Gly Thr Ser Ala Thr Asn Ser Val Thr Tyr Lys
1460                1465                1470

Lys Val Glu Asn Thr Val Leu Pro Lys Pro Asp Leu Pro Lys Thr
    1475                1480                1485

Ser Gly Lys Val Glu Leu Leu Pro Lys Val His Ile Tyr Gln Lys
1490                1495                1500

Asp Leu Phe Pro Thr Glu Thr Ser Asn Gly Ser Pro Gly His Leu
1505                1510                1515

Asp Leu Val Glu Gly Ser Leu Leu Gln Gly Thr Glu Gly Ala Ile
    1520                1525                1530

Lys Trp Asn Glu Ala Asn Arg Pro Gly Lys Val Pro Phe Leu Arg
1535                1540                1545

Val Ala Thr Glu Ser Ser Ala Lys Thr Pro Ser Lys Leu Leu Asp
1550                1555                1560

Pro Leu Ala Trp Asp Asn His Tyr Gly Thr Gln Ile Pro Lys Glu
    1565                1570                1575

Glu Trp Lys Ser Gln Glu Lys Ser Pro Glu Lys Thr Ala Phe Lys
1580                1585                1590

Lys Lys Asp Thr Ile Leu Ser Leu Asn Ala Cys Glu Ser Asn His
1595                1600                1605

Ala Ile Ala Ala Ile Asn Glu Gly Gln Asn Lys Pro Glu Ile Glu
    1610                1615                1620

Val Thr Trp Ala Lys Gln Gly Arg Thr Glu Arg Leu Cys Ser Gln
1625                1630                1635

Asn Pro Pro Val Leu Lys Arg His Gln Arg Glu Ile Thr Arg Thr
1640                1645                1650
```

```
Thr Leu Gln Ser Asp Gln Glu Glu Ile Asp Tyr Asp Asp Thr Ile
1655                1660                1665

Ser Val Glu Met Lys Lys Glu Asp Phe Asp Ile Tyr Asp Glu Asp
1670                1675                1680

Glu Asn Gln Ser Pro Arg Ser Phe Gln Lys Lys Thr Arg His Tyr
1685                1690                1695

Phe Ile Ala Ala Val Glu Arg Leu Trp Asp Tyr Gly Met Ser Ser
1700                1705                1710

Ser Pro His Val Leu Arg Asn Arg Ala Gln Ser Gly Ser Val Pro
1715                1720                1725

Gln Phe Lys Lys Val Val Phe Gln Glu Phe Thr Asp Gly Ser Phe
1730                1735                1740

Thr Gln Pro Leu Tyr Arg Gly Glu Leu Asn Glu His Leu Gly Leu
1745                1750                1755

Leu Gly Pro Tyr Ile Arg Ala Glu Val Glu Asp Asn Ile Met Val
1760                1765                1770

Thr Phe Arg Asn Gln Ala Ser Arg Pro Tyr Ser Phe Tyr Ser Ser
1775                1780                1785

Leu Ile Ser Tyr Glu Glu Asp Gln Arg Gln Gly Ala Glu Pro Arg
1790                1795                1800

Lys Asn Phe Val Lys Pro Asn Glu Thr Lys Thr Tyr Phe Trp Lys
1805                1810                1815

Val Gln His His Met Ala Pro Thr Lys Asp Glu Phe Asp Cys Lys
1820                1825                1830

Ala Trp Ala Tyr Phe Ser Asp Val Asp Leu Glu Lys Asp Val His
1835                1840                1845

Ser Gly Leu Ile Gly Pro Leu Leu Val Cys His Thr Asn Thr Leu
1850                1855                1860

Asn Pro Ala His Gly Arg Gln Val Thr Val Gln Glu Phe Ala Leu
1865                1870                1875

Phe Phe Thr Ile Phe Asp Glu Thr Lys Ser Trp Tyr Phe Thr Glu
1880                1885                1890

Asn Met Glu Arg Asn Cys Arg Ala Pro Cys Asn Ile Gln Met Glu
1895                1900                1905

Asp Pro Thr Phe Lys Glu Asn Tyr Arg Phe His Ala Ile Asn Gly
1910                1915                1920

Tyr Ile Met Asp Thr Leu Pro Gly Leu Val Met Ala Gln Asp Gln
1925                1930                1935

Arg Ile Arg Trp Tyr Leu Leu Ser Met Gly Ser Asn Glu Asn Ile
1940                1945                1950

His Ser Ile His Phe Ser Gly His Val Phe Thr Val Arg Lys Lys
1955                1960                1965

Glu Glu Tyr Lys Met Ala Leu Tyr Asn Leu Tyr Pro Gly Val Phe
1970                1975                1980

Glu Thr Val Glu Met Leu Pro Ser Lys Ala Gly Ile Trp Arg Val
1985                1990                1995

Glu Cys Leu Ile Gly Glu His Leu His Ala Gly Met Ser Thr Leu
2000                2005                2010

Phe Leu Val Tyr Ser Asn Lys Cys Gln Thr Pro Leu Gly Met Ala
2015                2020                2025

Ser Gly His Ile Arg Asp Phe Gln Ile Thr Ala Ser Gly Gln Tyr
2030                2035                2040
```

```
Gly Gln Trp Ala Pro Lys Leu Ala Arg Leu His Tyr Ser Gly Ser
    2045                2050                2055

Ile Asn Ala Trp Ser Thr Lys Glu Pro Phe Ser Trp Ile Lys Val
    2060                2065                2070

Asp Leu Leu Ala Pro Met Ile Ile His Gly Ile Lys Thr Gln Gly
    2075                2080                2085

Ala Arg Gln Lys Phe Ser Ser Leu Tyr Ile Ser Gln Phe Ile Ile
    2090                2095                2100

Met Tyr Ser Leu Asp Gly Lys Lys Trp Gln Thr Tyr Arg Gly Asn
    2105                2110                2115

Ser Thr Gly Thr Leu Met Val Phe Phe Gly Asn Val Asp Ser Ser
    2120                2125                2130

Gly Ile Lys His Asn Ile Phe Asn Pro Pro Ile Ile Ala Arg Tyr
    2135                2140                2145

Ile Arg Leu His Pro Thr His Tyr Ser Ile Arg Ser Thr Leu Arg
    2150                2155                2160

Met Glu Leu Met Gly Cys Asp Leu Asn Ser Cys Ser Met Pro Leu
    2165                2170                2175

Gly Met Glu Ser Lys Ala Ile Ser Asp Ala Gln Ile Thr Ala Ser
    2180                2185                2190

Ser Tyr Phe Thr Asn Met Phe Ala Thr Trp Ser Pro Ser Lys Ala
    2195                2200                2205

Arg Leu His Leu Gln Gly Arg Ser Asn Ala Trp Arg Pro Gln Val
    2210                2215                2220

Asn Asn Pro Lys Glu Trp Leu Gln Val Asp Phe Gln Lys Thr Met
    2225                2230                2235

Lys Val Thr Gly Val Thr Thr Gln Gly Val Lys Ser Leu Leu Thr
    2240                2245                2250

Ser Met Tyr Val Lys Glu Phe Leu Ile Ser Ser Ser Gln Asp Gly
    2255                2260                2265

His Gln Trp Thr Leu Phe Phe Gln Asn Gly Lys Val Lys Val Phe
    2270                2275                2280

Gln Gly Asn Gln Asp Ser Phe Thr Pro Val Val Asn Ser Leu Asp
    2285                2290                2295

Pro Pro Leu Leu Thr Arg Tyr Leu Arg Ile His Pro Gln Ser Trp
    2300                2305                2310

Val His Gln Ile Ala Leu Arg Met Glu Val Leu Gly Cys Glu Ala
    2315                2320                2325

Gln Asp Leu Tyr
    2330

<210> SEQ ID NO 2
<211> LENGTH: 21
<212> TYPE: PRT
<213> ORGANISM: artificial
<220> FEATURE:
<223> OTHER INFORMATION: A truncated FVIII B domain

<400> SEQUENCE: 2

Ser Phe Ser Gln Asn Ser Arg His Pro Ser Gln Asn Pro Pro Val Leu
1               5                   10                  15

Lys Arg His Gln Arg
            20
```

<210> SEQ ID NO 3
<211> LENGTH: 1438
<212> TYPE: PRT
<213> ORGANISM: artificial
<220> FEATURE:
<223> OTHER INFORMATION: B domain truncated/deleted human FVIII variant
      comprising a K2092 substitution

<400> SEQUENCE: 3

```
Ala Thr Arg Arg Tyr Tyr Leu Gly Ala Val Glu Leu Ser Trp Asp Tyr
1               5                   10                  15

Met Gln Ser Asp Leu Gly Glu Leu Pro Val Asp Ala Arg Phe Pro Pro
            20                  25                  30

Arg Val Pro Lys Ser Phe Pro Phe Asn Thr Ser Val Val Tyr Lys Lys
        35                  40                  45

Thr Leu Phe Val Glu Phe Thr Asp His Leu Phe Asn Ile Ala Lys Pro
    50                  55                  60

Arg Pro Pro Trp Met Gly Leu Leu Gly Pro Thr Ile Gln Ala Glu Val
65                  70                  75                  80

Tyr Asp Thr Val Val Ile Thr Leu Lys Asn Met Ala Ser His Pro Val
                85                  90                  95

Ser Leu His Ala Val Gly Val Ser Tyr Trp Lys Ala Ser Glu Gly Ala
            100                 105                 110

Glu Tyr Asp Asp Gln Thr Ser Gln Arg Glu Lys Glu Asp Asp Lys Val
        115                 120                 125

Phe Pro Gly Gly Ser His Thr Tyr Val Trp Gln Val Leu Lys Glu Asn
    130                 135                 140

Gly Pro Met Ala Ser Asp Pro Leu Cys Leu Thr Tyr Ser Tyr Leu Ser
145                 150                 155                 160

His Val Asp Leu Val Lys Asp Leu Asn Ser Gly Leu Ile Gly Ala Leu
                165                 170                 175

Leu Val Cys Arg Glu Gly Ser Leu Ala Lys Glu Lys Thr Gln Thr Leu
            180                 185                 190

His Lys Phe Ile Leu Leu Phe Ala Val Phe Asp Glu Gly Lys Ser Trp
        195                 200                 205

His Ser Glu Thr Lys Asn Ser Leu Met Gln Asp Arg Asp Ala Ala Ser
    210                 215                 220

Ala Arg Ala Trp Pro Lys Met His Thr Val Asn Gly Tyr Val Asn Arg
225                 230                 235                 240

Ser Leu Pro Gly Leu Ile Gly Cys His Arg Lys Ser Val Tyr Trp His
                245                 250                 255

Val Ile Gly Met Gly Thr Thr Pro Glu Val His Ser Ile Phe Leu Glu
            260                 265                 270

Gly His Thr Phe Leu Val Arg Asn His Arg Gln Ala Ser Leu Glu Ile
        275                 280                 285

Ser Pro Ile Thr Phe Leu Thr Ala Gln Thr Leu Leu Met Asp Leu Gly
    290                 295                 300

Gln Phe Leu Leu Phe Cys His Ile Ser Ser His Gln His Asp Gly Met
305                 310                 315                 320

Glu Ala Tyr Val Lys Val Asp Ser Cys Pro Glu Glu Pro Gln Leu Arg
                325                 330                 335

Met Lys Asn Asn Glu Glu Ala Glu Asp Tyr Asp Asp Leu Thr Asp
            340                 345                 350

Ser Glu Met Asp Val Val Arg Phe Asp Asp Asp Asn Ser Pro Ser Phe
        355                 360                 365
```

```
Ile Gln Ile Arg Ser Val Ala Lys Lys His Pro Lys Thr Trp Val His
370                 375                 380
Tyr Ile Ala Ala Glu Glu Asp Trp Asp Tyr Ala Pro Leu Val Leu
385                 390                 395                 400
Ala Pro Asp Asp Arg Ser Tyr Lys Ser Gln Tyr Leu Asn Asn Gly Pro
                405                 410                 415
Gln Arg Ile Gly Arg Lys Tyr Lys Val Arg Phe Met Ala Tyr Thr
                420                 425                 430
Asp Glu Thr Phe Lys Thr Arg Glu Ala Ile Gln His Glu Ser Gly Ile
                435                 440                 445
Leu Gly Pro Leu Leu Tyr Gly Glu Val Gly Asp Thr Leu Leu Ile Ile
450                 455                 460
Phe Lys Asn Gln Ala Ser Arg Pro Tyr Asn Ile Tyr Pro His Gly Ile
465                 470                 475                 480
Thr Asp Val Arg Pro Leu Tyr Ser Arg Arg Leu Pro Lys Gly Val Lys
                485                 490                 495
His Leu Lys Asp Phe Pro Ile Leu Pro Gly Glu Ile Phe Lys Tyr Lys
                500                 505                 510
Trp Thr Val Thr Val Glu Asp Gly Pro Thr Lys Ser Asp Pro Arg Cys
                515                 520                 525
Leu Thr Arg Tyr Tyr Ser Ser Phe Val Asn Met Glu Arg Asp Leu Ala
530                 535                 540
Ser Gly Leu Ile Gly Pro Leu Leu Ile Cys Tyr Lys Glu Ser Val Asp
545                 550                 555                 560
Gln Arg Gly Asn Gln Ile Met Ser Asp Lys Arg Asn Val Ile Leu Phe
                565                 570                 575
Ser Val Phe Asp Glu Asn Arg Ser Trp Tyr Leu Thr Glu Asn Ile Gln
                580                 585                 590
Arg Phe Leu Pro Asn Pro Ala Gly Val Gln Leu Glu Asp Pro Glu Phe
                595                 600                 605
Gln Ala Ser Asn Ile Met His Ser Ile Asn Gly Tyr Val Phe Asp Ser
                610                 615                 620
Leu Gln Leu Ser Val Cys Leu His Glu Val Ala Tyr Trp Tyr Ile Leu
625                 630                 635                 640
Ser Ile Gly Ala Gln Thr Asp Phe Leu Ser Val Phe Phe Ser Gly Tyr
                645                 650                 655
Thr Phe Lys His Lys Met Val Tyr Glu Asp Thr Leu Thr Leu Phe Pro
                660                 665                 670
Phe Ser Gly Glu Thr Val Phe Met Ser Met Glu Asn Pro Gly Leu Trp
                675                 680                 685
Ile Leu Gly Cys His Asn Ser Asp Phe Arg Asn Arg Gly Met Thr Ala
                690                 695                 700
Leu Leu Lys Val Ser Ser Cys Asp Lys Asn Thr Gly Asp Tyr Tyr Glu
705                 710                 715                 720
Asp Ser Tyr Glu Asp Ile Ser Ala Tyr Leu Leu Ser Lys Asn Asn Ala
                725                 730                 735
Ile Glu Pro Arg Ser Phe Ser Gln Asn Pro Pro Val Leu Lys Arg His
                740                 745                 750
Gln Arg Glu Ile Thr Arg Thr Thr Leu Gln Ser Asp Gln Glu Glu Ile
                755                 760                 765
Asp Tyr Asp Asp Thr Ile Ser Val Glu Met Lys Lys Glu Asp Phe Asp
770                 775                 780
```

```
Ile Tyr Asp Glu Asp Glu Asn Gln Ser Pro Arg Ser Phe Gln Lys Lys
785                 790                 795                 800

Thr Arg His Tyr Phe Ile Ala Ala Val Glu Arg Leu Trp Asp Tyr Gly
            805                 810                 815

Met Ser Ser Ser Pro His Val Leu Arg Asn Arg Ala Gln Ser Gly Ser
        820                 825                 830

Val Pro Gln Phe Lys Lys Val Phe Gln Glu Phe Thr Asp Gly Ser
    835                 840                 845

Phe Thr Gln Pro Leu Tyr Arg Gly Glu Leu Asn His Leu Gly Leu
850                 855                 860

Leu Gly Pro Tyr Ile Arg Ala Glu Val Glu Asp Asn Ile Met Val Thr
865                 870                 875                 880

Phe Arg Asn Gln Ala Ser Arg Pro Tyr Ser Phe Tyr Ser Ser Leu Ile
            885                 890                 895

Ser Tyr Glu Glu Asp Gln Arg Gln Gly Ala Glu Pro Arg Lys Asn Phe
            900                 905                 910

Val Lys Pro Asn Glu Thr Lys Thr Tyr Phe Trp Lys Val Gln His His
    915                 920                 925

Met Ala Pro Thr Lys Asp Glu Phe Asp Cys Lys Ala Trp Ala Tyr Phe
930                 935                 940

Ser Asp Val Asp Leu Glu Lys Asp Val His Ser Gly Leu Ile Gly Pro
945                 950                 955                 960

Leu Leu Val Cys His Thr Asn Thr Leu Asn Pro Ala His Gly Arg Gln
            965                 970                 975

Val Thr Val Gln Glu Phe Ala Leu Phe Phe Thr Ile Phe Asp Glu Thr
            980                 985                 990

Lys Ser Trp Tyr Phe Thr Glu Asn Met Glu Arg Asn Cys Arg Ala Pro
            995                 1000                1005

Cys Asn Ile Gln Met Glu Asp Pro Thr Phe Lys Glu Asn Tyr Arg
    1010                1015                1020

Phe His Ala Ile Asn Gly Tyr Ile Met Asp Thr Leu Pro Gly Leu
    1025                1030                1035

Val Met Ala Gln Asp Gln Arg Ile Arg Trp Tyr Leu Leu Ser Met
    1040                1045                1050

Gly Ser Asn Glu Asn Ile His Ser Ile His Phe Ser Gly His Val
    1055                1060                1065

Phe Thr Val Arg Lys Lys Glu Glu Tyr Lys Met Ala Leu Tyr Asn
    1070                1075                1080

Leu Tyr Pro Gly Val Phe Glu Thr Val Glu Met Leu Pro Ser Lys
    1085                1090                1095

Ala Gly Ile Trp Arg Val Glu Cys Leu Ile Gly Glu His Leu His
    1100                1105                1110

Ala Gly Met Ser Thr Leu Phe Leu Val Tyr Ser Asn Lys Cys Gln
    1115                1120                1125

Thr Pro Leu Gly Met Ala Ser Gly His Ile Arg Asp Phe Gln Ile
    1130                1135                1140

Thr Ala Ser Gly Gln Tyr Gly Gln Trp Ala Pro Lys Leu Ala Arg
    1145                1150                1155

Leu His Tyr Ser Gly Ser Ile Asn Ala Trp Ser Thr Lys Glu Pro
    1160                1165                1170

Phe Ser Trp Ile Lys Val Asp Leu Leu Ala Pro Met Ile Ile His
    1175                1180                1185
```

Gly Ile Lys Thr Gln Gly Ala Arg Gln Ala Phe Ser Ser Leu Tyr
    1190            1195                1200

Ile Ser Gln Phe Ile Ile Met Tyr Ser Leu Asp Gly Lys Lys Trp
    1205            1210                1215

Gln Thr Tyr Arg Gly Asn Ser Thr Gly Thr Leu Met Val Phe Phe
    1220            1225                1230

Gly Asn Val Asp Ser Ser Gly Ile Lys His Asn Ile Phe Asn Pro
    1235            1240                1245

Pro Ile Ile Ala Arg Tyr Ile Arg Leu His Pro Thr His Tyr Ser
    1250            1255                1260

Ile Arg Ser Thr Leu Arg Met Glu Leu Met Gly Cys Asp Leu Asn
    1265            1270                1275

Ser Cys Ser Met Pro Leu Gly Met Glu Ser Lys Ala Ile Ser Asp
    1280            1285                1290

Ala Gln Ile Thr Ala Ser Ser Tyr Phe Thr Asn Met Phe Ala Thr
    1295            1300                1305

Trp Ser Pro Ser Lys Ala Arg Leu His Leu Gln Gly Arg Ser Asn
    1310            1315                1320

Ala Trp Arg Pro Gln Val Asn Asn Pro Lys Glu Trp Leu Gln Val
    1325            1330                1335

Asp Phe Gln Lys Thr Met Lys Val Thr Gly Val Thr Thr Gln Gly
    1340            1345                1350

Val Lys Ser Leu Leu Thr Ser Met Tyr Val Lys Glu Phe Leu Ile
    1355            1360                1365

Ser Ser Ser Gln Asp Gly His Gln Trp Thr Leu Phe Phe Gln Asn
    1370            1375                1380

Gly Lys Val Lys Val Phe Gln Gly Asn Gln Asp Ser Phe Thr Pro
    1385            1390                1395

Val Val Asn Ser Leu Asp Pro Pro Leu Leu Thr Arg Tyr Leu Arg
    1400            1405                1410

Ile His Pro Gln Ser Trp Val His Gln Ile Ala Leu Arg Met Glu
    1415            1420                1425

Val Leu Gly Cys Glu Ala Gln Asp Leu Tyr
    1430            1435

<210> SEQ ID NO 4
<211> LENGTH: 1438
<212> TYPE: PRT
<213> ORGANISM: artificial
<220> FEATURE:
<223> OTHER INFORMATION: B domain truncated/deleted human FVIII variant
      comprising a F2093 substitution.

<400> SEQUENCE: 4

Ala Thr Arg Arg Tyr Tyr Leu Gly Ala Val Glu Leu Ser Trp Asp Tyr
1               5                   10                  15

Met Gln Ser Asp Leu Gly Glu Leu Pro Val Asp Ala Arg Phe Pro Pro
                20                  25                  30

Arg Val Pro Lys Ser Phe Pro Phe Asn Thr Ser Val Val Tyr Lys Lys
            35                  40                  45

Thr Leu Phe Val Glu Phe Thr Asp His Leu Phe Asn Ile Ala Lys Pro
        50                  55                  60

Arg Pro Pro Trp Met Gly Leu Leu Gly Pro Thr Ile Gln Ala Glu Val
65                  70                  75                  80

Tyr Asp Thr Val Val Ile Thr Leu Lys Asn Met Ala Ser His Pro Val
                85                  90                  95

-continued

```
Ser Leu His Ala Val Gly Val Ser Tyr Trp Lys Ala Ser Glu Gly Ala
            100                 105                 110

Glu Tyr Asp Asp Gln Thr Ser Gln Arg Glu Lys Glu Asp Asp Lys Val
        115                 120                 125

Phe Pro Gly Gly Ser His Thr Tyr Val Trp Gln Val Leu Lys Glu Asn
    130                 135                 140

Gly Pro Met Ala Ser Asp Pro Leu Cys Leu Thr Tyr Ser Tyr Leu Ser
145                 150                 155                 160

His Val Asp Leu Val Lys Asp Leu Asn Ser Gly Leu Ile Gly Ala Leu
                165                 170                 175

Leu Val Cys Arg Glu Gly Ser Leu Ala Lys Glu Lys Thr Gln Thr Leu
            180                 185                 190

His Lys Phe Ile Leu Leu Phe Ala Val Phe Asp Glu Gly Lys Ser Trp
        195                 200                 205

His Ser Glu Thr Lys Asn Ser Leu Met Gln Asp Arg Asp Ala Ala Ser
    210                 215                 220

Ala Arg Ala Trp Pro Lys Met His Thr Val Asn Gly Tyr Val Asn Arg
225                 230                 235                 240

Ser Leu Pro Gly Leu Ile Gly Cys His Arg Lys Ser Val Tyr Trp His
                245                 250                 255

Val Ile Gly Met Gly Thr Thr Pro Glu Val His Ser Ile Phe Leu Glu
            260                 265                 270

Gly His Thr Phe Leu Val Arg Asn His Arg Gln Ala Ser Leu Glu Ile
        275                 280                 285

Ser Pro Ile Thr Phe Leu Thr Ala Gln Thr Leu Leu Met Asp Leu Gly
    290                 295                 300

Gln Phe Leu Leu Phe Cys His Ile Ser Ser His Gln His Asp Gly Met
305                 310                 315                 320

Glu Ala Tyr Val Lys Val Asp Ser Cys Pro Glu Glu Pro Gln Leu Arg
                325                 330                 335

Met Lys Asn Asn Glu Glu Ala Glu Asp Tyr Asp Asp Asp Leu Thr Asp
            340                 345                 350

Ser Glu Met Asp Val Val Arg Phe Asp Asp Asn Ser Pro Ser Phe
        355                 360                 365

Ile Gln Ile Arg Ser Val Ala Lys Lys His Pro Lys Thr Trp Val His
    370                 375                 380

Tyr Ile Ala Ala Glu Glu Glu Asp Trp Asp Tyr Ala Pro Leu Val Leu
385                 390                 395                 400

Ala Pro Asp Asp Arg Ser Tyr Lys Ser Gln Tyr Leu Asn Asn Gly Pro
                405                 410                 415

Gln Arg Ile Gly Arg Lys Tyr Lys Lys Val Arg Phe Met Ala Tyr Thr
            420                 425                 430

Asp Glu Thr Phe Lys Thr Arg Glu Ala Ile Gln His Glu Ser Gly Ile
        435                 440                 445

Leu Gly Pro Leu Leu Tyr Gly Glu Val Gly Asp Thr Leu Leu Ile Ile
    450                 455                 460

Phe Lys Asn Gln Ala Ser Arg Pro Tyr Asn Ile Tyr Pro His Gly Ile
465                 470                 475                 480

Thr Asp Val Arg Pro Leu Tyr Ser Arg Arg Leu Pro Lys Gly Val Lys
                485                 490                 495

His Leu Lys Asp Phe Pro Ile Leu Pro Gly Glu Ile Phe Lys Tyr Lys
            500                 505                 510
```

```
Trp Thr Val Thr Val Glu Asp Gly Pro Thr Lys Ser Asp Pro Arg Cys
            515                 520                 525

Leu Thr Arg Tyr Ser Ser Phe Val Asn Met Glu Arg Asp Leu Ala
530                 535                 540

Ser Gly Leu Ile Gly Pro Leu Ile Cys Tyr Lys Glu Ser Val Asp
545                 550                 555                 560

Gln Arg Gly Asn Gln Ile Met Ser Asp Lys Arg Asn Val Ile Leu Phe
                565                 570                 575

Ser Val Phe Asp Glu Asn Arg Ser Trp Tyr Leu Thr Glu Asn Ile Gln
            580                 585                 590

Arg Phe Leu Pro Asn Pro Ala Gly Val Gln Leu Glu Asp Pro Glu Phe
        595                 600                 605

Gln Ala Ser Asn Ile Met His Ser Ile Asn Gly Tyr Val Phe Asp Ser
    610                 615                 620

Leu Gln Leu Ser Val Cys Leu His Glu Val Ala Tyr Trp Tyr Ile Leu
625                 630                 635                 640

Ser Ile Gly Ala Gln Thr Asp Phe Leu Ser Val Phe Phe Ser Gly Tyr
                645                 650                 655

Thr Phe Lys His Lys Met Val Tyr Glu Asp Thr Leu Thr Leu Phe Pro
            660                 665                 670

Phe Ser Gly Glu Thr Val Phe Met Ser Met Glu Asn Pro Gly Leu Trp
        675                 680                 685

Ile Leu Gly Cys His Asn Ser Asp Phe Arg Asn Arg Gly Met Thr Ala
    690                 695                 700

Leu Leu Lys Val Ser Ser Cys Asp Lys Asn Thr Gly Asp Tyr Tyr Glu
705                 710                 715                 720

Asp Ser Tyr Glu Asp Ile Ser Ala Tyr Leu Leu Ser Lys Asn Asn Ala
                725                 730                 735

Ile Glu Pro Arg Ser Phe Ser Gln Asn Pro Pro Val Leu Lys Arg His
            740                 745                 750

Gln Arg Glu Ile Thr Arg Thr Thr Leu Gln Ser Asp Gln Glu Glu Ile
        755                 760                 765

Asp Tyr Asp Asp Thr Ile Ser Val Glu Met Lys Lys Glu Asp Phe Asp
    770                 775                 780

Ile Tyr Asp Glu Asp Glu Asn Gln Ser Pro Arg Ser Phe Gln Lys Lys
785                 790                 795                 800

Thr Arg His Tyr Phe Ile Ala Ala Val Glu Arg Leu Trp Asp Tyr Gly
                805                 810                 815

Met Ser Ser Ser Pro His Val Leu Arg Asn Arg Ala Gln Ser Gly Ser
            820                 825                 830

Val Pro Gln Phe Lys Lys Val Val Phe Gln Glu Phe Thr Asp Gly Ser
        835                 840                 845

Phe Thr Gln Pro Leu Tyr Arg Gly Glu Leu Asn Glu His Leu Gly Leu
    850                 855                 860

Leu Gly Pro Tyr Ile Arg Ala Glu Val Glu Asp Asn Ile Met Val Thr
865                 870                 875                 880

Phe Arg Asn Gln Ala Ser Arg Pro Tyr Ser Phe Tyr Ser Ser Leu Ile
                885                 890                 895

Ser Tyr Glu Glu Asp Gln Arg Gln Gly Ala Glu Pro Arg Lys Asn Phe
            900                 905                 910

Val Lys Pro Asn Glu Thr Lys Thr Tyr Phe Trp Lys Val Gln His His
        915                 920                 925
```

-continued

```
Met Ala Pro Thr Lys Asp Glu Phe Asp Cys Lys Ala Trp Ala Tyr Phe
    930                 935                 940

Ser Asp Val Asp Leu Glu Lys Asp Val His Ser Gly Leu Ile Gly Pro
945                 950                 955                 960

Leu Leu Val Cys His Thr Asn Thr Leu Asn Pro Ala His Gly Arg Gln
            965                 970                 975

Val Thr Val Gln Glu Phe Ala Leu Phe Phe Thr Ile Phe Asp Glu Thr
                980                 985                 990

Lys Ser Trp Tyr Phe Thr Glu Asn Met Glu Arg Asn Cys Arg Ala Pro
        995                 1000                1005

Cys Asn Ile Gln Met Glu Asp Pro Thr Phe Lys Glu Asn Tyr Arg
    1010                1015                1020

Phe His Ala Ile Asn Gly Tyr Ile Met Asp Thr Leu Pro Gly Leu
    1025                1030                1035

Val Met Ala Gln Asp Gln Arg Ile Arg Trp Tyr Leu Leu Ser Met
    1040                1045                1050

Gly Ser Asn Glu Asn Ile His Ser Ile His Phe Ser Gly His Val
    1055                1060                1065

Phe Thr Val Arg Lys Lys Glu Glu Tyr Lys Met Ala Leu Tyr Asn
    1070                1075                1080

Leu Tyr Pro Gly Val Phe Glu Thr Val Glu Met Leu Pro Ser Lys
    1085                1090                1095

Ala Gly Ile Trp Arg Val Glu Cys Leu Ile Gly Glu His Leu His
    1100                1105                1110

Ala Gly Met Ser Thr Leu Phe Leu Val Tyr Ser Asn Lys Cys Gln
    1115                1120                1125

Thr Pro Leu Gly Met Ala Ser Gly His Ile Arg Asp Phe Gln Ile
    1130                1135                1140

Thr Ala Ser Gly Gln Tyr Gly Gln Trp Ala Pro Lys Leu Ala Arg
    1145                1150                1155

Leu His Tyr Ser Gly Ser Ile Asn Ala Trp Ser Thr Lys Glu Pro
    1160                1165                1170

Phe Ser Trp Ile Lys Val Asp Leu Leu Ala Pro Met Ile Ile His
    1175                1180                1185

Gly Ile Lys Thr Gln Gly Ala Arg Gln Lys Ala Ser Ser Leu Tyr
    1190                1195                1200

Ile Ser Gln Phe Ile Ile Met Tyr Ser Leu Asp Gly Lys Lys Trp
    1205                1210                1215

Gln Thr Tyr Arg Gly Asn Ser Thr Gly Thr Leu Met Val Phe Phe
    1220                1225                1230

Gly Asn Val Asp Ser Ser Gly Ile Lys His Asn Ile Phe Asn Pro
    1235                1240                1245

Pro Ile Ile Ala Arg Tyr Ile Arg Leu His Pro Thr His Tyr Ser
    1250                1255                1260

Ile Arg Ser Thr Leu Arg Met Glu Leu Met Gly Cys Asp Leu Asn
    1265                1270                1275

Ser Cys Ser Met Pro Leu Gly Met Glu Ser Lys Ala Ile Ser Asp
    1280                1285                1290

Ala Gln Ile Thr Ala Ser Ser Tyr Phe Thr Asn Met Phe Ala Thr
    1295                1300                1305

Trp Ser Pro Ser Lys Ala Arg Leu His Leu Gln Gly Arg Ser Asn
    1310                1315                1320
```

```
Ala Trp Arg Pro Gln Val Asn Asn Pro Lys Glu Trp Leu Gln Val
1325                1330                1335

Asp Phe Gln Lys Thr Met Lys Val Thr Gly Val Thr Thr Gln Gly
1340                1345                1350

Val Lys Ser Leu Leu Thr Ser Met Tyr Val Lys Glu Phe Leu Ile
1355                1360                1365

Ser Ser Ser Gln Asp Gly His Gln Trp Thr Leu Phe Phe Gln Asn
1370                1375                1380

Gly Lys Val Lys Val Phe Gln Gly Asn Gln Asp Ser Phe Thr Pro
1385                1390                1395

Val Val Asn Ser Leu Asp Pro Pro Leu Leu Thr Arg Tyr Leu Arg
1400                1405                1410

Ile His Pro Gln Ser Trp Val His Gln Ile Ala Leu Arg Met Glu
1415                1420                1425

Val Leu Gly Cys Glu Ala Gln Asp Leu Tyr
1430                1435

<210> SEQ ID NO 5
<211> LENGTH: 1438
<212> TYPE: PRT
<213> ORGANISM: artificial
<220> FEATURE:
<223> OTHER INFORMATION: B domain deleted/truncated FVIII variant
      comprising the K2092A and the F2093A substitutions.

<400> SEQUENCE: 5

Ala Thr Arg Arg Tyr Tyr Leu Gly Ala Val Glu Leu Ser Trp Asp Tyr
1               5                   10                  15

Met Gln Ser Asp Leu Gly Glu Leu Pro Val Asp Ala Arg Phe Pro Pro
                20                  25                  30

Arg Val Pro Lys Ser Phe Pro Phe Asn Thr Ser Val Val Tyr Lys Lys
            35                  40                  45

Thr Leu Phe Val Glu Phe Thr Asp His Leu Phe Asn Ile Ala Lys Pro
    50                  55                  60

Arg Pro Pro Trp Met Gly Leu Leu Gly Pro Thr Ile Gln Ala Glu Val
65              70                  75                  80

Tyr Asp Thr Val Val Ile Thr Leu Lys Asn Met Ala Ser His Pro Val
                85                  90                  95

Ser Leu His Ala Val Gly Val Ser Tyr Trp Lys Ala Ser Glu Gly Ala
            100                 105                 110

Glu Tyr Asp Asp Gln Thr Ser Gln Arg Glu Lys Glu Asp Asp Lys Val
        115                 120                 125

Phe Pro Gly Gly Ser His Thr Tyr Val Trp Gln Val Leu Lys Glu Asn
    130                 135                 140

Gly Pro Met Ala Ser Asp Pro Leu Cys Leu Thr Tyr Ser Tyr Leu Ser
145                 150                 155                 160

His Val Asp Leu Val Lys Asp Leu Asn Ser Gly Leu Ile Gly Ala Leu
                165                 170                 175

Leu Val Cys Arg Glu Gly Ser Leu Ala Lys Glu Lys Thr Gln Thr Leu
            180                 185                 190

His Lys Phe Ile Leu Leu Phe Ala Val Phe Asp Glu Gly Lys Ser Trp
        195                 200                 205

His Ser Glu Thr Lys Asn Ser Leu Met Gln Asp Arg Asp Ala Ala Ser
    210                 215                 220

Ala Arg Ala Trp Pro Lys Met His Thr Val Asn Gly Tyr Val Asn Arg
225                 230                 235                 240
```

-continued

```
Ser Leu Pro Gly Leu Ile Gly Cys His Arg Lys Ser Val Tyr Trp His
                245                 250                 255
Val Ile Gly Met Gly Thr Thr Pro Glu Val His Ser Ile Phe Leu Glu
            260                 265                 270
Gly His Thr Phe Leu Val Arg Asn His Arg Gln Ala Ser Leu Glu Ile
        275                 280                 285
Ser Pro Ile Thr Phe Leu Thr Ala Gln Thr Leu Leu Met Asp Leu Gly
    290                 295                 300
Gln Phe Leu Leu Phe Cys His Ile Ser Ser His Gln His Asp Gly Met
305                 310                 315                 320
Glu Ala Tyr Val Lys Val Asp Ser Cys Pro Glu Glu Pro Gln Leu Arg
                325                 330                 335
Met Lys Asn Asn Glu Glu Ala Glu Asp Tyr Asp Asp Asp Leu Thr Asp
            340                 345                 350
Ser Glu Met Asp Val Val Arg Phe Asp Asp Asp Asn Ser Pro Ser Phe
        355                 360                 365
Ile Gln Ile Arg Ser Val Ala Lys Lys His Pro Lys Thr Trp Val His
    370                 375                 380
Tyr Ile Ala Ala Glu Glu Glu Asp Trp Asp Tyr Ala Pro Leu Val Leu
385                 390                 395                 400
Ala Pro Asp Asp Arg Ser Tyr Lys Ser Gln Tyr Leu Asn Asn Gly Pro
                405                 410                 415
Gln Arg Ile Gly Arg Lys Tyr Lys Lys Val Arg Phe Met Ala Tyr Thr
            420                 425                 430
Asp Glu Thr Phe Lys Thr Arg Glu Ala Ile Gln His Glu Ser Gly Ile
        435                 440                 445
Leu Gly Pro Leu Leu Tyr Gly Glu Val Gly Asp Thr Leu Leu Ile Ile
    450                 455                 460
Phe Lys Asn Gln Ala Ser Arg Pro Tyr Asn Ile Tyr Pro His Gly Ile
465                 470                 475                 480
Thr Asp Val Arg Pro Leu Tyr Ser Arg Arg Leu Pro Lys Gly Val Lys
                485                 490                 495
His Leu Lys Asp Phe Pro Ile Leu Pro Gly Glu Ile Phe Lys Tyr Lys
            500                 505                 510
Trp Thr Val Thr Val Glu Asp Gly Pro Thr Lys Ser Asp Pro Arg Cys
        515                 520                 525
Leu Thr Arg Tyr Tyr Ser Ser Phe Val Asn Met Glu Arg Asp Leu Ala
    530                 535                 540
Ser Gly Leu Ile Gly Pro Leu Leu Ile Cys Tyr Lys Glu Ser Val Asp
545                 550                 555                 560
Gln Arg Gly Asn Gln Ile Met Ser Asp Lys Arg Asn Val Ile Leu Phe
                565                 570                 575
Ser Val Phe Asp Glu Asn Arg Ser Trp Tyr Leu Thr Glu Asn Ile Gln
            580                 585                 590
Arg Phe Leu Pro Asn Pro Ala Gly Val Gln Leu Glu Asp Pro Glu Phe
        595                 600                 605
Gln Ala Ser Asn Ile Met His Ser Ile Asn Gly Tyr Val Phe Asp Ser
    610                 615                 620
Leu Gln Leu Ser Val Cys Leu His Glu Val Ala Tyr Trp Tyr Ile Leu
625                 630                 635                 640
Ser Ile Gly Ala Gln Thr Asp Phe Leu Ser Val Phe Phe Ser Gly Tyr
                645                 650                 655
```

-continued

```
Thr Phe Lys His Lys Met Val Tyr Glu Asp Thr Leu Thr Leu Phe Pro
            660                 665                 670
Phe Ser Gly Glu Thr Val Phe Met Ser Met Glu Asn Pro Gly Leu Trp
        675                 680                 685
Ile Leu Gly Cys His Asn Ser Asp Phe Arg Asn Arg Gly Met Thr Ala
    690                 695                 700
Leu Leu Lys Val Ser Ser Cys Asp Lys Asn Thr Gly Asp Tyr Tyr Glu
705                 710                 715                 720
Asp Ser Tyr Glu Asp Ile Ser Ala Tyr Leu Ser Lys Asn Asn Ala
            725                 730                 735
Ile Glu Pro Arg Ser Phe Ser Gln Asn Pro Val Leu Lys Arg His
        740                 745                 750
Gln Arg Glu Ile Thr Arg Thr Thr Leu Gln Ser Asp Gln Glu Glu Ile
            755                 760                 765
Asp Tyr Asp Asp Thr Ile Ser Val Glu Met Lys Lys Glu Asp Phe Asp
        770                 775                 780
Ile Tyr Asp Glu Asp Glu Asn Gln Ser Pro Arg Ser Phe Gln Lys Lys
785                 790                 795                 800
Thr Arg His Tyr Phe Ile Ala Ala Val Glu Arg Leu Trp Asp Tyr Gly
            805                 810                 815
Met Ser Ser Ser Pro His Val Leu Arg Asn Arg Ala Gln Ser Gly Ser
        820                 825                 830
Val Pro Gln Phe Lys Lys Val Val Phe Gln Glu Phe Thr Asp Gly Ser
            835                 840                 845
Phe Thr Gln Pro Leu Tyr Arg Gly Glu Leu Asn Glu His Leu Gly Leu
    850                 855                 860
Leu Gly Pro Tyr Ile Arg Ala Glu Val Glu Asp Asn Ile Met Val Thr
865                 870                 875                 880
Phe Arg Asn Gln Ala Ser Arg Pro Tyr Ser Phe Tyr Ser Ser Leu Ile
            885                 890                 895
Ser Tyr Glu Glu Asp Gln Arg Gln Gly Ala Glu Pro Arg Lys Asn Phe
        900                 905                 910
Val Lys Pro Asn Glu Thr Lys Thr Tyr Phe Trp Lys Val Gln His His
    915                 920                 925
Met Ala Pro Thr Lys Asp Glu Phe Asp Cys Lys Ala Trp Ala Tyr Phe
    930                 935                 940
Ser Asp Val Asp Leu Glu Lys Asp Val His Ser Gly Leu Ile Gly Pro
945                 950                 955                 960
Leu Leu Val Cys His Thr Asn Thr Leu Asn Pro Ala His Gly Arg Gln
            965                 970                 975
Val Thr Val Gln Glu Phe Ala Leu Phe Phe Thr Ile Phe Asp Glu Thr
        980                 985                 990
Lys Ser Trp Tyr Phe Thr Glu Asn Met Glu Arg Asn Cys Arg Ala Pro
    995                 1000                1005
Cys Asn Ile Gln Met Glu Asp Pro Thr Phe Lys Glu Asn Tyr Arg
    1010                1015                1020
Phe His Ala Ile Asn Gly Tyr Ile Met Asp Thr Leu Pro Gly Leu
    1025                1030                1035
Val Met Ala Gln Asp Gln Arg Ile Arg Trp Tyr Leu Leu Ser Met
    1040                1045                1050
Gly Ser Asn Glu Asn Ile His Ser Ile His Phe Ser Gly His Val
    1055                1060                1065
```

```
Phe Thr Val Arg Lys Lys Glu Glu Tyr Lys Met Ala Leu Tyr Asn
1070                1075                1080

Leu Tyr Pro Gly Val Phe Glu Thr Val Glu Met Leu Pro Ser Lys
1085                1090                1095

Ala Gly Ile Trp Arg Val Glu Cys Leu Ile Gly Glu His Leu His
1100                1105                1110

Ala Gly Met Ser Thr Leu Phe Leu Val Tyr Ser Asn Lys Cys Gln
1115                1120                1125

Thr Pro Leu Gly Met Ala Ser Gly His Ile Arg Asp Phe Gln Ile
1130                1135                1140

Thr Ala Ser Gly Gln Tyr Gly Gln Trp Ala Pro Lys Leu Ala Arg
1145                1150                1155

Leu His Tyr Ser Gly Ser Ile Asn Ala Trp Ser Thr Lys Glu Pro
1160                1165                1170

Phe Ser Trp Ile Lys Val Asp Leu Leu Ala Pro Met Ile Ile His
1175                1180                1185

Gly Ile Lys Thr Gln Gly Ala Arg Gln Ala Ala Ser Ser Leu Tyr
1190                1195                1200

Ile Ser Gln Phe Ile Ile Met Tyr Ser Leu Asp Gly Lys Lys Trp
1205                1210                1215

Gln Thr Tyr Arg Gly Asn Ser Thr Gly Thr Leu Met Val Phe Phe
1220                1225                1230

Gly Asn Val Asp Ser Ser Gly Ile Lys His Asn Ile Phe Asn Pro
1235                1240                1245

Pro Ile Ile Ala Arg Tyr Ile Arg Leu His Pro Thr His Tyr Ser
1250                1255                1260

Ile Arg Ser Thr Leu Arg Met Glu Leu Met Gly Cys Asp Leu Asn
1265                1270                1275

Ser Cys Ser Met Pro Leu Gly Met Glu Ser Lys Ala Ile Ser Asp
1280                1285                1290

Ala Gln Ile Thr Ala Ser Ser Tyr Phe Thr Asn Met Phe Ala Thr
1295                1300                1305

Trp Ser Pro Ser Lys Ala Arg Leu His Leu Gln Gly Arg Ser Asn
1310                1315                1320

Ala Trp Arg Pro Gln Val Asn Asn Pro Lys Glu Trp Leu Gln Val
1325                1330                1335

Asp Phe Gln Lys Thr Met Lys Val Thr Gly Val Thr Thr Gln Gly
1340                1345                1350

Val Lys Ser Leu Leu Thr Ser Met Tyr Val Lys Glu Phe Leu Ile
1355                1360                1365

Ser Ser Ser Gln Asp Gly His Gln Trp Thr Leu Phe Phe Gln Asn
1370                1375                1380

Gly Lys Val Lys Val Phe Gln Gly Asn Gln Asp Ser Phe Thr Pro
1385                1390                1395

Val Val Asn Ser Leu Asp Pro Pro Leu Leu Thr Arg Tyr Leu Arg
1400                1405                1410

Ile His Pro Gln Ser Trp Val His Gln Ile Ala Leu Arg Met Glu
1415                1420                1425

Val Leu Gly Cys Glu Ala Gln Asp Leu Tyr
1430                1435
```

<210> SEQ ID NO 6
<211> LENGTH: 1456
<212> TYPE: PRT
<213> ORGANISM: artificial
<220> FEATURE:
<223> OTHER INFORMATION: B domain deleted/truncated human FVIII variant comprising the R2215A substitution.

<400> SEQUENCE: 6

```
Ala Thr Arg Arg Tyr Tyr Leu Gly Ala Val Glu Leu Ser Trp Asp Tyr
1               5                   10                  15

Met Gln Ser Asp Leu Gly Glu Leu Pro Val Asp Ala Arg Phe Pro Pro
            20                  25                  30

Arg Val Pro Lys Ser Phe Pro Phe Asn Thr Ser Val Val Tyr Lys Lys
        35                  40                  45

Thr Leu Phe Val Glu Phe Thr Asp His Leu Phe Asn Ile Ala Lys Pro
    50                  55                  60

Arg Pro Pro Trp Met Gly Leu Leu Gly Pro Thr Ile Gln Ala Glu Val
65                  70                  75                  80

Tyr Asp Thr Val Val Ile Thr Leu Lys Asn Met Ala Ser His Pro Val
                85                  90                  95

Ser Leu His Ala Val Gly Val Ser Tyr Trp Lys Ala Ser Glu Gly Ala
            100                 105                 110

Glu Tyr Asp Asp Gln Thr Ser Gln Arg Glu Lys Glu Asp Asp Lys Val
        115                 120                 125

Phe Pro Gly Gly Ser His Thr Tyr Val Trp Gln Val Leu Lys Glu Asn
    130                 135                 140

Gly Pro Met Ala Ser Asp Pro Leu Cys Leu Thr Tyr Ser Tyr Leu Ser
145                 150                 155                 160

His Val Asp Leu Val Lys Asp Leu Asn Ser Gly Leu Ile Gly Ala Leu
                165                 170                 175

Leu Val Cys Arg Glu Gly Ser Leu Ala Lys Glu Lys Thr Gln Thr Leu
            180                 185                 190

His Lys Phe Ile Leu Leu Phe Ala Val Phe Asp Glu Gly Lys Ser Trp
        195                 200                 205

His Ser Glu Thr Lys Asn Ser Leu Met Gln Asp Arg Asp Ala Ala Ser
    210                 215                 220

Ala Arg Ala Trp Pro Lys Met His Thr Val Asn Gly Tyr Val Asn Arg
225                 230                 235                 240

Ser Leu Pro Gly Leu Ile Gly Cys His Arg Lys Ser Val Tyr Trp His
                245                 250                 255

Val Ile Gly Met Gly Thr Thr Pro Glu Val His Ser Ile Phe Leu Glu
            260                 265                 270

Gly His Thr Phe Leu Val Arg Asn His Arg Gln Ala Ser Leu Glu Ile
        275                 280                 285

Ser Pro Ile Thr Phe Leu Thr Ala Gln Thr Leu Leu Met Asp Leu Gly
    290                 295                 300

Gln Phe Leu Leu Phe Cys His Ile Ser Ser His Gln His Asp Gly Met
305                 310                 315                 320

Glu Ala Tyr Val Lys Val Asp Ser Cys Pro Glu Glu Pro Gln Leu Arg
                325                 330                 335

Met Lys Asn Asn Glu Glu Ala Glu Asp Tyr Asp Asp Leu Thr Asp
            340                 345                 350

Ser Glu Met Asp Val Val Arg Phe Asp Asp Asp Asn Ser Pro Ser Phe
        355                 360                 365
```

```
Ile Gln Ile Arg Ser Val Ala Lys Lys His Pro Lys Thr Trp Val His
370                 375                 380
Tyr Ile Ala Ala Glu Glu Asp Trp Asp Tyr Ala Pro Leu Val Leu
385                 390                 395                 400
Ala Pro Asp Asp Arg Ser Tyr Lys Ser Gln Tyr Leu Asn Asn Gly Pro
            405                 410                 415
Gln Arg Ile Gly Arg Lys Tyr Lys Val Arg Phe Met Ala Tyr Thr
            420                 425                 430
Asp Glu Thr Phe Lys Thr Arg Glu Ala Ile Gln His Glu Ser Gly Ile
            435                 440                 445
Leu Gly Pro Leu Leu Tyr Gly Glu Val Gly Asp Thr Leu Leu Ile Ile
450                 455                 460
Phe Lys Asn Gln Ala Ser Arg Pro Tyr Asn Ile Tyr Pro His Gly Ile
465                 470                 475                 480
Thr Asp Val Arg Pro Leu Tyr Ser Arg Arg Leu Pro Lys Gly Val Lys
            485                 490                 495
His Leu Lys Asp Phe Pro Ile Leu Pro Gly Glu Ile Phe Lys Tyr Lys
            500                 505                 510
Trp Thr Val Thr Val Glu Asp Gly Pro Thr Lys Ser Asp Pro Arg Cys
            515                 520                 525
Leu Thr Arg Tyr Tyr Ser Ser Phe Val Asn Met Glu Arg Asp Leu Ala
530                 535                 540
Ser Gly Leu Ile Gly Pro Leu Leu Ile Cys Tyr Lys Glu Ser Val Asp
545                 550                 555                 560
Gln Arg Gly Asn Gln Ile Met Ser Asp Lys Arg Asn Val Ile Leu Phe
            565                 570                 575
Ser Val Phe Asp Glu Asn Arg Ser Trp Tyr Leu Thr Glu Asn Ile Gln
            580                 585                 590
Arg Phe Leu Pro Asn Pro Ala Gly Val Gln Leu Glu Asp Pro Glu Phe
            595                 600                 605
Gln Ala Ser Asn Ile Met His Ser Ile Asn Gly Tyr Val Phe Asp Ser
610                 615                 620
Leu Gln Leu Ser Val Cys Leu His Glu Val Ala Tyr Trp Tyr Ile Leu
625                 630                 635                 640
Ser Ile Gly Ala Gln Thr Asp Phe Leu Ser Val Phe Phe Ser Gly Tyr
            645                 650                 655
Thr Phe Lys His Lys Met Val Tyr Glu Asp Thr Leu Thr Leu Phe Pro
            660                 665                 670
Phe Ser Gly Glu Thr Val Phe Met Ser Met Glu Asn Pro Gly Leu Trp
            675                 680                 685
Ile Leu Gly Cys His Asn Ser Asp Phe Arg Asn Arg Gly Met Thr Ala
            690                 695                 700
Leu Leu Lys Val Ser Ser Cys Asp Lys Asn Thr Gly Asp Tyr Tyr Glu
705                 710                 715                 720
Asp Ser Tyr Glu Asp Ile Ser Ala Tyr Leu Leu Ser Lys Asn Asn Ala
            725                 730                 735
Ile Glu Pro Arg Ser Phe Ser Gln Asn Ser Arg His Pro Ser Glu Gln
            740                 745                 750
Lys Leu Ile Ser Glu Glu Asp Leu Ser Gln Asn Pro Pro Val Leu Lys
            755                 760                 765
Arg His Gln Arg Glu Ile Thr Arg Thr Thr Leu Gln Ser Asp Gln Glu
770                 775                 780
```

-continued

```
Glu Ile Asp Tyr Asp Asp Thr Ile Ser Val Glu Met Lys Lys Glu Asp
785                 790                 795                 800

Phe Asp Ile Tyr Asp Glu Asp Glu Asn Gln Ser Pro Arg Ser Phe Gln
            805                 810                 815

Lys Lys Thr Arg His Tyr Phe Ile Ala Ala Val Glu Arg Leu Trp Asp
        820                 825                 830

Tyr Gly Met Ser Ser Pro His Val Leu Arg Asn Arg Ala Gln Ser
    835                 840                 845

Gly Ser Val Pro Gln Phe Lys Lys Val Val Phe Gln Glu Phe Thr Asp
850                 855                 860

Gly Ser Phe Thr Gln Pro Leu Tyr Arg Gly Glu Leu Asn Glu His Leu
865                 870                 875                 880

Gly Leu Leu Gly Pro Tyr Ile Arg Ala Glu Val Glu Asp Asn Ile Met
                885                 890                 895

Val Thr Phe Arg Asn Gln Ala Ser Arg Pro Tyr Ser Phe Tyr Ser Ser
                900                 905                 910

Leu Ile Ser Tyr Glu Glu Asp Gln Arg Gln Gly Ala Glu Pro Arg Lys
            915                 920                 925

Asn Phe Val Lys Pro Asn Glu Thr Lys Thr Tyr Phe Trp Lys Val Gln
930                 935                 940

His His Met Ala Pro Thr Lys Asp Glu Phe Asp Cys Lys Ala Trp Ala
945                 950                 955                 960

Tyr Phe Ser Asp Val Asp Leu Glu Lys Asp Val His Ser Gly Leu Ile
                965                 970                 975

Gly Pro Leu Leu Val Cys His Thr Asn Thr Leu Asn Pro Ala His Gly
            980                 985                 990

Arg Gln Val Thr Val Gln Glu Phe Ala Leu Phe Phe Thr Ile Phe Asp
        995                 1000                1005

Glu Thr Lys Ser Trp Tyr Phe Thr Glu Asn Met Glu Arg Asn Cys
    1010                1015                1020

Arg Ala Pro Cys Asn Ile Gln Met Glu Asp Pro Thr Phe Lys Glu
    1025                1030                1035

Asn Tyr Arg Phe His Ala Ile Asn Gly Tyr Ile Met Asp Thr Leu
    1040                1045                1050

Pro Gly Leu Val Met Ala Gln Asp Gln Arg Ile Arg Trp Tyr Leu
    1055                1060                1065

Leu Ser Met Gly Ser Asn Glu Asn Ile His Ser Ile His Phe Ser
    1070                1075                1080

Gly His Val Phe Thr Val Arg Lys Lys Glu Glu Tyr Lys Met Ala
    1085                1090                1095

Leu Tyr Asn Leu Tyr Pro Gly Val Phe Glu Thr Val Glu Met Leu
    1100                1105                1110

Pro Ser Lys Ala Gly Ile Trp Arg Val Glu Cys Leu Ile Gly Glu
    1115                1120                1125

His Leu His Ala Gly Met Ser Thr Leu Phe Leu Val Tyr Ser Asn
    1130                1135                1140

Lys Cys Gln Thr Pro Leu Gly Met Ala Ser Gly His Ile Arg Asp
    1145                1150                1155

Phe Gln Ile Thr Ala Ser Gly Gln Tyr Gly Gln Trp Ala Pro Lys
    1160                1165                1170

Leu Ala Arg Leu His Tyr Ser Gly Ser Ile Asn Ala Trp Ser Thr
    1175                1180                1185
```

```
Lys Glu Pro Phe Ser Trp Ile Lys Val Asp Leu Leu Ala Pro Met
    1190            1195                1200

Ile Ile His Gly Ile Lys Thr Gln Gly Ala Arg Gln Lys Phe Ser
    1205            1210                1215

Ser Leu Tyr Ile Ser Gln Phe Ile Ile Met Tyr Ser Leu Asp Gly
    1220            1225                1230

Lys Lys Trp Gln Thr Tyr Arg Gly Asn Ser Thr Gly Thr Leu Met
    1235            1240                1245

Val Phe Phe Gly Asn Val Asp Ser Ser Gly Ile Lys His Asn Ile
    1250            1255                1260

Phe Asn Pro Pro Ile Ile Ala Arg Tyr Ile Arg Leu His Pro Thr
    1265            1270                1275

His Tyr Ser Ile Arg Ser Thr Leu Arg Met Glu Leu Met Gly Cys
    1280            1285                1290

Asp Leu Asn Ser Cys Ser Met Pro Leu Gly Met Glu Ser Lys Ala
    1295            1300                1305

Ile Ser Asp Ala Gln Ile Thr Ala Ser Ser Tyr Phe Thr Asn Met
    1310            1315                1320

Phe Ala Thr Trp Ser Pro Ser Lys Ala Arg Leu His Leu Gln Gly
    1325            1330                1335

Ala Ser Asn Ala Trp Arg Pro Gln Val Asn Asn Pro Lys Glu Trp
    1340            1345                1350

Leu Gln Val Asp Phe Gln Lys Thr Met Lys Val Thr Gly Val Thr
    1355            1360                1365

Thr Gln Gly Val Lys Ser Leu Leu Thr Ser Met Tyr Val Lys Glu
    1370            1375                1380

Phe Leu Ile Ser Ser Ser Gln Asp Gly His Gln Trp Thr Leu Phe
    1385            1390                1395

Phe Gln Asn Gly Lys Val Lys Val Phe Gln Gly Asn Gln Asp Ser
    1400            1405                1410

Phe Thr Pro Val Val Asn Ser Leu Asp Pro Pro Leu Leu Thr Arg
    1415            1420                1425

Tyr Leu Arg Ile His Pro Gln Ser Trp Val His Gln Ile Ala Leu
    1430            1435                1440

Arg Met Glu Val Leu Gly Cys Glu Ala Gln Asp Leu Tyr
    1445            1450                1455

<210> SEQ ID NO 7
<211> LENGTH: 1456
<212> TYPE: PRT
<213> ORGANISM: artificial
<220> FEATURE:
<223> OTHER INFORMATION: B domain deleted/truncated human FVIII variant
      comprising the K2065A and the R2215A substitutions

<400> SEQUENCE: 7

Ala Thr Arg Arg Tyr Tyr Leu Gly Ala Val Glu Leu Ser Trp Asp Tyr
1               5                   10                  15

Met Gln Ser Asp Leu Gly Glu Leu Pro Val Asp Ala Arg Phe Pro Pro
                20                  25                  30

Arg Val Pro Lys Ser Phe Pro Phe Asn Thr Ser Val Val Tyr Lys Lys
            35                  40                  45

Thr Leu Phe Val Glu Phe Thr Asp His Leu Phe Asn Ile Ala Lys Pro
        50                  55                  60

Arg Pro Pro Trp Met Gly Leu Leu Gly Pro Thr Ile Gln Ala Glu Val
65                  70                  75                  80
```

```
Tyr Asp Thr Val Val Ile Thr Leu Lys Asn Met Ala Ser His Pro Val
                 85                  90                  95

Ser Leu His Ala Val Gly Val Ser Tyr Trp Lys Ala Ser Glu Gly Ala
            100                 105                 110

Glu Tyr Asp Asp Gln Thr Ser Gln Arg Glu Lys Glu Asp Asp Lys Val
            115                 120                 125

Phe Pro Gly Gly Ser His Thr Tyr Val Trp Gln Val Leu Lys Glu Asn
            130                 135                 140

Gly Pro Met Ala Ser Asp Pro Leu Cys Leu Thr Tyr Ser Tyr Leu Ser
145                 150                 155                 160

His Val Asp Leu Val Lys Asp Leu Asn Ser Gly Leu Ile Gly Ala Leu
                165                 170                 175

Leu Val Cys Arg Glu Gly Ser Leu Ala Lys Glu Lys Thr Gln Thr Leu
            180                 185                 190

His Lys Phe Ile Leu Leu Phe Ala Val Phe Asp Glu Gly Lys Ser Trp
            195                 200                 205

His Ser Glu Thr Lys Asn Ser Leu Met Gln Asp Arg Asp Ala Ala Ser
            210                 215                 220

Ala Arg Ala Trp Pro Lys Met His Thr Val Asn Gly Tyr Val Asn Arg
225                 230                 235                 240

Ser Leu Pro Gly Leu Ile Gly Cys His Arg Lys Ser Val Tyr Trp His
                245                 250                 255

Val Ile Gly Met Gly Thr Thr Pro Glu Val His Ser Ile Phe Leu Glu
            260                 265                 270

Gly His Thr Phe Leu Val Arg Asn His Arg Gln Ala Ser Leu Glu Ile
            275                 280                 285

Ser Pro Ile Thr Phe Leu Thr Ala Gln Thr Leu Leu Met Asp Leu Gly
            290                 295                 300

Gln Phe Leu Leu Phe Cys His Ile Ser Ser His Gln His Asp Gly Met
305                 310                 315                 320

Glu Ala Tyr Val Lys Val Asp Ser Cys Pro Glu Glu Pro Gln Leu Arg
                325                 330                 335

Met Lys Asn Asn Glu Glu Ala Glu Asp Tyr Asp Asp Asp Leu Thr Asp
            340                 345                 350

Ser Glu Met Asp Val Val Arg Phe Asp Asp Asp Asn Ser Pro Ser Phe
            355                 360                 365

Ile Gln Ile Arg Ser Val Ala Lys Lys His Pro Lys Thr Trp Val His
            370                 375                 380

Tyr Ile Ala Ala Glu Glu Glu Asp Trp Asp Tyr Ala Pro Leu Val Leu
385                 390                 395                 400

Ala Pro Asp Asp Arg Ser Tyr Lys Ser Gln Tyr Leu Asn Asn Gly Pro
                405                 410                 415

Gln Arg Ile Gly Arg Lys Tyr Lys Lys Val Arg Phe Met Ala Tyr Thr
            420                 425                 430

Asp Glu Thr Phe Lys Thr Arg Glu Ala Ile Gln His Glu Ser Gly Ile
            435                 440                 445

Leu Gly Pro Leu Leu Tyr Gly Glu Val Gly Asp Thr Leu Leu Ile Ile
            450                 455                 460

Phe Lys Asn Gln Ala Ser Arg Pro Tyr Asn Ile Tyr Pro His Gly Ile
465                 470                 475                 480

Thr Asp Val Arg Pro Leu Tyr Ser Arg Arg Leu Pro Lys Gly Val Lys
                485                 490                 495
```

```
His Leu Lys Asp Phe Pro Ile Leu Pro Gly Glu Ile Phe Lys Tyr Lys
            500                 505                 510

Trp Thr Val Thr Val Glu Asp Gly Pro Thr Lys Ser Asp Pro Arg Cys
        515                 520                 525

Leu Thr Arg Tyr Tyr Ser Ser Phe Val Asn Met Glu Arg Asp Leu Ala
        530                 535                 540

Ser Gly Leu Ile Gly Pro Leu Leu Ile Cys Tyr Lys Glu Ser Val Asp
545                 550                 555                 560

Gln Arg Gly Asn Gln Ile Met Ser Asp Lys Arg Asn Val Ile Leu Phe
            565                 570                 575

Ser Val Phe Asp Glu Asn Arg Ser Trp Tyr Leu Thr Glu Asn Ile Gln
        580                 585                 590

Arg Phe Leu Pro Asn Pro Ala Gly Val Gln Leu Glu Asp Pro Glu Phe
        595                 600                 605

Gln Ala Ser Asn Ile Met His Ser Ile Asn Gly Tyr Val Phe Asp Ser
        610                 615                 620

Leu Gln Leu Ser Val Cys Leu His Glu Val Ala Tyr Trp Tyr Ile Leu
625                 630                 635                 640

Ser Ile Gly Ala Gln Thr Asp Phe Leu Ser Val Phe Phe Ser Gly Tyr
            645                 650                 655

Thr Phe Lys His Lys Met Val Tyr Glu Asp Thr Leu Thr Leu Phe Pro
        660                 665                 670

Phe Ser Gly Glu Thr Val Phe Met Ser Met Glu Asn Pro Gly Leu Trp
        675                 680                 685

Ile Leu Gly Cys His Asn Ser Asp Phe Arg Asn Arg Gly Met Thr Ala
        690                 695                 700

Leu Leu Lys Val Ser Ser Cys Asp Lys Asn Thr Gly Asp Tyr Tyr Glu
705                 710                 715                 720

Asp Ser Tyr Glu Asp Ile Ser Ala Tyr Leu Leu Ser Lys Asn Asn Ala
            725                 730                 735

Ile Glu Pro Arg Ser Phe Ser Gln Asn Ser Arg His Pro Ser Glu Gln
            740                 745                 750

Lys Leu Ile Ser Glu Glu Asp Leu Ser Gln Asn Pro Pro Val Leu Lys
            755                 760                 765

Arg His Gln Arg Glu Ile Thr Arg Thr Thr Leu Gln Ser Asp Gln Glu
        770                 775                 780

Glu Ile Asp Tyr Asp Asp Thr Ile Ser Val Glu Met Lys Lys Glu Asp
785                 790                 795                 800

Phe Asp Ile Tyr Asp Glu Asp Glu Asn Gln Ser Pro Arg Ser Phe Gln
            805                 810                 815

Lys Lys Thr Arg His Tyr Phe Ile Ala Ala Val Glu Arg Leu Trp Asp
            820                 825                 830

Tyr Gly Met Ser Ser Ser Pro His Val Leu Arg Asn Arg Ala Gln Ser
            835                 840                 845

Gly Ser Val Pro Gln Phe Lys Lys Val Val Phe Gln Glu Phe Thr Asp
        850                 855                 860

Gly Ser Phe Thr Gln Pro Leu Tyr Arg Gly Glu Leu Asn Glu His Leu
865                 870                 875                 880

Gly Leu Leu Gly Pro Tyr Ile Arg Ala Glu Val Glu Asp Asn Ile Met
            885                 890                 895

Val Thr Phe Arg Asn Gln Ala Ser Arg Pro Tyr Ser Phe Tyr Ser Ser
            900                 905                 910
```

Leu Ile Ser Tyr Glu Asp Gln Arg Gln Gly Ala Glu Pro Arg Lys
915                 920                 925

Asn Phe Val Lys Pro Asn Glu Thr Lys Thr Tyr Phe Trp Lys Val Gln
930                 935                 940

His His Met Ala Pro Thr Lys Asp Glu Phe Asp Cys Lys Ala Trp Ala
945                 950                 955                 960

Tyr Phe Ser Asp Val Asp Leu Glu Lys Asp Val His Ser Gly Leu Ile
                965                 970                 975

Gly Pro Leu Leu Val Cys His Thr Asn Thr Leu Asn Pro Ala His Gly
            980                 985                 990

Arg Gln Val Thr Val Gln Glu Phe Ala Leu Phe Phe Thr Ile Phe Asp
        995                 1000                1005

Glu Thr Lys Ser Trp Tyr Phe Thr Glu Asn Met Glu Arg Asn Cys
    1010                1015                1020

Arg Ala Pro Cys Asn Ile Gln Met Glu Asp Pro Thr Phe Lys Glu
    1025                1030                1035

Asn Tyr Arg Phe His Ala Ile Asn Gly Tyr Ile Met Asp Thr Leu
    1040                1045                1050

Pro Gly Leu Val Met Ala Gln Asp Gln Arg Ile Arg Trp Tyr Leu
    1055                1060                1065

Leu Ser Met Gly Ser Asn Glu Asn Ile His Ser Ile His Phe Ser
    1070                1075                1080

Gly His Val Phe Thr Val Arg Lys Lys Glu Glu Tyr Lys Met Ala
    1085                1090                1095

Leu Tyr Asn Leu Tyr Pro Gly Val Phe Glu Thr Val Glu Met Leu
    1100                1105                1110

Pro Ser Lys Ala Gly Ile Trp Arg Val Glu Cys Leu Ile Gly Glu
    1115                1120                1125

His Leu His Ala Gly Met Ser Thr Leu Phe Leu Val Tyr Ser Asn
    1130                1135                1140

Lys Cys Gln Thr Pro Leu Gly Met Ala Ser Gly His Ile Arg Asp
    1145                1150                1155

Phe Gln Ile Thr Ala Ser Gly Gln Tyr Gly Gln Trp Ala Pro Lys
    1160                1165                1170

Leu Ala Arg Leu His Tyr Ser Gly Ser Ile Asn Ala Trp Ser Thr
    1175                1180                1185

Ala Glu Pro Phe Ser Trp Ile Lys Val Asp Leu Leu Ala Pro Met
    1190                1195                1200

Ile Ile His Gly Ile Lys Thr Gln Gly Ala Arg Gln Lys Phe Ser
    1205                1210                1215

Ser Leu Tyr Ile Ser Gln Phe Ile Ile Met Tyr Ser Leu Asp Gly
    1220                1225                1230

Lys Lys Trp Gln Thr Tyr Arg Gly Asn Ser Thr Gly Thr Leu Met
    1235                1240                1245

Val Phe Phe Gly Asn Val Asp Ser Ser Gly Ile Lys His Asn Ile
    1250                1255                1260

Phe Asn Pro Pro Ile Ile Ala Arg Tyr Ile Arg Leu His Pro Thr
    1265                1270                1275

His Tyr Ser Ile Arg Ser Thr Leu Arg Met Glu Leu Met Gly Cys
    1280                1285                1290

Asp Leu Asn Ser Cys Ser Met Pro Leu Gly Met Glu Ser Lys Ala
    1295                1300                1305

-continued

```
Ile Ser Asp Ala Gln Ile Thr Ala Ser Ser Tyr Phe Thr Asn Met
1310                1315                1320

Phe Ala Thr Trp Ser Pro Ser Lys Ala Arg Leu His Leu Gln Gly
1325                1330                1335

Ala Ser Asn Ala Trp Arg Pro Gln Val Asn Asn Pro Lys Glu Trp
1340                1345                1350

Leu Gln Val Asp Phe Gln Lys Thr Met Lys Val Thr Gly Val Thr
1355                1360                1365

Thr Gln Gly Val Lys Ser Leu Leu Thr Ser Met Tyr Val Lys Glu
1370                1375                1380

Phe Leu Ile Ser Ser Ser Gln Asp Gly His Gln Trp Thr Leu Phe
1385                1390                1395

Phe Gln Asn Gly Lys Val Lys Val Phe Gln Gly Asn Gln Asp Ser
1400                1405                1410

Phe Thr Pro Val Val Asn Ser Leu Asp Pro Pro Leu Leu Thr Arg
1415                1420                1425

Tyr Leu Arg Ile His Pro Gln Ser Trp Val His Gln Ile Ala Leu
1430                1435                1440

Arg Met Glu Val Leu Gly Cys Glu Ala Gln Asp Leu Tyr
1445                1450                1455

<210> SEQ ID NO 8
<211> LENGTH: 1456
<212> TYPE: PRT
<213> ORGANISM: artificial
<220> FEATURE:
<223> OTHER INFORMATION: B domain deleted/truncated human FVIII variant
      comprising the R2090A and the R2215A substitutions.

<400> SEQUENCE: 8

Ala Thr Arg Arg Tyr Tyr Leu Gly Ala Val Glu Leu Ser Trp Asp Tyr
1               5                   10                  15

Met Gln Ser Asp Leu Gly Glu Leu Pro Val Asp Ala Arg Phe Pro Pro
            20                  25                  30

Arg Val Pro Lys Ser Phe Pro Phe Asn Thr Ser Val Val Tyr Lys Lys
        35                  40                  45

Thr Leu Phe Val Glu Phe Thr Asp His Leu Phe Asn Ile Ala Lys Pro
    50                  55                  60

Arg Pro Pro Trp Met Gly Leu Leu Gly Pro Thr Ile Gln Ala Glu Val
65                  70                  75                  80

Tyr Asp Thr Val Val Ile Thr Leu Lys Asn Met Ala Ser His Pro Val
                85                  90                  95

Ser Leu His Ala Val Gly Val Ser Tyr Trp Lys Ala Ser Glu Gly Ala
            100                 105                 110

Glu Tyr Asp Asp Gln Thr Ser Gln Arg Glu Lys Glu Asp Asp Lys Val
        115                 120                 125

Phe Pro Gly Gly Ser His Thr Tyr Val Trp Gln Val Leu Lys Glu Asn
    130                 135                 140

Gly Pro Met Ala Ser Asp Pro Leu Cys Leu Thr Tyr Ser Tyr Leu Ser
145                 150                 155                 160

His Val Asp Leu Val Lys Asp Leu Asn Ser Gly Leu Ile Gly Ala Leu
                165                 170                 175

Leu Val Cys Arg Glu Gly Ser Leu Ala Lys Glu Lys Thr Gln Thr Leu
            180                 185                 190

His Lys Phe Ile Leu Leu Phe Ala Val Phe Asp Glu Gly Lys Ser Trp
        195                 200                 205
```

-continued

His Ser Glu Thr Lys Asn Ser Leu Met Gln Asp Arg Asp Ala Ala Ser
210             215                 220

Ala Arg Ala Trp Pro Lys Met His Thr Val Asn Gly Tyr Val Asn Arg
225                 230                 235                 240

Ser Leu Pro Gly Leu Ile Gly Cys His Arg Lys Ser Val Tyr Trp His
            245                 250                 255

Val Ile Gly Met Gly Thr Thr Pro Glu Val His Ser Ile Phe Leu Glu
            260                 265                 270

Gly His Thr Phe Leu Val Arg Asn His Arg Gln Ala Ser Leu Glu Ile
            275                 280                 285

Ser Pro Ile Thr Phe Leu Thr Ala Gln Thr Leu Leu Met Asp Leu Gly
290                 295                 300

Gln Phe Leu Leu Phe Cys His Ile Ser Ser His Gln His Asp Gly Met
305                 310                 315                 320

Glu Ala Tyr Val Lys Val Asp Ser Cys Pro Glu Pro Gln Leu Arg
                325                 330                 335

Met Lys Asn Asn Glu Glu Ala Glu Asp Tyr Asp Asp Asp Leu Thr Asp
            340                 345                 350

Ser Glu Met Asp Val Val Arg Phe Asp Asp Asn Ser Pro Ser Phe
            355                 360                 365

Ile Gln Ile Arg Ser Val Ala Lys Lys His Pro Lys Thr Trp Val His
370                 375                 380

Tyr Ile Ala Ala Glu Glu Glu Asp Trp Asp Tyr Ala Pro Leu Val Leu
385                 390                 395                 400

Ala Pro Asp Asp Arg Ser Tyr Lys Ser Gln Tyr Leu Asn Asn Gly Pro
                405                 410                 415

Gln Arg Ile Gly Arg Lys Tyr Lys Lys Val Arg Phe Met Ala Tyr Thr
            420                 425                 430

Asp Glu Thr Phe Lys Thr Arg Glu Ala Ile Gln His Glu Ser Gly Ile
            435                 440                 445

Leu Gly Pro Leu Leu Tyr Gly Glu Val Gly Asp Thr Leu Leu Ile Ile
450                 455                 460

Phe Lys Asn Gln Ala Ser Arg Pro Tyr Asn Ile Tyr Pro His Gly Ile
465                 470                 475                 480

Thr Asp Val Arg Pro Leu Tyr Ser Arg Arg Leu Pro Lys Gly Val Lys
                485                 490                 495

His Leu Lys Asp Phe Pro Ile Leu Pro Gly Glu Ile Phe Lys Tyr Lys
            500                 505                 510

Trp Thr Val Thr Val Glu Asp Gly Pro Thr Lys Ser Asp Pro Arg Cys
            515                 520                 525

Leu Thr Arg Tyr Tyr Ser Ser Phe Val Asn Met Glu Arg Asp Leu Ala
530                 535                 540

Ser Gly Leu Ile Gly Pro Leu Leu Ile Cys Tyr Lys Glu Ser Val Asp
545                 550                 555                 560

Gln Arg Gly Asn Gln Ile Met Ser Asp Lys Arg Asn Val Ile Leu Phe
                565                 570                 575

Ser Val Phe Asp Glu Asn Arg Ser Trp Tyr Leu Thr Glu Asn Ile Gln
            580                 585                 590

Arg Phe Leu Pro Asn Pro Ala Gly Val Gln Leu Glu Asp Pro Glu Phe
            595                 600                 605

Gln Ala Ser Asn Ile Met His Ser Ile Asn Gly Tyr Val Phe Asp Ser
610                 615                 620

```
Leu Gln Leu Ser Val Cys Leu His Glu Val Ala Tyr Trp Tyr Ile Leu
625                 630                 635                 640

Ser Ile Gly Ala Gln Thr Asp Phe Leu Ser Val Phe Phe Ser Gly Tyr
            645                 650                 655

Thr Phe Lys His Lys Met Val Tyr Glu Asp Thr Leu Thr Leu Phe Pro
                660                 665                 670

Phe Ser Gly Glu Thr Val Phe Met Ser Met Glu Asn Pro Gly Leu Trp
            675                 680                 685

Ile Leu Gly Cys His Asn Ser Asp Phe Arg Asn Arg Gly Met Thr Ala
        690                 695                 700

Leu Leu Lys Val Ser Ser Cys Asp Lys Asn Thr Gly Asp Tyr Tyr Glu
705                 710                 715                 720

Asp Ser Tyr Glu Asp Ile Ser Ala Tyr Leu Leu Ser Lys Asn Asn Ala
                725                 730                 735

Ile Glu Pro Arg Ser Phe Ser Gln Asn Ser Arg His Pro Ser Glu Gln
            740                 745                 750

Lys Leu Ile Ser Glu Glu Asp Leu Ser Gln Asn Pro Pro Val Leu Lys
            755                 760                 765

Arg His Gln Arg Glu Ile Thr Arg Thr Thr Leu Gln Ser Asp Gln Glu
770                 775                 780

Glu Ile Asp Tyr Asp Asp Thr Ile Ser Val Glu Met Lys Lys Glu Asp
785                 790                 795                 800

Phe Asp Ile Tyr Asp Glu Asp Glu Asn Gln Ser Pro Arg Ser Phe Gln
            805                 810                 815

Lys Lys Thr Arg His Tyr Phe Ile Ala Ala Val Glu Arg Leu Trp Asp
            820                 825                 830

Tyr Gly Met Ser Ser Pro His Val Leu Arg Asn Arg Ala Gln Ser
            835                 840                 845

Gly Ser Val Pro Gln Phe Lys Lys Val Val Phe Gln Glu Phe Thr Asp
850                 855                 860

Gly Ser Phe Thr Gln Pro Leu Tyr Arg Gly Glu Leu Asn Glu His Leu
865                 870                 875                 880

Gly Leu Leu Gly Pro Tyr Ile Arg Ala Glu Val Glu Asp Asn Ile Met
            885                 890                 895

Val Thr Phe Arg Asn Gln Ala Ser Arg Pro Tyr Ser Phe Tyr Ser Ser
            900                 905                 910

Leu Ile Ser Tyr Glu Glu Asp Gln Arg Gln Gly Ala Glu Pro Arg Lys
            915                 920                 925

Asn Phe Val Lys Pro Asn Glu Thr Lys Thr Tyr Phe Trp Lys Val Gln
930                 935                 940

His His Met Ala Pro Thr Lys Asp Glu Phe Asp Cys Lys Ala Trp Ala
945                 950                 955                 960

Tyr Phe Ser Asp Val Asp Leu Glu Lys Asp Val His Ser Gly Leu Ile
                965                 970                 975

Gly Pro Leu Leu Val Cys His Thr Asn Thr Leu Asn Pro Ala His Gly
            980                 985                 990

Arg Gln Val Thr Val Gln Glu Phe Ala Leu Phe Phe Thr Ile Phe Asp
            995                 1000                1005

Glu Thr Lys Ser Trp Tyr Phe Thr Glu Asn Met Glu Arg Asn Cys
    1010                1015                1020

Arg Ala Pro Cys Asn Ile Gln Met Glu Asp Pro Thr Phe Lys Glu
    1025                1030                1035
```

```
Asn Tyr Arg Phe His Ala Ile Asn Gly Tyr Ile Met Asp Thr Leu
    1040                1045                1050

Pro Gly Leu Val Met Ala Gln Asp Gln Arg Ile Arg Trp Tyr Leu
    1055                1060                1065

Leu Ser Met Gly Ser Asn Glu Asn Ile His Ser Ile His Phe Ser
    1070                1075                1080

Gly His Val Phe Thr Val Arg Lys Lys Glu Glu Tyr Lys Met Ala
    1085                1090                1095

Leu Tyr Asn Leu Tyr Pro Gly Val Phe Glu Thr Val Glu Met Leu
    1100                1105                1110

Pro Ser Lys Ala Gly Ile Trp Arg Val Glu Cys Leu Ile Gly Glu
    1115                1120                1125

His Leu His Ala Gly Met Ser Thr Leu Phe Leu Val Tyr Ser Asn
    1130                1135                1140

Lys Cys Gln Thr Pro Leu Gly Met Ala Ser Gly His Ile Arg Asp
    1145                1150                1155

Phe Gln Ile Thr Ala Ser Gly Gln Tyr Gly Gln Trp Ala Pro Lys
    1160                1165                1170

Leu Ala Arg Leu His Tyr Ser Gly Ser Ile Asn Ala Trp Ser Thr
    1175                1180                1185

Lys Glu Pro Phe Ser Trp Ile Lys Val Asp Leu Leu Ala Pro Met
    1190                1195                1200

Ile Ile His Gly Ile Lys Thr Gln Gly Ala Ala Gln Lys Phe Ser
    1205                1210                1215

Ser Leu Tyr Ile Ser Gln Phe Ile Ile Met Tyr Ser Leu Asp Gly
    1220                1225                1230

Lys Lys Trp Gln Thr Tyr Arg Gly Asn Ser Thr Gly Thr Leu Met
    1235                1240                1245

Val Phe Phe Gly Asn Val Asp Ser Ser Gly Ile Lys His Asn Ile
    1250                1255                1260

Phe Asn Pro Pro Ile Ile Ala Arg Tyr Ile Arg Leu His Pro Thr
    1265                1270                1275

His Tyr Ser Ile Arg Ser Thr Leu Arg Met Glu Leu Met Gly Cys
    1280                1285                1290

Asp Leu Asn Ser Cys Ser Met Pro Leu Gly Met Glu Ser Lys Ala
    1295                1300                1305

Ile Ser Asp Ala Gln Ile Thr Ala Ser Ser Tyr Phe Thr Asn Met
    1310                1315                1320

Phe Ala Thr Trp Ser Pro Ser Lys Ala Arg Leu His Leu Gln Gly
    1325                1330                1335

Ala Ser Asn Ala Trp Arg Pro Gln Val Asn Asn Pro Lys Glu Trp
    1340                1345                1350

Leu Gln Val Asp Phe Gln Lys Thr Met Lys Val Thr Gly Val Thr
    1355                1360                1365

Thr Gln Gly Val Lys Ser Leu Leu Thr Ser Met Tyr Val Lys Glu
    1370                1375                1380

Phe Leu Ile Ser Ser Ser Gln Asp Gly His Gln Trp Thr Leu Phe
    1385                1390                1395

Phe Gln Asn Gly Lys Val Lys Val Phe Gln Gly Asn Gln Asp Ser
    1400                1405                1410

Phe Thr Pro Val Val Asn Ser Leu Asp Pro Pro Leu Leu Thr Arg
    1415                1420                1425
```

```
Tyr Leu Arg Ile His Pro Gln Ser Trp Val His Gln Ile Ala Leu
    1430                1435                1440

Arg Met Glu Val Leu Gly Cys Glu Ala Gln Asp Leu Tyr
1445                1450                1455

<210> SEQ ID NO 9
<211> LENGTH: 1456
<212> TYPE: PRT
<213> ORGANISM: artificial
<220> FEATURE:
<223> OTHER INFORMATION: B domain deleted/truncated human FVIII variant
      comprising the 2092A and the R2215A substitutions.

<400> SEQUENCE: 9

Ala Thr Arg Arg Tyr Tyr Leu Gly Ala Val Glu Leu Ser Trp Asp Tyr
1               5                   10                  15

Met Gln Ser Asp Leu Gly Glu Leu Pro Val Asp Ala Arg Phe Pro Pro
            20                  25                  30

Arg Val Pro Lys Ser Phe Pro Phe Asn Thr Ser Val Val Tyr Lys Lys
        35                  40                  45

Thr Leu Phe Val Glu Phe Thr Asp His Leu Phe Asn Ile Ala Lys Pro
    50                  55                  60

Arg Pro Pro Trp Met Gly Leu Leu Gly Pro Thr Ile Gln Ala Glu Val
65                  70                  75                  80

Tyr Asp Thr Val Val Ile Thr Leu Lys Asn Met Ala Ser His Pro Val
                85                  90                  95

Ser Leu His Ala Val Gly Val Ser Tyr Trp Lys Ala Ser Glu Gly Ala
            100                 105                 110

Glu Tyr Asp Asp Gln Thr Ser Gln Arg Glu Lys Glu Asp Asp Lys Val
        115                 120                 125

Phe Pro Gly Gly Ser His Thr Tyr Val Trp Gln Val Leu Lys Glu Asn
    130                 135                 140

Gly Pro Met Ala Ser Asp Pro Leu Cys Leu Thr Tyr Ser Tyr Leu Ser
145                 150                 155                 160

His Val Asp Leu Val Lys Asp Leu Asn Ser Gly Leu Ile Gly Ala Leu
                165                 170                 175

Leu Val Cys Arg Glu Gly Ser Leu Ala Lys Glu Lys Thr Gln Thr Leu
            180                 185                 190

His Lys Phe Ile Leu Leu Phe Ala Val Phe Asp Glu Gly Lys Ser Trp
        195                 200                 205

His Ser Glu Thr Lys Asn Ser Leu Met Gln Asp Arg Asp Ala Ala Ser
    210                 215                 220

Ala Arg Ala Trp Pro Lys Met His Thr Val Asn Gly Tyr Val Asn Arg
225                 230                 235                 240

Ser Leu Pro Gly Leu Ile Gly Cys His Arg Lys Ser Val Tyr Trp His
                245                 250                 255

Val Ile Gly Met Gly Thr Thr Pro Glu Val His Ser Ile Phe Leu Glu
            260                 265                 270

Gly His Thr Phe Leu Val Arg Asn His Arg Gln Ala Ser Leu Glu Ile
        275                 280                 285

Ser Pro Ile Thr Phe Leu Thr Ala Gln Thr Leu Leu Met Asp Leu Gly
    290                 295                 300

Gln Phe Leu Leu Phe Cys His Ile Ser Ser His Gln His Asp Gly Met
305                 310                 315                 320

Glu Ala Tyr Val Lys Val Asp Ser Cys Pro Glu Glu Pro Gln Leu Arg
                325                 330                 335
```

```
Met Lys Asn Asn Glu Glu Ala Glu Asp Tyr Asp Asp Leu Thr Asp
            340                 345                 350
Ser Glu Met Asp Val Val Arg Phe Asp Asp Asn Ser Pro Ser Phe
        355                 360                 365
Ile Gln Ile Arg Ser Val Ala Lys Lys His Pro Lys Thr Trp Val His
370                 375                 380
Tyr Ile Ala Ala Glu Glu Asp Trp Asp Tyr Ala Pro Leu Val Leu
385                 390                 395                 400
Ala Pro Asp Asp Arg Ser Tyr Lys Ser Gln Tyr Leu Asn Asn Gly Pro
                405                 410                 415
Gln Arg Ile Gly Arg Lys Tyr Lys Val Arg Phe Met Ala Tyr Thr
            420                 425                 430
Asp Glu Thr Phe Lys Thr Arg Glu Ala Ile Gln His Glu Ser Gly Ile
            435                 440                 445
Leu Gly Pro Leu Leu Tyr Gly Glu Val Gly Asp Thr Leu Leu Ile Ile
        450                 455                 460
Phe Lys Asn Gln Ala Ser Arg Pro Tyr Asn Ile Tyr Pro His Gly Ile
465                 470                 475                 480
Thr Asp Val Arg Pro Leu Tyr Ser Arg Arg Leu Pro Lys Gly Val Lys
                485                 490                 495
His Leu Lys Asp Phe Pro Ile Leu Pro Gly Glu Ile Phe Lys Tyr Lys
            500                 505                 510
Trp Thr Val Thr Val Glu Asp Gly Pro Thr Lys Ser Asp Pro Arg Cys
        515                 520                 525
Leu Thr Arg Tyr Tyr Ser Ser Phe Val Asn Met Glu Arg Asp Leu Ala
        530                 535                 540
Ser Gly Leu Ile Gly Pro Leu Leu Ile Cys Tyr Lys Glu Ser Val Asp
545                 550                 555                 560
Gln Arg Gly Asn Gln Ile Met Ser Asp Lys Arg Asn Val Ile Leu Phe
                565                 570                 575
Ser Val Phe Asp Glu Asn Arg Ser Trp Tyr Leu Thr Glu Asn Ile Gln
            580                 585                 590
Arg Phe Leu Pro Asn Pro Ala Gly Val Gln Leu Glu Asp Pro Glu Phe
        595                 600                 605
Gln Ala Ser Asn Ile Met His Ser Ile Asn Gly Tyr Val Phe Asp Ser
        610                 615                 620
Leu Gln Leu Ser Val Cys Leu His Glu Val Ala Tyr Trp Tyr Ile Leu
625                 630                 635                 640
Ser Ile Gly Ala Gln Thr Asp Phe Leu Ser Val Phe Phe Ser Gly Tyr
                645                 650                 655
Thr Phe Lys His Lys Met Val Tyr Glu Asp Thr Leu Thr Leu Phe Pro
            660                 665                 670
Phe Ser Gly Glu Thr Val Phe Met Ser Met Glu Asn Pro Gly Leu Trp
        675                 680                 685
Ile Leu Gly Cys His Asn Ser Asp Phe Arg Asn Arg Gly Met Thr Ala
        690                 695                 700
Leu Leu Lys Val Ser Ser Cys Asp Lys Asn Thr Gly Asp Tyr Tyr Glu
705                 710                 715                 720
Asp Ser Tyr Glu Asp Ile Ser Ala Tyr Leu Leu Ser Lys Asn Asn Ala
                725                 730                 735
Ile Glu Pro Arg Ser Phe Ser Gln Asn Ser Arg His Pro Ser Glu Gln
            740                 745                 750
```

```
Lys Leu Ile Ser Glu Glu Asp Leu Ser Gln Asn Pro Val Leu Lys
        755                 760                 765

Arg His Gln Arg Glu Ile Thr Arg Thr Thr Leu Gln Ser Asp Gln Glu
770                 775                 780

Glu Ile Asp Tyr Asp Asp Thr Ile Ser Val Glu Met Lys Lys Glu Asp
785                 790                 795                 800

Phe Asp Ile Tyr Asp Glu Asp Glu Asn Gln Ser Pro Arg Ser Phe Gln
                805                 810                 815

Lys Lys Thr Arg His Tyr Phe Ile Ala Ala Val Glu Arg Leu Trp Asp
        820                 825                 830

Tyr Gly Met Ser Ser Ser Pro His Val Leu Arg Asn Arg Ala Gln Ser
        835                 840                 845

Gly Ser Val Pro Gln Phe Lys Lys Val Val Phe Gln Glu Phe Thr Asp
850                 855                 860

Gly Ser Phe Thr Gln Pro Leu Tyr Arg Gly Glu Leu Asn Glu His Leu
865                 870                 875                 880

Gly Leu Leu Gly Pro Tyr Ile Arg Ala Glu Val Glu Asp Asn Ile Met
                885                 890                 895

Val Thr Phe Arg Asn Gln Ala Ser Arg Pro Tyr Ser Phe Tyr Ser Ser
        900                 905                 910

Leu Ile Ser Tyr Glu Glu Asp Gln Arg Gln Gly Ala Glu Pro Arg Lys
        915                 920                 925

Asn Phe Val Lys Pro Asn Glu Thr Lys Thr Tyr Phe Trp Lys Val Gln
        930                 935                 940

His His Met Ala Pro Thr Lys Asp Glu Phe Asp Cys Lys Ala Trp Ala
945                 950                 955                 960

Tyr Phe Ser Asp Val Asp Leu Glu Lys Asp Val His Ser Gly Leu Ile
                965                 970                 975

Gly Pro Leu Leu Val Cys His Thr Asn Thr Leu Asn Pro Ala His Gly
                980                 985                 990

Arg Gln Val Thr Val Gln Glu Phe Ala Leu Phe Phe Thr Ile Phe Asp
        995                 1000                1005

Glu Thr Lys Ser Trp Tyr Phe Thr Glu Asn Met Glu Arg Asn Cys
    1010                1015                1020

Arg Ala Pro Cys Asn Ile Gln Met Glu Asp Pro Thr Phe Lys Glu
    1025                1030                1035

Asn Tyr Arg Phe His Ala Ile Asn Gly Tyr Ile Met Asp Thr Leu
    1040                1045                1050

Pro Gly Leu Val Met Ala Gln Asp Gln Arg Ile Arg Trp Tyr Leu
    1055                1060                1065

Leu Ser Met Gly Ser Asn Glu Asn Ile His Ser Ile His Phe Ser
    1070                1075                1080

Gly His Val Phe Thr Val Arg Lys Lys Glu Glu Tyr Lys Met Ala
    1085                1090                1095

Leu Tyr Asn Leu Tyr Pro Gly Val Phe Glu Thr Val Glu Met Leu
    1100                1105                1110

Pro Ser Lys Ala Gly Ile Trp Arg Val Glu Cys Leu Ile Gly Glu
    1115                1120                1125

His Leu His Ala Gly Met Ser Thr Leu Phe Leu Val Tyr Ser Asn
    1130                1135                1140

Lys Cys Gln Thr Pro Leu Gly Met Ala Ser Gly His Ile Arg Asp
    1145                1150                1155
```

```
Phe Gln Ile Thr Ala Ser Gly Gln Tyr Gly Gln Trp Ala Pro Lys
    1160            1165            1170

Leu Ala Arg Leu His Tyr Ser Gly Ser Ile Asn Ala Trp Ser Thr
    1175            1180            1185

Lys Glu Pro Phe Ser Trp Ile Lys Val Asp Leu Leu Ala Pro Met
    1190            1195            1200

Ile Ile His Gly Ile Lys Thr Gln Gly Ala Arg Gln Ala Phe Ser
    1205            1210            1215

Ser Leu Tyr Ile Ser Gln Phe Ile Ile Met Tyr Ser Leu Asp Gly
    1220            1225            1230

Lys Lys Trp Gln Thr Tyr Arg Gly Asn Ser Thr Gly Thr Leu Met
    1235            1240            1245

Val Phe Phe Gly Asn Val Asp Ser Ser Gly Ile Lys His Asn Ile
    1250            1255            1260

Phe Asn Pro Pro Ile Ile Ala Arg Tyr Ile Arg Leu His Pro Thr
    1265            1270            1275

His Tyr Ser Ile Arg Ser Thr Leu Arg Met Glu Leu Met Gly Cys
    1280            1285            1290

Asp Leu Asn Ser Cys Ser Met Pro Leu Gly Met Glu Ser Lys Ala
    1295            1300            1305

Ile Ser Asp Ala Gln Ile Thr Ala Ser Ser Tyr Phe Thr Asn Met
    1310            1315            1320

Phe Ala Thr Trp Ser Pro Ser Lys Ala Arg Leu His Leu Gln Gly
    1325            1330            1335

Ala Ser Asn Ala Trp Arg Pro Gln Val Asn Asn Pro Lys Glu Trp
    1340            1345            1350

Leu Gln Val Asp Phe Gln Lys Thr Met Lys Val Thr Gly Val Thr
    1355            1360            1365

Thr Gln Gly Val Lys Ser Leu Leu Thr Ser Met Tyr Val Lys Glu
    1370            1375            1380

Phe Leu Ile Ser Ser Ser Gln Asp Gly His Gln Trp Thr Leu Phe
    1385            1390            1395

Phe Gln Asn Gly Lys Val Lys Val Phe Gln Gly Asn Gln Asp Ser
    1400            1405            1410

Phe Thr Pro Val Val Asn Ser Leu Asp Pro Pro Leu Leu Thr Arg
    1415            1420            1425

Tyr Leu Arg Ile His Pro Gln Ser Trp Val His Gln Ile Ala Leu
    1430            1435            1440

Arg Met Glu Val Leu Gly Cys Glu Ala Gln Asp Leu Tyr
    1445            1450            1455
```